(12) United States Patent
Rodgers et al.

(10) Patent No.: US 7,335,667 B2
(45) Date of Patent: Feb. 26, 2008

(54) PYRROLO[2,3-B]PYRIDIN-4-YL-AMINES AND PYRROLO[2,3-B]PYRIMIDIN-4-YL-AMINES AS JANUS KINASE INHIBITORS

(75) Inventors: James D. Rodgers, Landenberg, PA (US); Haisheng Wang, Hockessin, DE (US); Andrew P. Combs, Kennett Square, PA (US); Richard B. Sparks, Boothwyn, PA (US)

(73) Assignee: Incyte Corporation, Wilmington, DE (US)

( * ) Notice: Subject to any disclaimer, the term of this patent is extended or adjusted under 35 U.S.C. 154(b) by 58 days.

(21) Appl. No.: 11/313,394

(22) Filed: Dec. 21, 2005

(65) Prior Publication Data

US 2006/0183906 A1     Aug. 17, 2006

Related U.S. Application Data

(60) Provisional application No. 60/726,289, filed on Oct. 13, 2005, provisional application No. 60/638,474, filed on Dec. 22, 2004.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)

(52) U.S. Cl. .................. 514/300; 546/113; 544/116; 514/233.8

(58) Field of Classification Search ............... 546/113; 514/300, 233.8; 544/235, 116
See application file for complete search history.

(56) References Cited

U.S. PATENT DOCUMENTS

| 6,335,342 B1 * | 1/2002 | Longo et al. .......... 514/254.09 |
| 6,486,322 B1 * | 11/2002 | Longo et al. ................. 546/113 |
| 6,579,882 B2 | 6/2003 | Stewart et al. |
| 2003/0165576 A1 | 9/2003 | Fujii et al. |
| 2004/0198737 A1 | 10/2004 | Cox et al. |

FOREIGN PATENT DOCUMENTS

| DE | 3036390 | * 5/1982 |
| WO | WO 99/62908 | 12/1999 |
| WO | WO 99/65908 | 12/1999 |
| WO | WO 99/65909 | 12/1999 |
| WO | WO 01/42246 | 6/2001 |
| WO | WO 02/00661 | 1/2002 |
| WO | WO 02/060492 | 8/2002 |
| WO | WO 02/096909 | 12/2002 |
| WO | WO 03/048162 | 6/2003 |
| WO | WO 2004/047843 | 6/2004 |
| WO | WO 2004/099204 | 11/2004 |
| WO | WO 2004/099205 | 11/2004 |
| WO | WO 2005/051393 | 6/2005 |
| WO | WO 2005/060972 | 7/2005 |
| WO | WO 2005/105146 | 11/2005 |
| WO | WO 2005/105814 | 11/2005 |
| WO | WO 2006/013114 | 2/2006 |
| WO | WO 2006/056399 | 6/2006 |

OTHER PUBLICATIONS

Nishio et al., FEBS Letters, "Tyrosine kinase-dependent modulation by interferon-a of the ATP-sensitive K+ current in rabbit ventricular myocytes", vol. 445, 1999, pp. 87-91.*
Ishizaki et al, Molecular Pharmacology, "Pharmacological properties of Y-27632, a specific inhibitor of Pho-Associated kinases", 2000, vol. 57, pp. 976-983.*
Wu et al., Organic Letters, "One-Pot Two-step microwave-assisted reaction in constructing 4,5-disubstituted pyrazolopyrimidines", 2003, vol. 5, pp. 3587-3590.*
Pirard et al., Journal of chemical information and computer sciences, "Classification of kinase inhibitors using BCUT descriptors", 2000, vol. 40, pp. 1431-1440.*
Adv Pharmacol. 2000;47:113-74.
Agents Actions. Jan. 1993;38(1-2):116-21.
Bioreversible Carriers in Drug Design, ed. Edward B. Roche, American Pharmaceutical Association and Pergamon Press, 1987.
Candotti, F., L. Notarangelo, et al. (2002). "Molecular aspects of primary immunodeficiencies: lessons from cytokine and other signaling pathways." J Clin Invest 109(10): 1261-9).
Candotti, F., S. A. Oakes, et al. (1997) "Structural and functional basis for JAK3-deficient severe combined immunodeficiency." Blood 90(10):3996-4003).
Cetkovic-Cvrlje, M., A. L. Dragt, et al. (2003). "Targeting JAK3 with JANEX-1 for prevention of autoimmune type 1 diabetes in NOD mice." Clin Immunol 106(3):213-25.
De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8.
Gottlieb, A.B., et al, Nat Rev Drug Disc., 4:19-34.
Immunol Today. Jan. 1998;19(1):37-44.
JCI, 113:1664-1675.
Journal of Pharmaceutical Science, 66, 2 (1977).
Kawamura, M., D. W. McVicar, et al. (1994). "Molecular cloning of L-JAK, a Janus family protein-tyrosine kinase expressed in natural killer cells and activated leukocytes." Proc Natl Acad Sci U S A 91(14): 6374-8.
Levine, et al., Cancer Cell, vol. 7, 2005: 387-397.
Neubauer, H., A. Cumano, et al. (1998). Cell 93(3): 397-409.
Ortmann, R. A., T. Cheng, et al. (2000). "Janus kinases and signal transducers and activators of transcription: their roles in cytokine signaling, development and immunoregulation." Arthritis Res 2(1): 16-32).

(Continued)

*Primary Examiner*—Margaret D. Seaman
*Assistant Examiner*—Niloofar Rahmani
(74) *Attorney, Agent, or Firm*—Fish & Richardson P.C.

(57) ABSTRACT

The present invention provides pyrrolo[2,3-b]pyridine-4-yl amines pyrrolo[2,3-b]pyrimidin-4-yl amines that modulate the activity of Janus kinases and are useful in the treatment of diseases related to activity of Janus kinases including, for example, immune-related diseases and cancer.

38 Claims, 2 Drawing Sheets

OTHER PUBLICATIONS

Parganas, E., D. Wang, et al. (1998). Cell 93(3): 385-95.

Park et al., Analytical Biochemistry 1999, 269, 94-104.

Pernis, A. B. and P. B. Rothman (2002). "JAK-STAT signaling in asthma." J Clin Invest 109(10): 1279-83.

Remington's Pharmaceutical Sciences, 17th ed., Mack Publishing Company, Easton, Pa., 1985, p. 1418.

Rodig, S. J., M. A. Meraz, et al. (1998). "Disruption of the Jak1 gene demonstrates obligatory and nonredundant roles of the Jaks in cytokine-induced biologic responses." Cell 93(3): 373-83).

Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9.

Scott, M. J., C. J. Godshall, et al. (2002). "Jaks, STATs, Cytokines, and Sepsis." Clin Diagn Lab Immunol 9(6): 1153-9.

Seto, Y., H. Nakajima, et al. (2003). "Enhanced Th2 cell-mediated allergic inflammation in Tyk2-deficient mice." J Immunol 170(2): 1077-83.

T. Higuchi and V. Stella, "Pro-drugs as Novel Delivery Systems," vol. 14 of the A.C.S. Symposium Series.

T.W. Green and P.G.M. Wuts, Protective Groups in Organic Synthesis, 3rd. Ed., Wiley & Sons, Inc., New York (1999).

Takemoto, S., J. C. Mulloy, et al. (1997). "Proliferation of adult T cell leukemia/lymphoma cells is associated with the constitutive activation of JAK/STAT proteins." Proc Natl Acad Sci U S A 94(25): 13897-902.

International Search Report and Written Opinion for PCT/US2005/046207, 5 pages (May 15, 2007).

\* cited by examiner

FIGURE 2

| Accession # | Name | Sequence Description | Positive Control Fold Change | P | Test Compound Fold Change | % SUP | Dexamethasone Fold Change | % SUP |
|---|---|---|---|---|---|---|---|---|
| NM_009114 | S100a9 | S100 calcium-binding protein A9 (calgranulin B) | 47.7 | 0.0E+00 | 8.3 | 82.7 | 14.1 | 70.3 |
| AK089257 | AK089257 | similar to CYSTATIN A1 (STEFIN A1) [Sus scrofa] | 45.0 | 0.0E+00 | 5.8 | 87.1 | 8.5 | 81.1 |
| NM_013650 | S100a8 | Mus musculus S100 calcium binding protein A8 (calgranulin A) (S100a8), mRNA | 37.1 | 0.0E+00 | 7.2 | 80.7 | 18.6 | 49.8 |
| NM_020008 | Clecsf12 | C-type (calcium dependent, carbohydrate recognition domain) lectin, superfamily member | 22.1 | 0.0E+00 | 4.1 | 81.5 | 1.7 | 92.3 |
| NM_015783 | Isg15 | interferon-stimulated protein (15 kDa) | 21.1 | 0.0E+00 | 2.5 | 88.1 | 7.2 | 66.0 |
| NM_008327 | Ifi202a | interferon activated gene 202A | 18.6 | 0.0E+00 | 2.7 | 85.7 | 8.8 | 52.8 |
| NM_021443 | Scya8 | small inducible cytokine A8 | 17.3 | 0.0E+00 | 2.5 | 85.8 | 6.4 | 62.9 |
| NM_011409 | Slfn3 | schlafen 3 | 15.7 | 5.3E-08 | 1.2 | 92.5 | 2.5 | 84.3 |
| NM_013653 | Scya5 | small inducible cytokine A5 | 14.7 | 0.0E+00 | 2.7 | 81.3 | 3.7 | 74.7 |
| AF099976 | Slfn4 | schlafen 4 | 14.3 | 4.8E-22 | 1.1 | 92.5 | 1.7 | 88.1 |
| NM_025288 | Stfa3 | stefin A3 | 13.8 | 0.0E+00 | 2.1 | 84.9 | 2.5 | 82.1 |
| NM_009425 | Tnfsf10 | tumor necrosis factor (ligand) superfamily, member 10 | 11.7 | 2.7E-14 | 3.5 | 70.2 | 2.8 | 75.8 |
| AK079685 | AK079685 | interferon regulatory factor 7 | 10.4 | 0.0E+00 | 1.9 | 81.6 | 3.1 | 70.2 |
| NM_021718 | Ly116 | lymphocyte antigen 116 | 10.2 | 9.1E-09 | 1.9 | 81.7 | 2.7 | 73.6 |
| NM_011408 | Slfn2 | schlafen 2 | 10.0 | 0.0E+00 | 2.8 | 71.7 | 3.1 | 69.5 |
| NM_009117 | Saa1 | serum amyloid A1 | 9.2 | 0.0E+00 | 2.7 | 70.4 | 4.5 | 50.9 |
| NM_009140 | Scyb2 | small inducible cytokine subfamily, member 2 | 8.8 | 0.0E+00 | 2.5 | 71.8 | 1.4 | 83.8 |
| NM_017466 | Cmkbrl2 | chemokine (C-C) receptor 1, like 2 | 8.2 | 4.5E-26 | 1.9 | 76.4 | 2.0 | 75.6 |
| NM_009100 | Rptn | repetin | 8.0 | 2.0E-29 | 2.1 | 74.1 | 1.4 | 82.8 |
| NM_011314 | Saa2 | serum amyloid A2 | 7.9 | 0.0E+00 | 1.4 | 82.3 | 2.8 | 64.1 |
| NM_030712 | Cxcr6 | chemokine (C-X-C) receptor 6 | 7.5 | 1.3E-20 | 1.1 | 85.8 | 1.2 | 83.4 |
| NM_010654 | Klrd1 | killer cell lectin-like receptor, subfamily D, member 1 | 7.2 | 2.7E-25 | 2.0 | 72.3 | 2.0 | 72.7 |
| NM_010370 | Gzma | granzyme A | 7.0 | 2.2E-19 | -1.0 | 114.6 | 1.4 | 79.9 |
| NM_021281 | Ctss | cathepsin S | 6.8 | 0.0E+00 | 1.5 | 78.4 | 2.8 | 58.3 |
| NM_013487 | Cd3d | CD3 antigen, delta polypeptide | 6.6 | 4.6E-34 | 1.8 | 73.4 | 1.7 | 74.3 |
| NM_008332 | Ifit2 | interferon-induced protein with tetratricopeptide repeats 2 | 6.5 | 3.0E-20 | 1.1 | 82.2 | 1.3 | 79.7 |
| U93277 | Alox15b | arachidonate 15-lipoxygenase, second type | 5.7 | 1.8E-39 | -1.1 | 119.8 | -1.4 | 124.5 |
| AF453945 | AF453945 | Mus musculus interleukin 19 (Il19) mRNA, partial cds | 5.6 | 7.6E-24 | 1.0 | 81.5 | 1.5 | 73.7 |
| | | AVERAGE | 14.4 | | 2.4 | 83.4 | 3.9 | 72.8 |

US 7,335,667 B2

PYRROLO[2,3-B]PYRIDIN-4-YL-AMINES AND PYRROLO[2,3-B]PYRIMIDIN-4-YL-AMINES AS JANUS KINASE INHIBITORS

CROSS-REFERENCE TO RELATED APPLICATIONS

This application claims the benefit of U.S. Ser. Nos. 60/638,474, filed Dec. 22, 2004, and 60/726,289, filed Oct. 13, 2005, the disclosures of each of which are incorporated herein by reference in their entireties.

FIELD OF THE INVENTION

The present invention provides pyrrolo[2,3-b]pyridine-4-yl amines and pyrrolo[2,3-b]pyrimidin-4-yl amines that modulate the activity of Janus kinases and are useful in the treatment of diseases related to activity of Janus kinases including, for example, immune-related diseases, skin disorders, and cancer.

BACKGROUND OF THE INVENTION

The immune system responds to injury and threats from pathogens. Cytokines are low-molecular weight polypeptides or glycoproteins that stimulate biological responses in virtually all cell types. For example, cytokines regulate many of the pathways involved in the host inflammatory response to sepsis. Cytokines influence cell differentiation, proliferation and activation, and they can modulate both proinflammatory and anti-inflammatory responses to allow the host to react appropriately to pathogens.

Binding of a cytokine to its cell surface receptor initiates intracellular signaling cascades that transduce the extracellular signal to the nucleus, ultimately leading to changes in gene expression. The pathway involving the Janus kinase family of protein tyrosine kinases (JAKs) and Signal Transducers and Activators of Transcription (STATs) is engaged in the signaling of a wide range of cytokines. Generally, cytokine receptors do not have intrinsic tyrosine kinase activity, and thus require receptor-associated kinases to propagate a phosphorylation cascade. JAKs fulfill this function. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription (Scott, M. J., C. J. Godshall, et al. (2002). "Jaks, STATs, Cytokines, and Sepsis." Clin Diagn Lab Immunol 9(6): 1153-9).

The JAK family plays a role in the cytokine-dependent regulation of proliferation and function of cells involved in immune response. Currently, there are four known mammalian JAK family members: JAK1 (also known as Janus kinase-1), JAK2 (also known as Janus kinase-2), JAK3 (also known as Janus kinase, leukocyte; JAKL; L-JAK and Janus kinase-3) and TYK2 (also known as protein-tyrosine kinase 2). The JAK proteins range in size from 120 to 140 kDa and comprise seven conserved JAK homology (JH) domains; one of these is a functional catalytic kinase domain, and another is a pseudokinase domain potentially serving a regulatory function and/or serving as a docking site for STATs (Scott, Godshall et al. 2002, supra).

While JAK1, JAK2 and TYK2 are ubiquitously expressed, JAK3 is reported to be preferentially expressed in natural killer (NK) cells and not resting T cells, suggesting a role in lymphoid activation (Kawamura, M., D. W. McVicar, et al. (1994). "Molecular cloning of L-JAK, a Janus family protein-tyrosine kinase expressed in natural killer cells and activated leukocytes." Proc Natl Acad Sci USA 91(14): 6374-8).

Not only do the cytokine-stimulated immune and inflammatory responses contribute to normal host defense, they also play roles in the pathogenesis of diseases: pathologies such as severe combined immunodeficiency (SCID) arise from hypoactivity and suppression of the immune system, and a hyperactive or inappropriate immune/inflammatory response contributes to the pathology of autoimmune diseases such as rheumatoid and psoriatic arthritis, asthma and systemic lupus erythematosus, as well as illnesses such as scleroderma and osteoarthritis (Ortmann, R. A., T. Cheng, et al. (2000). "Janus kinases and signal transducers and activators of transcription: their roles in cytokine signaling, development and immunoregulation." Arthritis Res 2(1): 16-32). Furthermore, syndromes with a mixed presentation of autoimmune and immunodeficiency disease are quite common (Candotti, F., L. Notarangelo, et al. (2002). "Molecular aspects of primary immunodeficiencies: lessons from cytokine and other signaling pathways." J Clin Invest 109(10): 1261-9). Thus, therapeutic agents are typically aimed at augmentation or suppression of the immune and inflammatory pathways, accordingly.

Deficiencies in expression of JAK family members are associated with disease states. Jak1−/− mice are runted at birth, fail to nurse, and die perinatally (Rodig, S. J., M. A. Meraz, et al. (1998). "Disruption of the Jak1 gene demonstrates obligatory and nonredundant roles of the Jaks in cytokine-induced biologic responses." Cell 93(3): 373-83). Jak2−/− mouse embryos are anemic and die around day 12.5 postcoitum due to the absence of definitive erythropoiesis. JAK2-deficient fibroblasts do not respond to IFNgamma, although responses to IFNalpha/beta and IL-6 are unaffected. JAK2 functions in signal transduction of a specific group of cytokine receptors required in definitive erythropoiesis (Neubauer, H., A. Cumano, et al. (1998). Cell 93(3): 397-409; Parganas, E., D. Wang, et al. (1998). Cell 93(3): 385-95.). JAK3 appears to play a role in normal development and function of B and T lymphocytes. Mutations of JAK3 are reported to be responsible for autosomal recessive severe combined immunodeficiency (SCID) in humans (Candotti, F., S. A. Oakes, et al. (1997). "Structural and functional basis for JAK3-deficient severe combined immunodeficiency." Blood 90(10): 3996-4003).

The JAK/STAT pathway, and in particular all four members of the JAK family, are believed to play a role in the pathogenesis of the asthmatic response. The inappropriate immune responses that characterize asthma are orchestrated by a subset of CD4+ T helper cells termed T helper 2 (Th2) cells. Signaling through the cytokine receptor IL-4 stimulates JAK1 and JAK3 to activate STAT6, and signaling through IL-12 stimulates activation of JAK2 and TYK2, and subsequent phosphorylation of STAT4. STAT4 and STAT6 control multiple aspects of CD4+ T helper cell differentiation (Pernis, A. B. and P. B. Rothman (2002). "JAK-STAT signaling in asthma." J Clin Invest 109(10): 1279-83). Furthermore, TYK2-deficient mice were found to have enhanced Th2 cell-mediated allergic airway inflammation (Seto, Y., H. Nakajima, et al. (2003). "Enhanced Th2 cell-mediated allergic inflammation in Tyk2-deficient mice." J Immunol 170(2): 1077-83).

The JAK/STAT pathway, and in particular, JAK3, also plays a role in cancers of the immune system. In adult T cell leukemia/lymphoma (ATLL), human CD4+ T cells acquire a transformed phenotype, an event that correlates with acquisition of constitutive phosphorylation of JAKs and STATs. Furthermore, an association between JAK3 and STAT-1, STAT-3, and STAT-5 activation and cell-cycle progression was demonstrated by both propidium iodide staining and bromodeoxyuridine incorporation in cells of four ATLL patients tested. These results imply that JAK/STAT activation is associated with replication of leukemic cells and that therapeutic approaches aimed at JAK/STAT inhibition may be considered to halt neoplastic growth (Takemoto, S., J. C. Mulloy, et al. (1997). "Proliferation of adult T cell leukemia/lymphoma cells is associated with the constitutive activation of JAK/STAT proteins." Proc Natl Acad Sci USA 94(25): 13897-902).

Blocking signal transduction at the level of the JAK kinases holds promise for developing treatments for human cancers. Cytokines of the interleukin 6 (IL-6) family, which activate the signal transducer gp130, are major survival and growth factors for human multiple myeloma (MM) cells. The signal transduction of gp130 is believed to involve JAK1, JAK2 and Tyk2 and the downstream effectors STAT3 and the mitogen-activated protein kinase (MAPK) pathways. In IL-6-dependent MM cell lines treated with the JAK2 inhibitor tyrphostin AG490, JAK2 kinase activity and ERK2 and STAT3 phosphorylation were inhibited. Furthermore, cell proliferation was suppressed and apoptosis was induced (De Vos, J., M. Jourdan, et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells." Br J Haematol 109(4): 823-8). However, in some cases, AG490 Can induce dormancy of tumor cells and actually then protect them from death.

Pharmacological targeting of Janus kinase 3 (JAK3) has been employed successfully to control allograft rejection and graft versus host disease (GVHD). In addition to its involvement in signaling of cytokine receptors, JAK3 is also engaged in the CD40 signaling pathway of peripheral blood monocytes. During CD40-induced maturation of myeloid dendritic cells (DCs), JAK3 activity is induced, and increases in costimulatory molecule expression, IL-12 production, and potent allogeneic stimulatory capacity are observed. A rationally designed JAK3 inhibitor WHI-P-154 prevented these effects arresting the DCs at an immature level, suggesting that immunosuppressive therapies targeting the tyrosine kinase JAK3 may also affect the function of myeloid cells (Saemann, M. D., C. Diakos, et al. (2003). "Prevention of CD40-triggered dendritic cell maturation and induction of T-cell hyporeactivity by targeting of Janus kinase 3." Am J Transplant 3(11): 1341-9). In the mouse model system, JAK3 was also shown to be an important molecular target for treatment of autoimmune insulin-dependent (type 1) diabetes mellitus. The rationally designed JAK3 inhibitor JANEX-1 exhibited potent immunomodulatory activity and delayed the onset of diabetes in the NOD mouse model of autoimmune type 1 diabetes (Cetkovic-Cvrlje, M., A. L. Dragt, et al. (2003). "Targeting JAK3 with JANEX-1 for prevention of autoimmune type 1 diabetes in NOD mice." Clin Immunol 106(3): 213-25).

It has been suggested that inhibition of JAK2 tyrosine kinase can be beneficial for patients with myeloproliferative disorder. (Levin, et al., Cancer Cell, vol. 7, 2005: 387-397) Myeloprofiferative disorder (MPD) includes polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES) and systemic mast cell disease (SMCD). Although the myeloproliferative disorder (such as PV, ET and MMM) are thought to be caused by acquired somatic mutation in hematopoietic progenitors, the genetic basis for these diseases has not been known. However, it has been reported that hematopoietic cells from a majority of patients with PV and a significant number of patients with ET and MMM possess a recurrent somatic activing mutation in the JAK2 tyrosine kinase. It has also been reported that inhibition of the JAK2V617F kinase with a small molecule inhibtor leads to inhibition of proliferation of hematopoietic cells, suggesting that the JAK2 tyrosine kinase is a potential target for pharmacologic inhibition in patients with PV, ET and MMM.

Inhibition of the Jak kinases is also envisioned to have therapeutic benefits in patients suffering from skin immune disorders such as psoriasis, and skin sensitization. In psoriasis vulgaris, the most common form of psoriasis, it has been generally accepted that activated T lymphocytes are important for the maintenance of the disease and its associated psoriatic plaques (Gottlieb, A. B., et al, Nat Rev Drug Disc., 4:19-34). Psoriatic plaques contain a significant immune infiltrate, including leukocytes and monocytes, as well as multiple epidermal layers with increased keratinocyte proliferation. While the initial activation of immune cells in psoriasis occurs by an ill defined mechanism, the maintenance is believed to be dependent on a number of inflammatory cytokines, in addition to various chemokines and growth factors (JCI, 113:1664-1675). Many of these, including interleukins -2, -4, -6, -7, -12, -15, -18, and -23 as well as GM-CSF and IFNg, signal through the Janus (Jak) kinases (Adv Pharmacol. 2000; 47:113-74). As such, blocking signal transduction at the level of Jak kinases may result in therapeutic benefits in patients suffering from psoriasis or other immune disorders of the skin.

It has been known that certain therapeutics can cause immune reactions such as skin rash or diarrhea in some patients. For instance, administration of some of the new targeted anti-cancer agents such as Iressa, Erbitux, and Tarceva has induced acneiform rash with some patients. Another example is that some therapeutics used topically induce skin irritation, skin rash, contact dermatitis or allergic contact sensitization. For some patients, these immune reactions may be bothersome, but for others, the immune reactions such as rash or diarrhea may result in inability to continue the treatment. Although the driving force behind these immune reactions has not been elucidated completely at the present time, these immune reactions are certainly linked to immune infiltrate. In light of JAK/STAT pathway, it has also been envisioned that inhibition of the Jak kinases, such as topical or systemic administration of a Jak inhibitor, may prevent or ameliorate the side effects of immune reactions (skin irritation, skin rash, contact dermatitis, allergic contact sensitization, or diarrhea) caused by some other therapeutics. The Jak inhibitor can be administered before, during or after the treatment of the other therapeutics to prevent or lessen the side effects.

Inhibitors of Janus kinases or related kinases are widely sought and several publications report effective classes of compounds. For example, certain inhibitors are reported in US 2004/0198737; WO 2004/099204; WO 2004/099205; and WO 01/42246.

Thus, new or improved agents which inhibit Janus kinases are continually needed that act as immunosuppressive agents for organ transplants, as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease), diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds, compositions and methods described herein are directed toward these and other ends.

SUMMARY OF THE INVENTION

The present invention provides compounds of Formulas I and II:

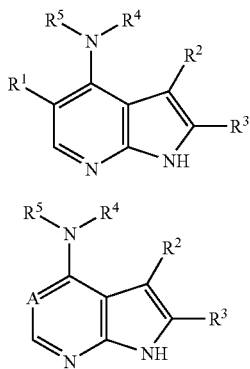

or pharmaceutically acceptable salt forms or prodrugs thereof, wherein constituent members are provided hereinbelow.

The present invention further provides compositions comprising Formula I and a pharmaceutically acceptable carrier.

The present invention further provides methods of modulating an activity of JAK comprising contacting JAK with a compound of Formula I.

The present invention further provides methods of treating a disease in a patient, where the disease is associated with JAK activity, comprising administering to the patient a therapeutically effective amount of a compound of Formula I.

The present invention further provides compositions for topical administration where the compositions comprise a compound of Formula II and a pharmaceutically acceptable carrier.

The present invention further provides methods of treating skin disorders in a patient by topically administering a therapeutically effective amount of a compound of Formula II.

BRIEF DESCRIPTION OF THE DRAWINGS

FIG. 2 shows data of the inhibition by a JAK inhibitor of transcriptional changes associated with immune challenged ears in the murine model of DTH.

DETAILED DESCRIPTION

Figure 1:
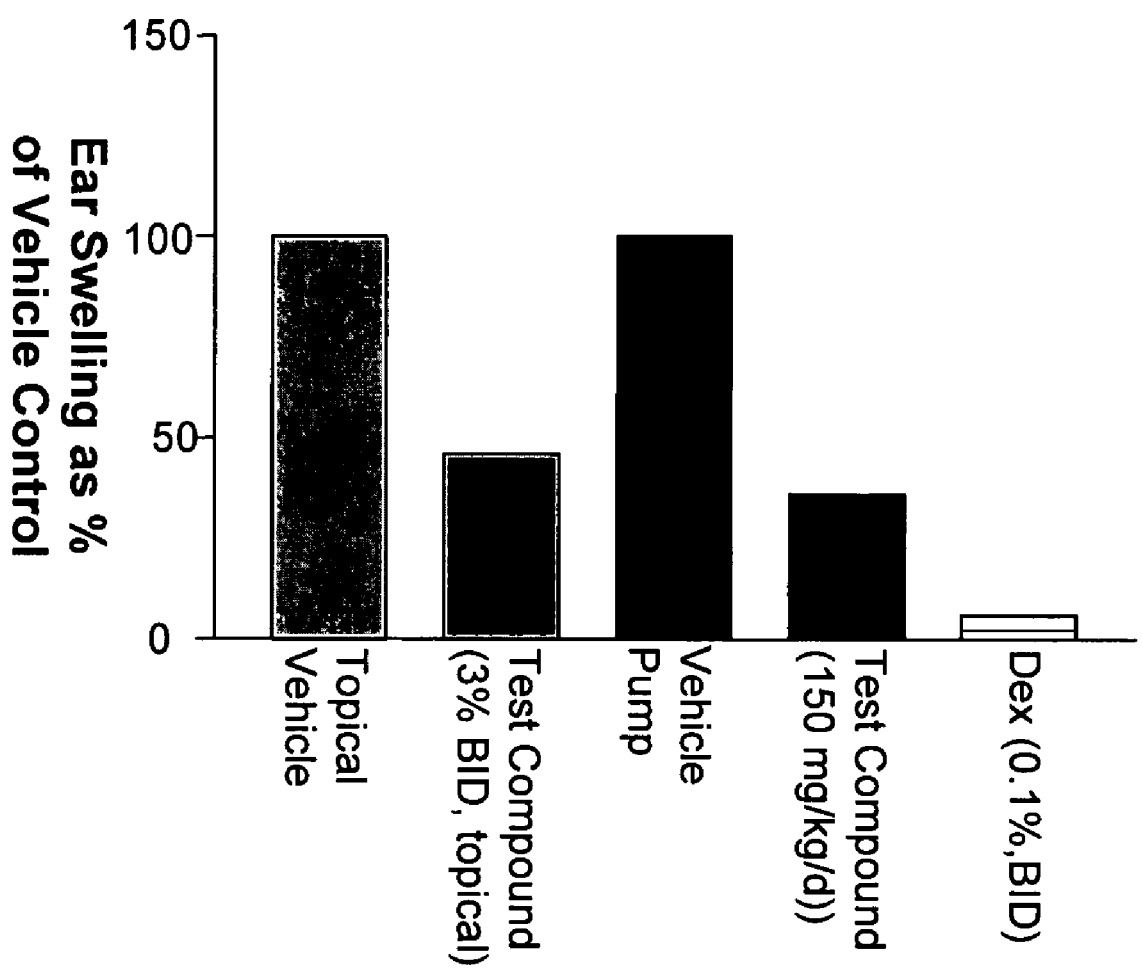
FIG. 1 shows systemic and topical activity of a JAK inhibitor in the murine DTH model for dermatitis.

The present invention provides, inter alia, compounds of Formula I:

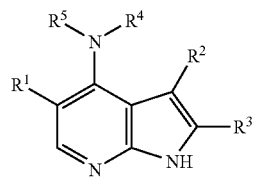

or pharmaceutically acceptable salt forms or prodrug thereof, wherein:

$R^1$, $R^2$, and $R^3$ are each, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^4$ is H, $C_{1-4}$ alkyl, $C_{2-4}$ alkenyl, $C_{2-4}$ alkynyl, $S(O)_2R^9$, $SOR^9$, cycloalkyl, or heterocycloalkyl, wherein said $C_{1-4}$ alkyl, $C_{2-4}$ alkenyl, $C_{2-4}$ alkynyl, cycloalkyl, heterocycloalkyl are each optionally substituted with 1, 2 or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$;

$R^5$ is 3-8 membered cycloalkyl, 3-8 membered heterocycloalkyl, —L—(3-8 membered cycloalkyl), —L—(3-8 membered heterocycloalkyl), each substituted by one $R^6$ and 0, 1 or 2 $R^7$;

L is $C_{1-4}$ alkylenyl, $C_{2-4}$ alkenylenyl, $C_{2-4}$ alkynylenyl, O, S, $NR^{14}$, CO, COO, OCO, $NR^{14}C(O)O$, $CONR^{14}$, SO, $SO_2$, $SONR^{14}$, $SO_2NR^{14}$, or $NR^{14}CONR^{14}$;

$R^6$ is —$W^1$—$W^2$—$W^3$—$W^4$—$W^5$—$W^6$—$R^{13}$;

$W^1$ is absent, $C_{1-4}$ alkylenyl, $C_{2-4}$ alkenylenyl, $C_{2-4}$ alkynylenyl, aryl, heteroaryl, cycloalkyl or heterocycloalkyl, each optionally substituted by 1, 2 or 3 halo, CN, $NO_2$, OH, =NH, =NOH, =NO—($C_{1-4}$alkyl), $C_{1-4}$ haloalkyl, $C_{1-4}$alkoxy, $C_{1-4}$ haloalkoxy, amino, $C_{1-4}$ alkylamino or $C_{2-8}$ dialkylamino;

$W^2$ is absent, $C_{1-4}$ alkylenyl, $C_{2-4}$ alkenylenyl, $C_{2-4}$ alkynylenyl, O, S, $NR^{12}$, CO, COO, OCO, C(S), $C(S)NR^{12}$, —C(=N—CN)—, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

$W^3$ is absent, $C_{1-4}$ alkylenyl, $C_{2-4}$ alkenylenyl, $C_{2-4}$ alkynylenyl, aryl, cycloalkyl, heteroaryl or heterocycloalkyl, wherein said $C_{1-4}$ alkylenyl, $C_{2-4}$ alkenylenyl, $C_{2-4}$ alkynylenyl, aryl, cycloalkyl, heteroaryl or heterocycloalkyl is optionally substituted by 1, 2 or 3 halo, CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^4$ is absent, $C_{1-4}$ alkylenyl, $C_{2-4}$ alkenylenyl, $C_{2-4}$ alkynylenyl, O, S, $NR^{12}$, CO, COO, OCO, —C(=N—CN)—, $NR^{12}C(O)O$, $CONR^{12}$, SO, $SO_2$, $SONR^{12}$, $SO_2NR^{12}$, or NR$^{12}$CONR$^{12}$, wherein said C$_{1-4}$ alkylenyl, C$_{2-4}$ alkenylenyl, C$_{2-4}$ alkynylenyl, are each optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^5$ is absent, C$_{1-4}$ alkylenyl, C$_{2-4}$ alkenylenyl, C$_{2-4}$ alkynylenyl, aryl, cycloalkyl, heteroaryl or heterocycloalkyl, wherein said C$_{1-4}$ alkylenyl, C$_{2-4}$ alkenylenyl, C$_{2-4}$ alkynylenyl, aryl, cycloalkyl, heteroaryl or heterocycloalkyl is optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^6$ is absent, C$_{1-4}$ alkyl, C$_{2-4}$ alkenyl, C$_{2-4}$ alkynyl, O, S, NR$^{12}$, CO, COO, OCO, —C(=N—CN)—, NR$^{12}$C(O)O, CONR$^{12}$, SO, SO$_2$, SONR$^{12}$, SO$_2$NR$^{12}$, or NR$^{12}$CONR$^{12}$, wherein said C$_{1-4}$ alkyl, C$_{2-4}$ alkenyl, C$_{2-4}$ alkynyl are each optionally substituted by 1, 2 or 3 CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

R$^7$ is halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-NR$^{c''}$R$^{d''}$, —(C$_{1-6}$alkyl)-S(O)$_2$R$^{b''}$, or —(C$_{1-6}$ alkyl)-S(O)$_2$NR$^{c''}$R$^{d''}$;

R$^9$ is C$_{1-4}$ alkyl, aryl, heteroaryl, cycloalkyl, or heterocycloalkyl, each optionally substituted with 1, 2, or 3 substituents selected from halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^{a'}$, SR$^{a'}$, C(O)R$^{b'}$, C(O)NR$^{c'}$R$^{d'}$, C(O)OR$^{a'}$, OC(O)R$^{b'}$, OC(O)NR$^{c'}$R$^{d'}$, NR$^{c'}$R$^{d'}$, NR$^{c'}$C(O)R$^{d'}$, NR$^{c'}$C(O)OR$^{a'}$, S(O)R$^{b'}$, S(O)NR$^{c'}$R$^{d'}$, S(O)$_2$R$^{b'}$, and S(O)$_2$NR$^{c'}$R$^{d'}$;

R$^{12}$ and R$^{14}$ are each, independently, H or C$_{1-6}$ alkyl optionally substituted by 1, 2 or 3 substituents selected from OH, CN, NO$_2$, amino, (C$_{1-4}$ alkyl)amino, (C$_{2-8}$ dialkyl)amino, C$_{1-6}$ haloalkyl, C$_{1-6}$ acyl, C$_{1-6}$ acyloxy, C$_{1-6}$ acylamino, —(C$_{1-6}$ alkyl)-CN, and —(C$_{1-6}$ alkyl)-NO$_2$;

R$^{13}$ is halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, or —(C$_{1-6}$ alkyl)-S(O)$_2$NR$^{c''}$R$^{d''}$, wherein each of said C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl or heterocycloalkylalkyl is optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$alkyl)-S(O)R$^{b''}$, —(C$_{1-6}$ alkyl)-S(O)NR$^{c''}$R$^{d''}$, —(C$_{1-6}$ alkyl)—S(O)$_2$R$^{b''}$, and —(C$_{1-6}$ alkyl)-S(O)$_2$NR$^{c''}$R$^{d''}$;

R$^a$, R$^{a'}$ and R$^{a''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$, R$^{b'}$ and R$^{b''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

R$^{c'}$ and R$^{d'}$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^{c'}$ and R$^{d'}$ together with the N atom to which they are attached form a 4-, 5-, 6- or 7-membered heterocycloalkyl group; and R$^{c''}$ and R$^{d''}$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^{c''}$ and R$^{d''}$ together with the N atom to which they are attached form a 4-, 5-, 6- or 7-membered heterocycloalkyl group.

The present invention further provides compounds of Formula II:

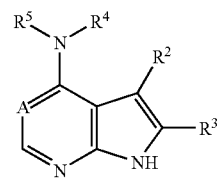

II or pharmaceutically acceptable salt forms or prodrugs thereof, wherein:

A is N or CR$^1$;

R$^1$, R$^2$, and R$^3$ are each, independently, H, halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

R$^4$ is H, C$_{1-4}$ alkyl, C$_{2-4}$ alkenyl, C$_{2-4}$ alkynyl, S(O)$_2$R$^9$, SOR$^9$, cycloalkyl, or heterocycloalkyl, wherein said C$_{1-4}$ alkyl, C$_{2-4}$ alkenyl, C$_{2-4}$ alkynyl, cycloalkyl, heterocycloalkyl are each optionally substituted with 1, 2 or 3 substituents selected from halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

R$^5$ is 3-8 membered cycloalkyl, 3-8 membered heterocycloalkyl, —L—(3-8 membered cycloalkyl), —L—(3-8 membered heterocycloalkyl), each substituted by one R$^6$ and 0, 1 or 2 R$^7$;

L is C$_{1-4}$ alkylenyl, C$_{2-4}$ alkenylenyl, C$_{2-4}$ alkynylenyl, O, S, NR$^{14}$, CO, COO, OCO, NR$^{14}$C(O)O, CONR$^{14}$, SO, SO$_2$, SONR$^{14}$, SO$_2$NR$^{14}$, or NR$^{14}$CONR$^{14}$;

R$^6$ is —W$^1$—W$^2$—W$^3$—W$^4$—W$^5$—W$^6$—R$^{13}$;

W$^1$ is absent, C$_{1-4}$ alkylenyl, C$_{2-4}$ alkenylenyl, C$_{2-4}$ alkynylenyl, aryl, heteroaryl, cycloalkyl or heterocycloalkyl, each optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^2$ is absent, C$_{1-4}$ alkylenyl, C$_{2-4}$ alkenylenyl, C$_{2-4}$ alkynylenyl, O, S, NR$^{12}$, CO, COO, OCO, C(S), C(S)NR$^{12}$, —C(=N—CN)—, NR$^{12}$C(O)O, CONR$^{12}$, SO, SO$_2$, SONR$^{12}$, SO$_2$NR$^{12}$, or NR$^{12}$CONR$^{12}$, wherein said C$_{1-4}$ alkylenyl, C$_{2-4}$ alkenylenyl, C$_{2-4}$ alkynylenyl, are each optionally substituted by 1, 2 or 3 halo, OH, C$_{1-4}$ alkoxy, C$_{1-4}$ haloalkoxy, amino, C$_{1-4}$ alkylamino or C$_{2-8}$ dialkylamino;

W$^3$ is absent, C$_{1-4}$ alkylenyl, C$_{2-4}$ alkenylenyl, C$_{2-4}$ alkynylenyl, aryl, cycloalkyl, heteroaryl or heterocycloalkyl, wherein said C$_{1-4}$ alkylenyl, C$_{2-4}$ alkenylenyl, C$_{2-4}$ alkynylenyl, aryl, cycloalkyl, heteroaryl or heterocycloalkyl is optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^4$ is absent, C$_{1-4}$ alkylenyl, C$_{2-4}$ alkenylenyl, C$_{2-4}$ alkynylenyl, O, S, NR$^{12}$, CO, COO, OCO, —C(=N—CN)—, NR$^{12}$C(O)O, CONR$^{12}$, SO, SO$_2$, SONR$^{12}$, SO$_2$NR$^{12}$, or NR$^{12}$CONR$^{12}$, wherein said C$_{1-4}$ alkylenyl, C$_{2-4}$ alkenylenyl, C$_{2-4}$ alkynylenyl, are each optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^5$ is absent, C$_{1-4}$ alkylenyl, C$_{2-4}$ alkenylenyl, C$_{2-4}$ alkynylenyl, aryl, cycloalkyl, heteroaryl or heterocycloalkyl, wherein said C$_{1-4}$ alkylenyl, C$_{2-4}$ alkenylenyl, C$_{2-4}$ alkynylenyl, aryl, cycloalkyl, heteroaryl or heterocycloalkyl is optionally substituted by 1, 2 or 3 halo, CN, NO$_2$, OH, =NH, =NOH, =NO—(C$_{1-4}$ alkyl), C$_{1-4}$ haloalkyl, C$_{1-4}$ alkoxy, C$_{1-4}$ haloalkoxy, amino, C$_{1-4}$ alkylamino or C$_{2-8}$ dialkylamino;

W$^6$ is absent, C$_{1-4}$ alkyl, C$_{2-4}$ alkenyl, C$_{2-4}$ alkynyl, O, S, NR$^{12}$, CO, COO, OCO, —C(=N—CN)—, NR$^{12}$C(O)O, CONR$^{12}$, SO, SO$_2$, SONR$^{12}$, SO$_2$NR$^{12}$, or NR$^{12}$CONR$^{12}$, wherein said C$_{1-4}$ alkyl, C$_{2-4}$ alkenyl, C$_{2-4}$ alkynyl are each optionally substituted by 1, 2 or 3 CN, NO$_2$, OH, =NH, =NOH, =NO—(C$_{1-4}$ alkyl), C$_{2-4}$ haloalkyl, C$_{1-4}$ alkoxy, C$_{1-4}$ haloalkoxy, amino, C$_{1-4}$ alkylamino or C$_{2-8}$ dialkylamino;

R$^7$ is halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, or —(C$_{1-6}$ alkyl)-S(O)$_2$NR$^{c''}$R$^{d''}$;

R$^9$ is C$_{1-4}$ alkyl, aryl, heteroaryl, cycloalkyl, or heterocycloalkyl, each optionally substituted with 1, 2, or 3 substituents selected from halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^{a'}$, SR$^{a'}$, C(O)R$^{b'}$, C(O)NR$^{c'}$R$^{d'}$, C(O)OR$^{a'}$, OC(O)R$^{b'}$, OC(O)NR$^{c'}$R$^{d'}$, NR$^{c'}$R$^{d'}$, NR$^{c'}$C(O)R$^{d'}$, NR$^{c'}$C(O)OR$^{a'}$, S(O)R$^{b'}$, S(O)NR$^{c'}$R$^{d'}$, S(O)$_2$R$^{b'}$, and S(O)$_2$NR$^{c'}$R$^{d'}$;

R$^{12}$ and R$^{14}$ are each, independently, H or C$_{1-6}$ alkyl optionally substituted by 1, 2 or 3 substituents selected from OH, CN, NO$_2$, amino, (C$_{1-4}$ alkyl)amino, (C$_{2-8}$ dialkyl)amino, C$_{1-6}$ haloalkyl, C$_{1-6}$ acyl, C$_{1-6}$ acyloxy, C$_{1-6}$ acylamino, —(C$_{1-6}$ alkyl)-CN, and —(C$_{1-6}$ alkyl)-NO$_2$;

R$^{13}$ is halo, C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, (C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$alkyl)-S(O)R$^{b''}$, —(C$_{1-6}$ alkyl)-S(O)NR$^{c''}$R$^{d''}$, —(C$_{1-6}$alkyl)-S(O)$_2$R$^{b''}$, or —(C$_{1-6}$ alkyl)-S(O)$_2$NR$^{c''}$R$^{d''}$, wherein each of said C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl or heterocycloalkylalkyl is optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ alkyl)-S(O)$_2$NR$^{c''}$R$^{d''}$;

R$^a$, R$^{a'}$ and R$^{a''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$, R$^{b'}$ and R$^{b''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

R$^{c'}$ and R$^{d'}$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or $R^{c'}$ and $R^{d'}$ together with the N atom to which they are attached form a 4-, 5-, 6- or 7-membered heterocycloalkyl group; and $R^{c''}$ and $R^{d''}$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^{c''}$ and $R^{d''}$ together with the N atom to which they are attached form a 4-, 5-, 6- or 7-membered heterocycloalkyl group.

In some embodiments, A is $CR^1$.

In some embodiments, A is N.

In some embodiments, $R^1$ is H.

In some embodiments, $R^2$ is H.

In some embodiments, $R^3$ is H.

In some embodiments, $R^4$ is H or $C_{1-4}$ alkyl.

In some embodiments, $R^4$ is methyl.

In some embodiments, $R^5$ is 3-8 membered heterocycloalkyl substituted by one $R^6$ and 0, 1 or $2R^7$.

In some embodiments, $R^5$ is 6-membered heterocycloalkyl substituted by one $R^6$ and 0, 1 or $2R^7$.

In some embodiments, $R^5$ is piperidinyl substituted by one $R^6$ and 0, 1 or 2 $R^7$.

In some embodiments, $R^5$ is piperidin-3-yl substituted by one $R^6$ and 0, 1 or 2 $R^7$.

In some further embodiments, $R^6$ is substituted on the piperidinyl N-atom.

In some embodiments, $R^5$ is —L—pyrrolidinyl; L is $C_{1-4}$ alkylenyl; and the pyrrolidinyl is substituted by one $R^6$ and 0, 1 or 2 $R^7$.

In some embodiments, $R^5$ is —L—pyrrolidin-2-yl; L is $C_{1-4}$ alkylenyl and the pyrrolidin-2-yl is substituted by one $R^6$ and 0, 1 or 2 $R^7$.

In some embodiments, $W^2$ is absent, $C_{1-4}$ alkylenyl, $C_{2-4}$ alkenylenyl, $C_{2-4}$ alkynylenyl, O, S, $NR^{12}$, CO, COO, OCO, —C(=N—CN)—, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 substituents independently selected from halo, OH, $C_{1-4}$ alkoxy, $C_{1-4}$ haloalkoxy, amino, $C_{1-4}$ alkylamino, and $C_{2-8}$ dialkylamino.

In some embodiments, $W^2$ is $SO_2$, CO, COO, $C(S)NR^{12}$, or $CONR^{12}$.

In some embodiments, $W^2$ is $SO_2$, CO, COO, C(S)NH, CONH or —CON($C_{1-4}$ alkyl)—.

In some embodiments, $W^2$ is $SO_2$ or CO.

In some embodiments, $W^3$ is $C_{1-4}$ alkylenyl or cycloalkyl.

In some embodiments, $R^{13}$ is halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, —($C_{1-6}$ alkyl)-CN, —($C_{1-6}$ alkyl)-$NO_2$, —($C_{1-6}$ alkyl)-$OR^{a''}$, —($C_{1-6}$ alkyl)-$SR^{a''}$, —($C_{1-6}$ alkyl)-$C(O)R^{b''}$, —($C_{1-6}$ alkyl)-$C(O)NR^{c''}R^{d''}$, —($C_{1-6}$ alkyl)-$C(O)OR^{a''}$, —($C_{1-6}$ alkyl)-$OC(O)R^{b''}$, —($C_{1-6}$ alkyl)-$OC(O)NR^{c''}R^{d''}$, —($C_{1-6}$ alkyl)-$NR^{c''}R^{d''}$, —($C_{1-6}$ alkyl)-$NR^{c''}C(O)R^{d''}$, —($C_{1-6}$ alkyl)-$NR^{c''}C(O)OR^{a''}$, —($C_{1-6}$ alkyl)-$S(O)R^{b''}$, —($C_{1-6}$ alkyl)-$S(O)NR^{c''}R^{d''}$, —($C_{1-6}$ alkyl)-$S(O)_2R^{b''}$, or —($C_{1-6}$ alkyl)-$S(O)_2NR^{c''}R^{d''}$.

In some embodiments, $R^{13}$ is $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

$C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, —($C_{1-6}$ alkyl)-CN, —($C_{1-6}$ alkyl)-$NO_2$, —($C_{1-6}$ alkyl)-$OR^{a''}$, —($C_{1-6}$ alkyl)$SR^{a''}$, —($C_{1-6}$ alkyl)-$C(O)R^{b''}$, —($C_{1-6}$ alkyl)-$C(O)NR^{c''}R^{d''}$, —($C_{1-6}$ alkyl)-$C(O)OR^{a''}$, —($C_{1-6}$ alkyl)-$OC(O)R^{b''}$, —($C_{1-6}$ alkyl)-$OC(O)NR^{c''}R^{d''}$, ($C_{1-6}$ alkyl)-$NR^{c''}R^{d''}$, —($C_{1-6}$ alkyl)-$NR^{c''}C(O)R^{d''}$, —($C_{1-6}$ alkyl)-$NR^{c''}C(O)OR^{a''}$, —($C_{1-6}$ alkyl)-$S(O)R^{b''}$, —($C_{1-6}$ alkyl)-$S(O)NR^{c''}R^{d''}$, —($C_{1-6}$ alkyl)-$S(O)_2R^{b''}$, and —($C_{1-6}$ alkyl)-$S(O)_2NR^{c''}R^{d''}$.

In some embodiments, $R^{13}$ is aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

$C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, —($C_{1-6}$ alkyl)-CN, —($C_{1-6}$ alkyl)-$NO_2$, —($C_{1-6}$ alkyl)-$OR^{a''}$, —($C_{1-6}$ alkyl)-$SR^{a''}$, —($C_{1-6}$ alkyl)-$C(O)R^{b''}$, —($C_{1-6}$ alkyl)-$C(O)NR^{c''}R^{d''}$, —($C_{1-6}$ alkyl)-$C(O)OR^{a''}$, —($C_{1-6}$ alkyl)-$OC(O)R^{b''}$, —($C_{1-6}$ alkyl)-$OC(O)NR^{c''}R^{d''}$, —($C_{1-6}$ alkyl)-$NR^{c''}R^{d''}$, —($C_{1-6}$ alkyl)-$NR^{c''}C(O)R^{d''}$, —($C_{1-6}$ alkyl)-$NR^{c''}C(O)OR^{a''}$, —($C_{1-6}$ alkyl)-$S(O)R^{b''}$, —($C_{1-6}$ alkyl)-$S(O)NR^{c''}R^{d''}$, —($C_{1-6}$ alkyl)-$S(O)_2R^{b''}$, and —($C_{1-6}$ alkyl)-$S(O)_2NR^{c''}R^{d''}$.

In some embodiments, $R^{13}$ is $C_{1-6}$ alkyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, $OR^{a''}$, $SR^{a''}$, $C(O)R^{b''}$, $C(O)OR^{a''}$, $NR^{c''}C(O)R^{d''}$, $S(O)_2R^{b''}$, and —($C_{1-6}$ alkyl)-CN.

In some embodiments, $R^{13}$ is aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, $OR^{a''}$, $SR^{a''}$, $C(O)R^{b''}$, $C(O)OR^{a''}$, $NR^{c''}C(O)R^{d''}$, $S(O)_2R^{b''}$, and —($C_{1-6}$ alkyl)-CN.

In some embodiments, $R^{13}$ is $C_{1-6}$ alkyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, OH, $C_{1-4}$ alkoxy, $C_{1-4}$ haloalkoxy, heteroaryloxy, aryloxy, —$SC_{1-6}$ alkyl, —C(O)—$C_{1-6}$ alkyl, —C(O)O$C_{1-6}$ alkyl, —S(O)$_2C_{1-6}$ alkyl, —NHC(O)—$C_{1-6}$ alkyl, and —($C_{1-6}$ alkyl)-CN.

In some embodiments, $R^{13}$ is aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, OH, $C_{1-4}$ alkoxy, $C_{1-4}$ haloalkoxy, heteroaryloxy, aryloxy, —$SC_{1-6}$ alkyl, —C(O)—$C_{1-6}$ alkyl, —C(O)O$C_{1-6}$ alkyl, —S(O)$_2C_{1-6}$ alkyl, —NHC(O)—$C_{1-6}$ alkyl, and —($C_{1-6}$ alkyl)-CN.

In some embodiments, $R^{13}$ is aryl, cycloalkyl, heteroaryl or heterocycloalkyl, each optionally substituted by 1, 2, 3, 4 or 5 substituents independently selected from $C_{1-6}$ alkyl, $C_{1-6}$ haloalkyl, aryl, heteroaryl, halo, CN, OH, $C_{1-4}$ alkoxy, $C_{1-4}$ haloalkoxy, heteroaryloxy, aryloxy, —$SC_{1-6}$ alkyl, —C(O)—$C_{1-6}$ alkyl, —C(O)O$C_{1-6}$ alkyl, —S(O)$_2C_{1-6}$ alkyl, —NHC(O)—$C_{1-6}$ alkyl, and —($C_{1-6}$ alkyl)-CN.

In some embodiments, $R^{13}$ is arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, OH, $C_{1-4}$ alkoxy, $C_{1-4}$ haloalkoxy, heteroaryloxy, aryloxy, —$SC_{1-6}$ alkyl, —C(O)—$C_{1-6}$ alkyl, —C(O)O$C_{1-6}$ alkyl, —S(O)$_2C_{1-6}$ alkyl, —NHC(O)—$C_{1-6}$ alkyl, and —($C_{1-6}$ alkyl)-CN.

In some embodiments, $R^{13}$ is OH or CN.

In some embodiments, $W^1$ is absent, $W^2$ is CO or SO$_2$, $W^3$ is $C_{1-4}$ alkyleneyl or cycloalkyl, $W^4$ is absent, $W^5$ is absent, $W^6$ is absent, and $R^{13}$ is CN or OH.

In some embodiments, $R^6$ is —$W^2$—$W^3$—$R^3$.

In some embodiments, $R^6$ is —CO—CH$_2$—CN.

In some embodiments, $R^6$ is —$W^2$—$R^{13}$.

In some embodiments, $R^6$ is $R^{13}$.

In some embodiments:

$R^6$ is —$W^2$—$R^{13}$;

$W^2$ is SO$_2$, CO, COO, C(S)NR$^{12}$, or CONR$^{12}$; and $R^{13}$ is $C_{1-6}$ alkyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

$C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —($C_{1-6}$ alkyl)-CN, —($C_{1-6}$ alkyl)-NO$_2$, —($C_{1-6}$ alkyl)-OR$^{a''}$, —($C_{1-6}$ alkyl)-SR$^{a''}$, —($C_{1-6}$ alkyl)-C(O)R$^{b''}$, —($C_{1-6}$ alkyl)-C(O)NR$^{c''}$R$^{d''}$, —($C_{1-6}$ alkyl)-C(O)OR$^{a''}$, —($C_{1-6}$ alkyl)-OC(O)R$^{b''}$, —($C_{1-6}$ alkyl)-OC(O)NR$^{c''}$R$^{d''}$, —($C_{1-6}$ alkyl)-NR$^{c''}$R$^{d''}$, —($C_{1-6}$ alkyl)-NR$^{c''}$C(O)R$^{d''}$, —($C_{1-6}$ alkyl)-NR$^{c''}$C(O)OR$^{a''}$, —($C_{1-6}$ alkyl)-S(O)R$^{b''}$, —($C_{1-6}$ alkyl)-S(O)NR$^{c''}$R$^{d''}$, —($C_{1-6}$ alkyl)-S(O)$_2$R$^{b''}$, and —($C_{1-6}$ alkyl)-S(O)$_2$NR$^{c''}$R$^{d''}$.

In some embodiments, the compounds of formula I of the present invention have the structure of Formula I-A:

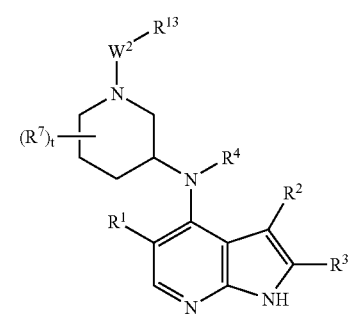

I-A wherein t is 0, 1 or 2.

In some embodiments, the compounds of the invention have Formula I-A wherein:

$W^2$ is SO$_2$, CO, COO, C(S)NR$^{12}$, or CONR$^{12}$;

$R^{13}$ is $C_{1-6}$ alkyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

$C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —($C_{1-6}$ alkyl)-CN, —($C_{1-6}$ alkyl)-NO$_2$, —($C_{1-6}$ alkyl)-OR$^{a''}$, —($C_{1-6}$ alkyl)-SR$^{a''}$, —($C_{1-6}$ alkyl)-C(O)R$^{b''}$, —($C_{1-6}$ alkyl)-C(O)NR$^{c''}$R$^{d''}$, —($C_{1-6}$ alkyl)-C(O)OR$^{a''}$, —($C_{1-6}$ alkyl)-OC(O)R$^{b''}$, —($C_{1-6}$ alkyl)-OC(O)NR$^{c''}$R$^{d''}$, —($C_{1-6}$ alkyl)-NR$^{c''}$R$^{d''}$, —($C_{1-6}$ alkyl)-NR$^{c''}$C(O)R$^{d''}$, —($C_{1-6}$ alkyl)-NR$^{c''}$C(O)OR$^{a''}$, —($C_{1-6}$ alkyl)-S(O)R$^{b''}$, —($C_{1-6}$ alkyl)-S(O)NR$^{c''}$R$^{d''}$, —($C_{1-6}$ alkyl)-S(O)$_2$R$^{b''}$, and —($C_{1-6}$ alkyl)-S(O)$_2$NR$^{c''}$R$^{d''}$; and t is 0, 1 or 2.

In some embodiments, t is 0.

In some embodiments, t is 1.

In some embodiments, t is 2.

In some embodiments, the compounds of the present invention have the structure of Formula I-B:

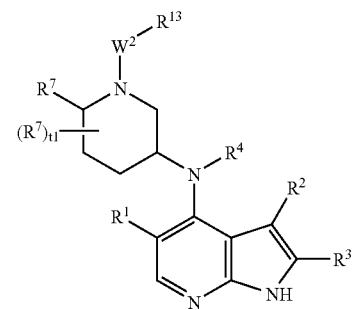

I-B wherein t1 is 0 or 1.

In some further embodiments, the compounds of the invention have Formula I-B wherein:

$R^{13}$ is $C_{1-6}$ alkyl, $C_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, $OR^{a''}$, $SR^{a''}$, $C(O)R^{b''}$, $C(O)OR^{a''}$, $NR^{c''}C(O)R^{d''}$, $S(O)_2R^{b''}$, and —($C_{1-6}$ alkyl)-CN;

$W^2$ is $SO_2$, CO, COO, C(S)NH, CONH or —CON($C_{1-4}$ alkyl)-; and $R^4$ is $C_{1-4}$ alkyl, $C_{2-4}$ alkenyl, $C_{2-4}$ alkynyl, $S(O)_2R^9$, $SOR^9$, cycloalkyl, or heterocycloalkyl, wherein said $C_{1-4}$ alkyl, $C_{2-4}$ alkenyl, $C_{2-4}$ alkynyl, cycloalkyl, heterocycloalkyl are each optionally substituted with 1, 2 or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

In some embodiments, t1 is 0.

In some embodiments, t1 is 1.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a bivalent alkyl group.

As used herein, "alkenyl" refers to an alkyl group having one or more double carbon-carbon bonds. Example alkenyl groups include ethenyl, propenyl, cyclohexenyl, and the like. The term "alkenylenyl" refers to a bivalent alkenyl group.

As used herein, "alkynyl" refers to an alkyl group having one or more triple carbon-carbon bonds. Example alkynyl groups include ethynyl, propynyl, and the like. The term "alkynylenyl" referes to a bivalent alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenan-threnyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of pentane, pentene, hexane, and the like. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 Carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles containing at least one ring-forming heteroatom such as an O, N, or S atom. Heterocycloalkyl groups can include mono- or polycyclic (e.g., having 2, 3 or 4 fused rings) ring systems. Any ring-forming heteroatom or ring-forming carbon atom of a heterocycloalkyl group can also be oxidized by one or two oxo or sulfido substituents. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "aryloxy" refers to an —O-aryl group. An example aryloxy group is phenoxy.

As used herein, "heteroaryloxy" refers to an —O-heteroaryl group. An example heteroaryloxy group is pyridin-2-yloxy or pyridin-3-yloxy.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "arylalkyl" refers to an alkyl group substituted by an aryl group.

As used herein, "heteroarylalkyl" refers to an alkyl group substituted by a heteroaryl group.

As used herein, "cycloalkylalkyl" refers to an alkyl group substituted by a cycloalkyl group.

As used herein, "heterocycloalkylalkyl" refers to an alkyl group substituted by a heterocycloalkyl group.

As used herein, "acyl" refers to —C(O)-alkyl.

As used herein, "acyloxy" refers to —OC(O)-alkyl.

As used herein, "acylamino" refers to an amino group substituted with an acyl group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Compounds of the invention can be prepared according to numerous preparatory routes known in the literature. Example synthetic methods for preparing compounds of the invention are provided in the Schemes below.

Scheme 1 shows an example synthesis of compounds of the invention starting with pyrrolo[2,3-b]pyridines 1-1 from which the N-oxo analog (1-2) is made by treatment with an oxidant such as m-CPBA. The N-oxide 1-2 can be halogenated with a halogenating agent such as MeSO$_2$Cl, to form a 4-halo compound 1-3 (Y is halo such as Cl). The 4-amino compounds of the invention (1-4) can be generated by treatment of 1-3 with an appropriate amine (NHR$^4$R$^5$), optionally in the presence of heat. In some instances, the pyrrolo amine of 1-3 can be protected with a suitable amino protecting group prior to reaction with NHR$^4$R$^5$, and the amino protecting group can be removed after the reaction with NHR$^4$R$^5$.

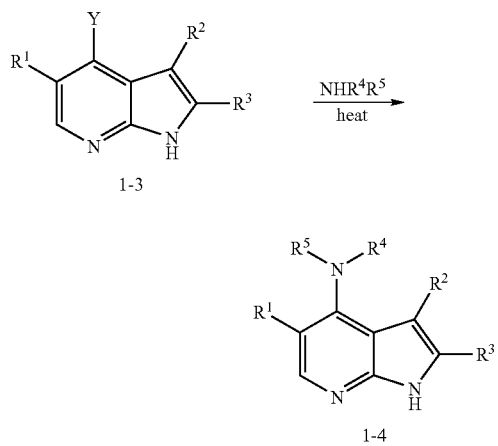

Scheme 2 provides an example synthesis of compounds of the invention where R$^5$ is piperidin-3-yl. A 4-chloro compound 2-1 (wherein the pyrrolo amine group can optionally be protected by an appropriate amino protecting group; in cases where the pyrrolo amine group is protected, the protecting group can be removed in a later stage), can be treated with a protected piperidine 2-2 to form a 4-piperidine compound 2-3. The protecting group at the N-atom on the piperidine moiety of 2-3 can be removed by routine methods (e.g., hydrogenation in the presence of Pd catalyst and HCl to remove benzyl protecting group) to form a compound 2-4. Alkylation or acylation of the N-atom on the piperidine moiety of 2-4 with a reagent such as R$^6$—X, where X is a leaving group such as halo, hydroxyl, mesylate, tosylate, etc., affords a compound 2-5 of the invention. For example, R$^6$—X can be a carboxylic acid, acid chloride, alkyl/aryl sulfonyl chloride, haloalkane, etc.

Scheme 2

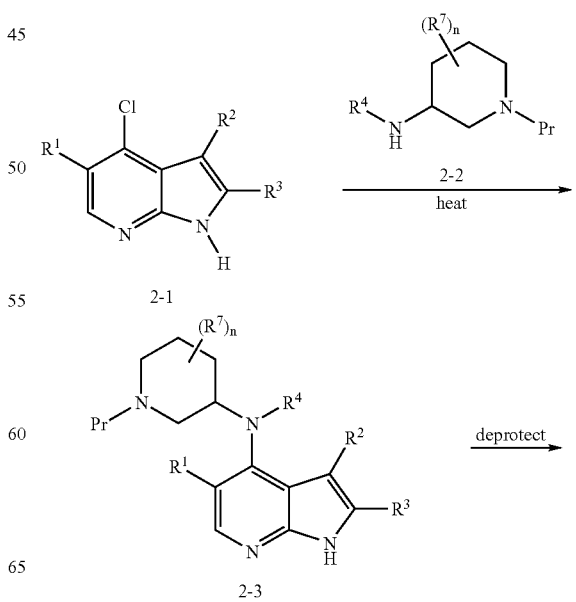

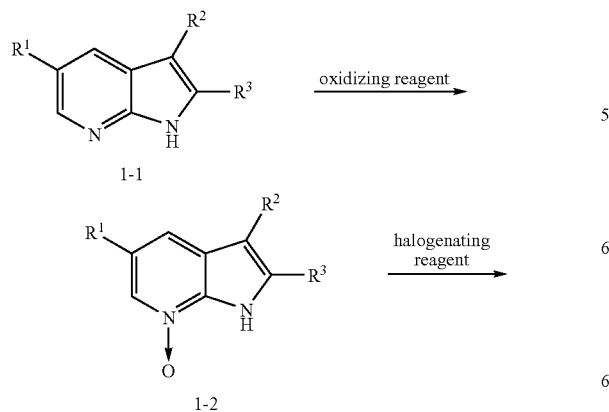

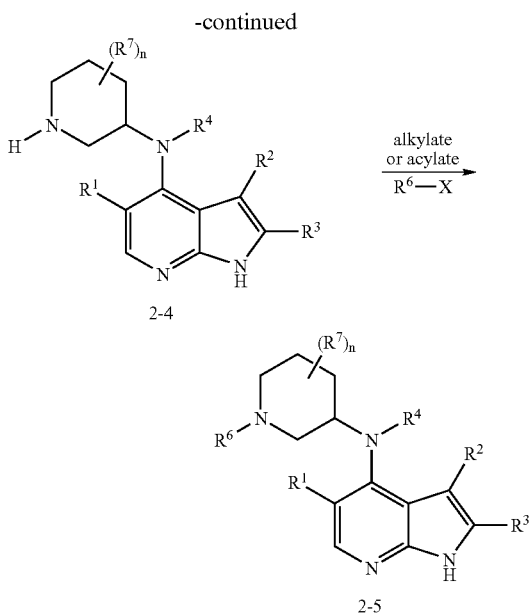

2-4

2-5

Methods for preparing pyrrolo[2,3-d]pyrimidines according to the invention are reported in WO 01/42246, WO 02/00661, and WO 03/48162, each of which is incorporated herein by reference in its entirety.

Methods

Compounds of the invention can modulate activity of one or more Janus kinases (JAKs). The term "modulate" is meant to refer to an ability to increase or decrease the activity of one or more members of the JAK family of kinases. Accordingly, compounds of the invention can be used in methods of modulating a JAK by contacting the JAK with any one or more of the compounds or compositions described herein. In some embodiments, compounds of the present invention can act as inhibitors of one or more JAKs. In some embodiments, compounds of the present invention can act to stimulate the activity of one or more JAKs. In further embodiments, the compounds of the invention can be used to modulate activity of a JAK in an individual in need of modulation of the receptor by administering a modulating amount of a compound of the invention.

JAKs to which the present compounds bind and/or modulate include any member of the JAK family. In some embodiments, the JAK is JAK1, JAK2, JAK3 or TYK2. In some embodiments, the JAK is JAK1 or JAK2. In some embodiments, the JAK is JAK2.

The compounds of the invention can be selective. By "selective" is meant that the compound binds to or inhibits a JAK with greater affinity or potency, respectively, compared to at least one other JAK. In some embodiments, the compounds of the invention are selective inhibitors of JAK1 or JAK2 over JAK3 and/or TYK2. In some embodiments, the compounds of the invention are selective inhibitors of JAK2 (e.g., over JAK1, JAK3 and TYK2). Without wishing to be bound by theory, because inhibitors of JAK3 can lead to immunosuppressive effects, a compound which is selective for JAK2 over JAK3 and which is useful in the treatment of cancer (such as multiple myeloma, for example) can offer the additional advantage of having fewer immunosuppressive side effects. Selectivity can be at least about 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the Km of each enzyme. In some embodiments, selectivity of compounds of the invention for JAK2 over JAK3 can be determined by the cellular ATP concentration.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease). Further examples of JAK-associated diseases include autoimmune diseases such as multiple sclerosis, rheumatoid arthritis, juvenile arthritis, type I diabetes, lupus, psoriasis, inflammatory bowel disease, ulcerative colitis, Crohn's disease, or autoimmune thyroid disorders. Further examples of JAK-associated diseases include allergic conditions such as asthma, food allergies, atopic dermatitis and rhinitis. Further examples of JAK-assoicated diseases include viral diseases such as Epstein Barr Virus (EBV), Hepatitis B, Hepatitis C, HIV, HTLV 1, Varicella-Zoster Virus (VZV) and Human Papilloma Virus (HPV). Futher examples of JAK-associated diseases or conditions include skin disorders such as atopic dermatitis, psoriasis (for example, psoriasis vulgaris), skin sensitization, and the like. Further examples of JAK-associated diseases are those involving IL-6 pathways including Castleman's disease, Kaposi's sarcoma, and others. Futher examples of JAK-associated diseases or conditions include immune reactions (such as diarrhea, skin irritation, skin rash, contact dermatitis or allergic contact sensitization) caused by certain therapeutics in some patients. Further examples of JAK-associated diseases include hyperpropliferative disorders including polycythemia vera, essential thrombocytopenia, myeloid metaplasia with myelofibrosis, and the like. In further embodiments, the JAK-associated disease is cancer such as, for example, prostate, renal, hepatocellular, pancreatic, gastric, breast, lung, cancers of the head and neck, glioblastoma, leukemia, lymphoma or multiple myeloma.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., arresting further development of the pathology and/or symptomatology), and (3) ameliorating the disease; for example, ameliorating a disease, condition or disorder in an individual who is experiencing or displaying the pathology or symptomatology of the disease, condition or disorder (i.e., reversing the pathology and/or symptomatology).

One or more additional pharmaceutical agents such as, for example, chemotherapeutics, anti-inflammatory agents, and/or immunosuppressants can be used in combination with the compounds of the present invention for treatment of JAK-associated diseases, disorders or conditions. For example, a JAK inhibitor used in combination with a chemotherapeutic in the treatment of multiple myeloma may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and velcade. Additive or synergistic effects are desirable outcomes of combining a JAK inhibitor of the present invention with an additional agent. Furthermore, resistance of multiple myeloma cells to agents such as dexamethasome may be reversible upon treatment with a JAK inhibitor of the present invention. The agents can be combined with the present compounds in a single or continuous dosage form, or the agents can be administered simultaneously or sequentially as separate dosage forms.

Pharmaceutical Formulations and Dosage Forms

When employed as pharmaceuticals, the compounds described herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of Formulas I and II above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro metalloprotease labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

The present invention can further include synthetic methods for incorporating radio-isotopes into compounds of the invention. Synthtic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitering its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples have been found to be JAK inhibitors according to at least one biological assay described herein.

EXAMPLES

Example 1

3-{3-[Methyl(1H-pyrrolo[2,3-b]pyridin-4-yl)amino]piperidin-1-yl}-3-oxopropanenitrile

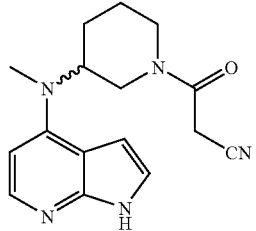

Step 1. 1H-pyrrolo[2,3-b]pyridine 7-oxide

To a 0° C. solution of 1H-pyrrolo[2,3-b]pyridine (4.90 g, 0.0415 mol) in ethyl acetate (41 mL, 0.42 mol) was added a solution of m-chloroperbenzoic acid (m-cpba 9.3 g, 0.054 mol) in ethyl acetate (27 mL, 0.28 mol), and the reaction mixture was solidified when ~20 mL solution of the m-cpba was added. An additional ~10 mL of ethyl acetate was added to facilitate stirring. The reaction was stirred overnight. The reaction mixture was then cooled to 0° C., filtered and washed with ethyl acetate (×3) to give 10.94 g wet solid. To a slurry of 8.45 g of the solid in water (35 mL) was added 13 mL of sat. Na$_2$CO$_3$ dropwise. The resulting mixture was stirred slowly overnight, cooled to 0° C., filtered and washed with water (×4) to give 3.55 g of pale purple solid. The product was dried at 40° C. overnight to give 2.47 g (44.4% yield).

$^1$H NMR (400 MHz, CD$_3$OD): δ 8.2 (1H, d); 7.95 (1H, d); 7.5 (1H, d); 7.2 (1H, m); 6.65 (1H, d). MS (M+H)$^+$: 136.

Step 2: 4-Chloro-1H-pyrrolo[2,3-b]pyridine

To a 50° C. pink solution of 1H-pyrrolo[2,3-b]pyridine 7-oxide (2.47 g, 0.0184 mol) in N,N-dimethylformamide (13.3 mL, 0.172 mol) was added methanesulfonyl chloride (4.0 mL, 0.052 mol). The pink color changed to orange. The mixture was heated to 73° C. for 2 h, and cooled to 40° C. Then 35 mL of water was added and the resulting suspension was cooled to 0° C. NaOH was added to adjust the pH of the mixture to ~7. The mixture was filtered and washed with water (×3) to give 3.8 g of wet pale orange solid that was dried at 40° C. overnight to give 2.35 g (82.2% yield).

$^1$H NMR (400 MHz, CDCl$_3$): δ 10.8 (1H, br); 8.21 (1H, d); 7.41(1H, d); 7.18 (1H, d); 6.61 (1H, d). MS (M+H)$^+$: 153.

Step 3: N-(1-benzylpiperidin-3-yl)-N-methyl-N-(1H-pyrrolo[2,3-b]pyridin-4-yl)-amine

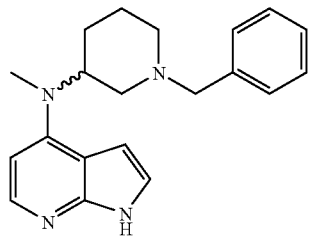

A sealed melted mixture of 4-chloro-1H-pyrrolo[2,3-b]pyridine (0.18 g, 0.0012 mol) in 1-benzyl-N-methylpiperidin-3-amine (0.50 g, 0.0024 mol) was heated to 200° C. overnight. The reaction mixture was partitioned between ethyl acetate (30 mL) and sat. NaHCO$_3$ (20 mL), and the organic phase was washed with sat. NaCl, then dried and was reduced under vacuum to give 500 mg of orange oil. The product was chromatographed with 7% MeOH/DCM, 0.7% NH$_4$OH to give 192 mg of an orange oil (48.8% yield).

$^1$H NMR (400 MHz, CDCl$_3$): δ 7.98 (1H, d); 7.34 (5H, m); 7.08 (1H, d); 6.55 (1H, d); 6.2 (1H, d); 4.15 (1H, t); 3.47 (2H, q); 3.15 (1H); 3.1 (3H, s); 2.9 (1H, d) 2.2-1.6 (6H, m). MS (M+H)$^+$: 322.

Step 4: N-methyl-N-piperidin-3-yl-N-(1H-pyrrolo[2,3-b]pyridin-4-yl)-amine trihydrochloride

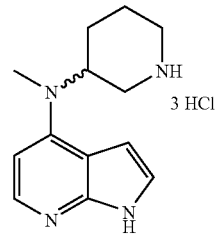

A degassed mixture of N-(1-benzylpiperidin-3-yl)-N-methyl-N-(1H-pyrrolo[2,3-b]pyridin-4-yl)-amine (0.17 g, 0.00053 mol) and palladium hydroxide (0.15 g, 0.00011 mol) in ethanol (3.5 mL, 0.060 mol) and 3.0 M of hydrogen chloride in water (0.40 mL) was stirred under an atmosphere of hydrogen over 2.5 days. The reaction mixture was filtered and washed with MeOH. The filtrate was concentrated under vacuum to give 92 mg of orange oil.

$^1$H NMR (400 MHz, DMSO-d6): δ 12.4 (1H, s);9.39 (2H, br);8.04 (1H, d); 7.4 (1H, d); 6.55 (1H, d); 6.95 (1H, d); 6.89 (1H, d); 4.63 (1H, t); 3.4-1.8 (11H, m). MS (M+H)$^+$: 259.

Step 5: 3-3-[methyl(1H-pyrrolo[2,3-b]pyridin-4-yl)amino]piperidin-1-yl-3-oxopropanenitrile To a solution of N-methyl-N-piperidin-3-yl-N-(1H-pyrrolo[2,3-b]pyridin-4-yl)-amine trihydrochloride (0.092 g, 0.00027 mol) in N,N-dimethylformamide (2 mL, 0.02 mol) were added N,N-diisopropylethylamine (190 μL, 0.0011 mol), cyanoacetic acid (28 mg, 0.00032 mol), 1-hydroxybenzotriazole (36 mg, 0.00027 mol) and N-(3-dimethylaminopropyl)-N'-ethylcarbodiimide hydrochloride (62 mg, 0.00032 mol). The mixture was stirred for 2 h. The reaction mixture was partitioned between ethyl acetate and water and the aqueous phase was extracted with ethyl acetate. The combined organic phases were washed with sat. NaCl, dried and concentrated. The residue was chromatographed with 5-7% MeOH/DCM, 0.5-0.7% NH$_4$OH to give 16 mg of orange solid which was triturated with warm acetonitrile. The resulting solid was filtered and was washed with acetonitrile (×3) to give 9 mg of off-white solid that was dried at 40° C. over the weekend.

$^1$H NMR (400 MHz, DMSO): δ 11.3 (1H, s); 7.85 (1H, d); 7.18 (1H, d); 6.45 (1H, m); 6.32 (1H, m); 4.4 (1H, m); 4.1 (2H, m); 3.9 (1H, br); 3.6 (1H, br); 3.0-2.8 (4H, m) 1.92-1.75 (3H, m); 1.7 (1H, m). MS (M+H)$^+$: 298.

Example 2

3-{(3R,4R)-4-Methyl-3-[methyl(1H-pyrrolo[2,3-b]pyridin-4-yl)amino]piperidin-1-yl}-3-oxopropanenitrile

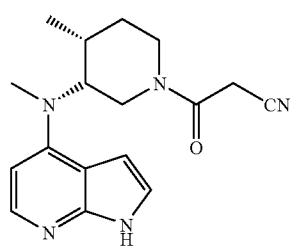

Step 1: 4-Chloro-1-[2-(trimethylsilyl)ethoxy]methyl-1H-pyrrolo[2,3-b]pyridine

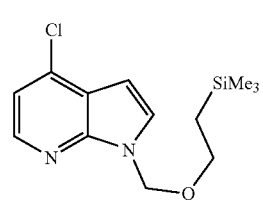

To a 0° C. solution of 4-chloro-1H-pyrrolo[2,3-b]pyridine (0.50 g, 0.0033 mol) and [β-(trimethylsilyl)ethoxy]methyl chloride (0.75 mL, 0.0043 mol) in N,N-dimethylformamide (5 mL, 0.06 mol) was added sodium hydride (0.17 g, 0.0043 mol). The resulting mixture was stirred overnight and partitioned between ethyl acetate and water (×2), and the organic layer was washed with sat. NaCl. The organic layer was then dried under vacuum to produce 1.05 g of an orange oil which was chromatographed with 15% ethyl acetate/hex to give 830 mg of a colorless oil (89.6% yield).

$^1$H NMR (400 MHz, CDCl$_3$): δ 8.29 (1H, d); 7.48 (1H, d); 7.19 (1H, d); 6.7 (1H, d); 5.75 (2H, s); 3.6 (2H, t); 0.98 (2H, t); 0 (9H, s). MS (M+H)$^+$: 283.

Step 2: N-[(3R,4R)-1-benzyl-4-methylpiperidin-3-yl]-N-methyl-1-[2-(trimethylsilyl)-ethoxy]methyl-N-(1H-pyrrolo[2,3-b]pyridin-4-yl)-amine

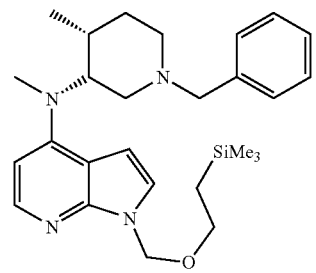

A degassed mixture of (3R,4R)-1-benzyl-N,4-dimethylpiperidin-3-amine (0.210 g, 0.000962 mol), 4-chloro-1-[2-(trimethylsilyl)ethoxy]methyl-1H-pyrrolo[2,3-b]pyridine (0.29 g, 0.0010 mol), tris(dibenzylideneacetone)dipalladium (0) (0.088 g, 0.000096 mol), 0.049 M of tri-tert-butylphosphine in toluene (1.0 mL) and sodium tert-butoxide (0.139 g, 0.00144 mol) in toluene (3 mL, 0.03 mol) was heated to 70° C. for 5 h. After the reaction mixture was cooled to room temperature (rt), ethyl acetate and water were added. The resulting suspension was filtered. The aqueous phase was removed and the remaining organic phase was washed with sat. NaCl, dried, and concentrated under vacuum to give 540 mg orange oil. The crude product was chromatographed using 35% ethyl acetate/hex to give 280 mg orange oil (~1:1 of two isomers). The mixture was chromatographed again with 35% ethyl acetate/hex several times to separate 44 mg of the higher R$_f$ material.

$^1$H NMR (400 MHz, CDCl$_3$): δ 8.15 (1H, d); 7.38 (5H, m); 7.18 (1H, d); 6.6 (1H, d); 6.3 (1H, d); 5.7 (2H, s); 4.58 (1H, t); 3.6 (4H, m); 3.38 (3H, s); 2.86 (1H, br); 2.79 (1H, br); 2.6 (1H, br); 2.55 (1H, br); 2.4 (1H, br); 1.95 (1H, br); 1.77 (1H, br); 1.02 (3H, d); 0.99 (2H, t); 0 (9H, s). MS (M+H)+: 465.

Step 3: N-[(3R,4R)-1-benzyl-4-methylpiperidin-3-yl]-N-methyl-N-(1H-pyrrolo[2,3-b]pyridin-4-yl)-amine

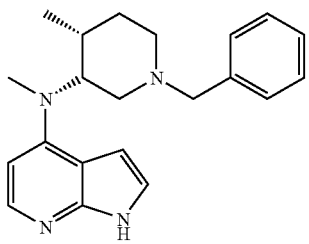

A solution of N-[(3R,4R)-1-benzyl-4-methylpiperidin-3-yl]-N-methyl-1-[2 -(trimethylsilyl)ethoxy]methyl-N-(1H-pyrrolo[2,3-b]pyridin-4-yl)-amine (0.065 g, 0.00014 mol) in trifluoroacetic acid (0.6 mL, 0.008 mol) and methylene chloride (3 mL, 0.05 mol) was stirred overnight. The solvent volume was reduced by roto-vap 3× azeotroped with MeOH. The resulting orange oil was stirred in methanol (1.5 mL, 0.037 mol) and 1.00 M of sodium hydroxide in water (0.5 mL) overnight. Solvents were removed under vacuum and the remaining solid was stirred in ethyl acetate and water. The organic phase was washed with sat. NaCl and the solvent was removed under vacuum to give 37 mg of an orange oil.

$^1$H NMR (400 MHz, CDCl$_3$): δ 8.0 (1H, d); 7.38 (5H, m); 7.1 (1H, d); 6.75 (1H, d); 6.2 (1H, d); 4.58 (1H, t); 3.55 (2H, m); 3.3 (3H, s); 2.8 (1H, br); 2.7 (1H, br); 2.55 (1H, br); 2.45 (1H, br); 2.32 (1H, br); 1.9 (1H, br); 1.65 (1H, br); 1.02 (3H, d). MS (M+H)+: 335.

Step 4: N-methyl-N-[(3R,4R)-4-methylpiperidin-3-yl]-N-(1H-pyrrolo[2,3-b]pyridin-4-yl)-amine

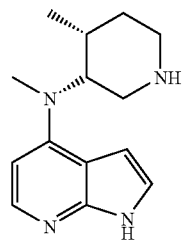

A degassed mixture of N-[(3R,4R)-1-benzyl-4-methylpiperidin-3-yl]-N-methyl-N-(1H-pyrrolo[2,3-b]pyridin-4-yl)-amine (0.030 g, 0.000090 mol) and palladium (0.028 g, 0.000026 mol) in ethanol (2 mL, 0.03 mol) and 3.0 M of hydrogen chloride in water (0.2 mL) was stirred under an atmosphere of hydrogen overnight. The reaction mixture was filtered and washed with MeOH. The solvent was removed under vacuum to give 52 mg of an orange viscous oil. The oil was partitioned between ethyl acetate and sat. NaHCO$_3$. The aqueous phase was extracted with ethyl acetate and THF. The combined organic phases were washed with sat. NaCl. Solvents were removed under vacuume to give 47 mg of an orange solid.

$^1$H NMR (400 MHz, MeOH): δ 7.8 (1H, d); 7.1 (1H, d); 6.6 (1H, d); 6.3 (1H, d); 4.45 (1H, m); 3.7 (1H, m); 3.12 (3H, s); 3.4-1.0 (6H, m); 1.1 (3H, d). MS (M+H)+: 245.

Step 5: 3-{(3R,4R)-4-Methyl-3-[methyl(1H-pyrrolo[2,3-b]pyridin-4-yl)amino]piperidin-1-yl}-3-oxopropanenitrile A mixture of N-methyl-N-[(3R,4R)-4-methylpiperidin-3-yl]-N-(1H-pyrrolo[2,3-b]pyridin-4-yl)-amine (43.0 mg, 0.000176 mol) and 3-[(2,5-dioxopyrrolidin-1-yl)oxy]-3-oxopropanenitrile (38 mg, 0.00021 mol) in ethanol (1 mL, 0.02 mol) was stirred overnight. The reaction mixture was partitioned between ethyl acetate/THF and sat. NaHCO$_3$, and the organic layer was washed by sat. NaCl. The solvent was removed under vacuum to give 100 mg of an orange solid which was chromatographed with 7% MeOH/DCM, 0.7% NH4OH to give 17 mg of pale orange solid. The crude product was triturated with Et$_2$O and the resulting solid was filtered and washed to give 9.4 mg of wet pale orange solid which was dried at from room temperature to about 60° C. for 3.5 h to give 6.5 mg of the final product.

$^1$H NMR (400 MHz, CDCl$_3$): δ 8.15 (1H, d); 7.17 (1H, d); 6.46 (1H, d); 6.3 (1H, d); 4.35 (2H, m); 4.0-3.78 (1H, m); 3.6-3.4 (2H, m); 2.59 (1H, m); 1.99-1.75 (3H, m); 1.15 (3H, d).

MS (M+H)+: 312.

The following additional compounds of the invention in Table 1 were made by methods analogous to those described for Examples 1 and 2.

TABLE 1

| Ex. No. | Structure | Name | (M + 1) |
|---|---|---|---|
| 3 | 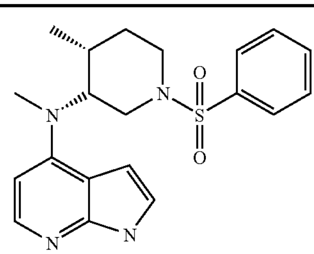 | N-methyl-N-[(3R,4R)-4-methyl-1-(phenylsulfonyl)piperidin-3-yl]-N-(1H-pyrrolo[2,3-b]pyridin-4-yl)-amine | 385.2 |

TABLE 1-continued

| Ex. No. | Structure | Name | (M + 1) |
|---|---|---|---|
| 4 | 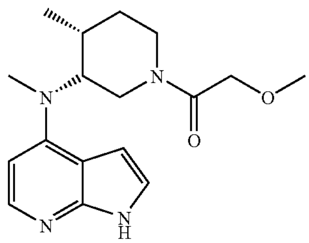 | N-[(3R,4R)-1-(methoxyacetyl)-4-methylpiperidin-3-yl]-N-methyl-N-(1H-pyrrolo[2,3-b]pyridin-4-yl)-amine | 316.2 |
| 5 | 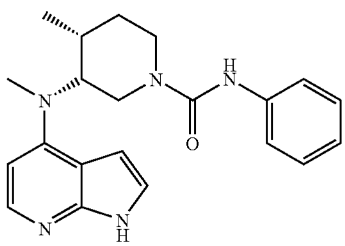 | (3R,4R)-4-methyl-3-[methyl(1H-pyrrolo[2,3-b]pyridin-4-yl)amino]-N-phenylpiperidine-1-carboxamide | 364.2 |
| 6 | 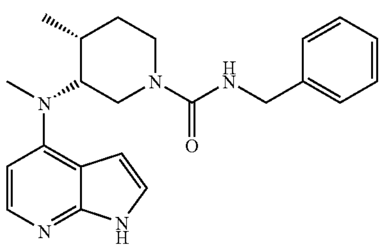 | (3R,4R)-N-benzyl-4-methyl-3-[methyl(1H-pyrrolo[2,3-b]pyridin-4-yl)amino]piperidine-1-carboxamide | 378.2 |
| 7 | 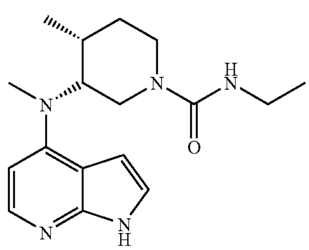 | (3R,4R)-N-ethyl-4-methyl-3-[methyl(1H-pyrrolo[2,3-b]pyridin-4-yl)amino]piperidine-1-carboxamide | 316.2 |
| 8 | 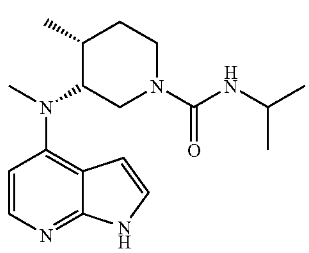 | (3R,4R)-N-isopropyl-4-methyl-3-[methyl(1H-pyrrolo[2,3-b]pyridin-4-yl)amino]piperidine-1-carboxamide | 330.2 |
| 9 | 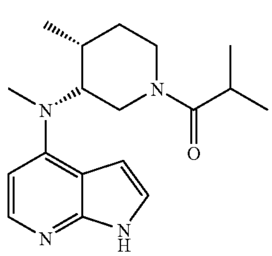 | N-[(3R,4R)-1-isobutyryl-4-methylpiperidin-3-yl]-N-methyl-N-(1H-pyrrolo[2,3-b]pyridin-4-yl)-amine | 315.2 |

TABLE 1-continued

| Ex. No. | Structure | Name | (M + 1) |
|---|---|---|---|
| 10 | 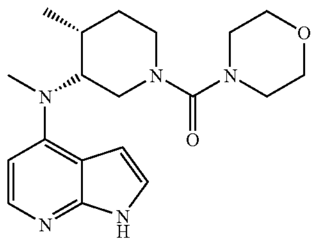 | N-methyl-N-[(3R,4R)-4-methyl-1-(morpholin-4-ylcarbonyl)piperidin-3-yl]-N-(1H-pyrrolo[2,3-b]pyridin-4-yl)-amine | 358.2 |
| 11 | 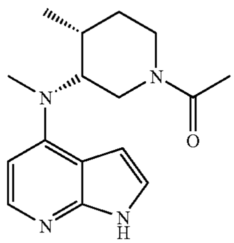 | N-[(3R,4R)-1-acetyl-4-methylpiperidin-3-yl]-N-methyl-N-(1H-pyrrolo[2,3-b]pyridin-4-yl)-amine | 287.2 |
| 12 | 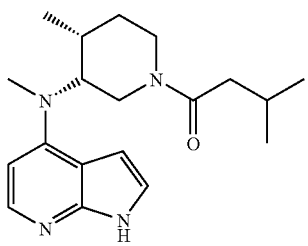 | N-methyl-N-[(3R,4R)-4-methyl-1-(3-methylbutanoyl)piperidin-3-yl]-N-(1H-pyrrolo[2,3-b]pyridin-4-yl)-amine | 329.2 |
| 13 | 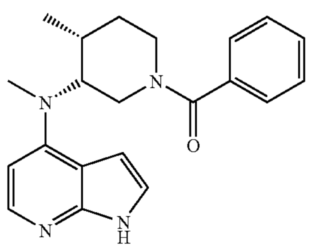 | N-[(3R,4R)-1-benzoyl-4-methylpiperidin-3-yl]-N-methyl-N-(1H-pyrrolo[2,3-b]pyridin-4-yl)-amine | 349.2 |
| 14 | 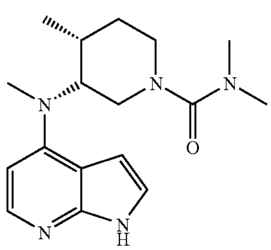 | (3R,4R)-N,N,4-trimethyl-3-[methyl(1H-pyrrolo[2,3-b]pyridin-4-yl)amino]piperidine-1-carboxamide | 316.2 |
| 15 | 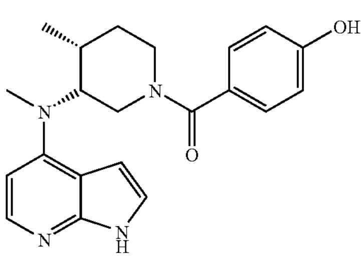 | 4-({(3R,4R)-4-methyl-3-[methyl(1H-pyrrolo[2,3-b]pyridin-4-yl)amino]piperidin-1-yl}carbonyl)benzonitrile | 374.2 |

TABLE 1-continued

| Ex. No. | Structure | Name | (M + 1) |
|---|---|---|---|
| 16 | 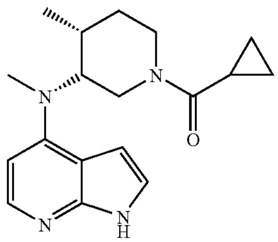 | N-[(3R,4R)-1-(cyclopropylcarbonyl)-4-methylpiperidin-3-yl]-N-methyl-N-(1H-pyrrolo[2,3-b]pyridin-4-yl)-amine | 313.2 |
| 17 | 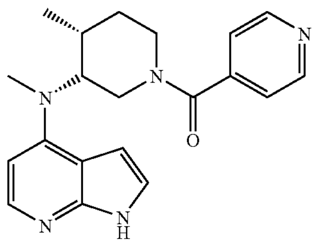 | N-[(3R,4R)-1-isonicotinoyl-4-methylpiperidin-3-yl]-N-methyl-N-(1H-pyrrolo[2,3-b]pyridin-4-yl)-amine | 350.2 |
| 18 | 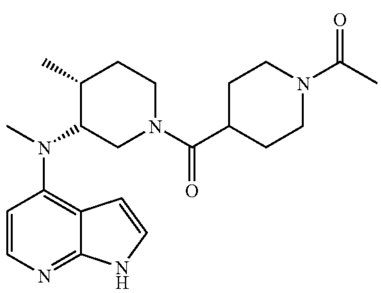 | N-{(3R,4R)-1-[(1-acetylpiperidin-4-yl)carbonyl]-4-methylpiperidin-3-yl}-N-methyl-N-(1H-pyrrolo[2,3-b]pyridin-4-yl)-amine | 398.2 |
| 19 | 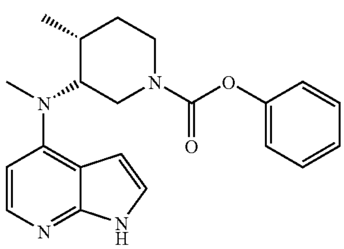 | Phenyl (3R,4R)-4-methyl-3-[methyl(1H-pyrrolo[2,3-b]pyridin-4-yl)amino]piperidine-1-carboxylate | 365.2 |
| 20 | 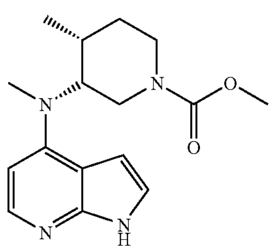 | Methyl (3R,4R)-4-methyl-3-[methyl(1H-pyrrolo[2,3-b]pyridin-4-yl)amino]piperidine-1-carboxylate | 303.2 |
| 21 | 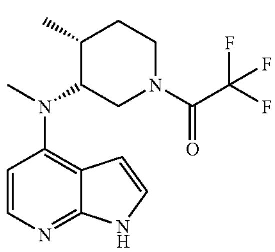 | N-methyl-N-[(3R,4R)-4-methyl-1-(trifluoroacetyl)piperidin-3-yl]-N-(1H-pyrrolo[2,3-b]pyridin-4-yl)-amine | 341.2 |

TABLE 1-continued

| Ex. No. | Structure | Name | (M + 1) |
|---|---|---|---|
| 22 | 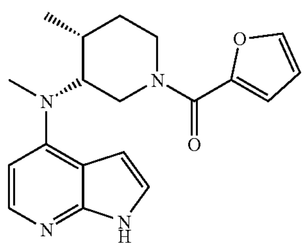 | N-[(3R,4R)-1-(2-furoyl)-4-methylpiperidin-3-yl]-N-methyl-N-(1H-pyrrolo[2,3-b]pyridin-4-yl)-amine | 339.2 |
| 23 | 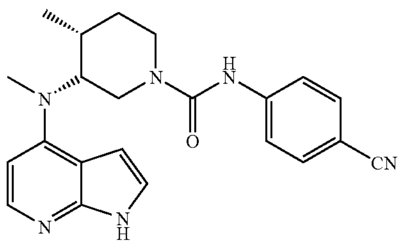 | (3R,4R)-N-(4-cyanophenyl)-4-methyl-3-[methyl(1H-pyrrolo[2,3-b]pyridin-4-yl)amino]piperidine-1-carboxamide | 389.2 |
| 24 | 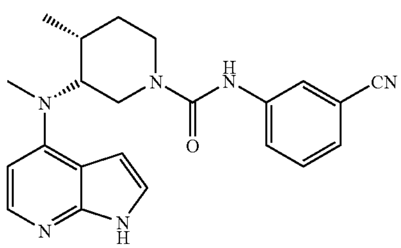 | (3R,4R)-N-(3-cyanophenyl)-4-methyl-3-[methyl(1H-pyrrolo[2,3-b]pyridin-4-yl)amino]piperidine-1-carboxamide | 389.2 |
| 25 | 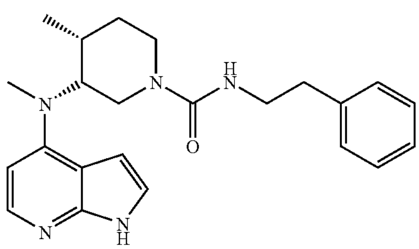 | (3R,4R)-4-methyl-3-[methyl(1H-pyrrolo[2,3-b]pyridin-4-yl)amino]-N-(2-phenylethyl)piperidine-1-carboxamide | 392.2 |
| 26 | 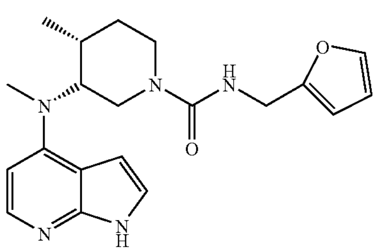 | (3R,4R)-N-(2-furylmethyl)-4-methyl-3-[methyl(1H-pyrrolo[2,3-b]pyridin-4-yl)amino]piperidine-1-carboxamide | 368.2 |
| 27 | 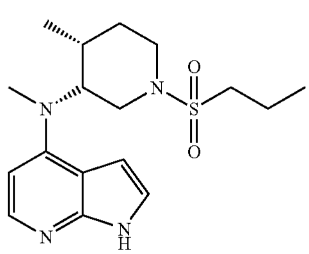 | N-methyl-N-[(3R,4R)-4-methyl-1-(propylsulfonyl)piperidin-3-yl]-N-(1H-pyrrolo[2,3-b]pyridin-4-yl)-amine | 351.2 |

TABLE 1-continued

| Ex. No. | Structure | Name | (M + 1) |
|---|---|---|---|
| 28 | 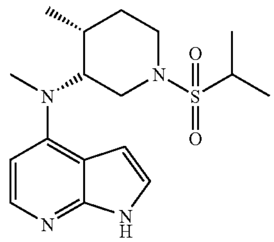 | N-[(3R,4R)-1-(isopropylsulfonyl)-4-methylpiperidin-3-yl]-N-methyl-N-(1H-pyrrolo[2,3-b]pyridin-4-yl)-amine | 351.2 |
| 29 | 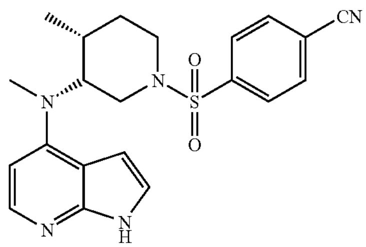 | 4-({(3R,4R)-4-methyl-3-[methyl(1H-pyrrolo[2,3-b]pyridin-4-yl)amino]piperidin-1-yl}sulfonyl)benzonitrile | 410.2 |
| 30 | 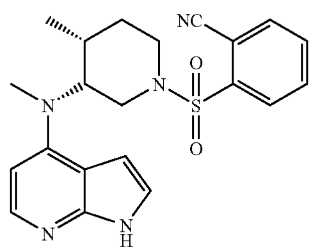 | 2-({(3R,4R)-4-methyl-3-[methyl(1H-pyrrolo[2,3-b]pyridin-4-yl)amino]piperidin-1-yl}sulfonyl)benzonitrile | 410.2 |
| 31 | 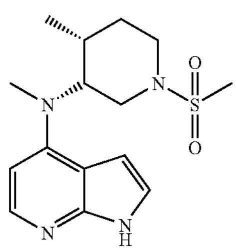 | N-methyl-N-[(3R,4R)-4-methyl-1-(methylsulfonyl)piperidin-3-yl]-N-(1H-pyrrolo[2,3-b]pyridin-4-yl)-amine | 323.2 |
| 32 | 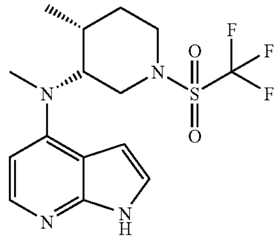 | N-methyl-N-{(3R,4R)-4-methyl-1-[(trifluoromethyl)sulfonyl]piperidin-3-yl}-N-(1H-pyrrolo[2,3-b]pyridin-4-yl)-amine | 377.2 |
| 33 | 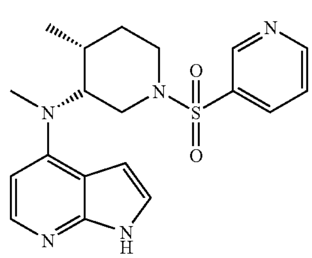 | N-methyl-N-[(3R,4R)-4-methyl-1-(pyridin-3-ylsulfonyl)piperidin-3-yl]-N-(1H-pyrrolo[2,3-b]pyridin-4-yl)-amine | 386.2 |

TABLE 1-continued

| Ex. No. | Structure | Name | (M + 1) |
|---|---|---|---|
| 34 | 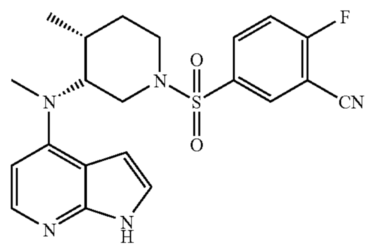 | 2-fluoro-5-({(3R,4R)-4-methyl-3-[methyl(1H-pyrrolo[2,3-b]pyridin-4-yl)amino]piperidin-1-yl}sulfonyl)benzonitrile | 428.2 |
| 35 | 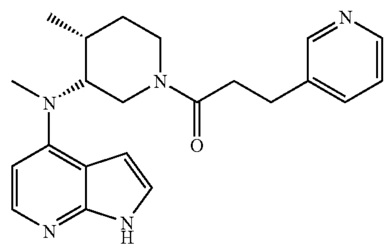 | N-methyl-N-[(3R,4R)-4-methyl-1-(3-pyridin-3-ylpropanoyl)piperidin-3-yl]-N-(1H-pyrrolo[2,3-b]pyridin-4-yl)-amine | 378.2 |
| 36 | 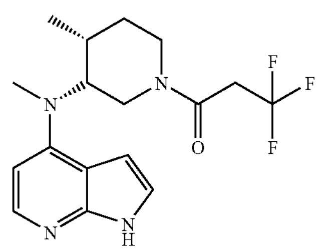 | N-methyl-N-[(3R,4R)-4-methyl-1-(3,3,3-trifluoropropanoyl)piperidin-3-yl]-N-(1H-pyrrolo[2,3-b]pyridin-4-yl)-amine | 355.2 |
| 37 | 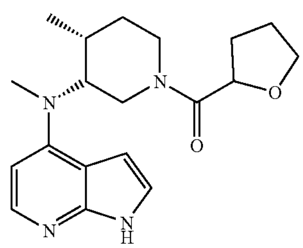 | N-methyl-N-[(3R,4R)-4-methyl-1-(tetrahydrofuran-2-ylcarbonyl)piperidin-3-yl]-N-(1H-pyrrolo[2,3-b]pyridin-4-yl)-amine | 343.2 |
| 38 | 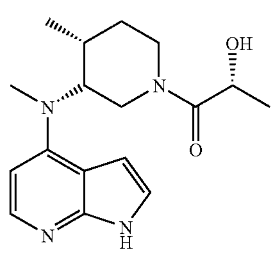 | (2R)-1-{(3R,4R)-4-methyl-3-[methyl(1H-pyrrolo[2,3-b]pyridin-4-yl)amino]piperidin-1-yl}-1-oxopropan-2-ol | 317.2 |
| 39 | 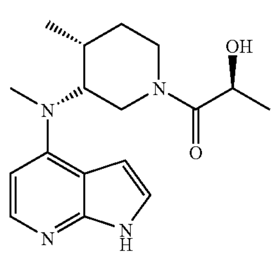 | (2S)-1-{(3R,4R)-4-methyl-3-[methyl(1H-pyrrolo[2,3-b]pyridin-4-yl)amino]piperidin-1-yl}-1-oxopropan-2-ol | 317.2 |

TABLE 1-continued

| Ex. No. | Structure | Name | (M + 1) |
|---|---|---|---|
| 40 | 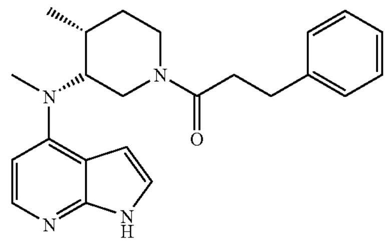 | N-methyl-N-[(3R,4R)-4-methyl-1-(3-phenylpropanoyl)piperidin-3-yl]-N-(1H-pyrrolo[2,3-b]pyridin-4-yl)-amine | 377.2 |
| 41 | 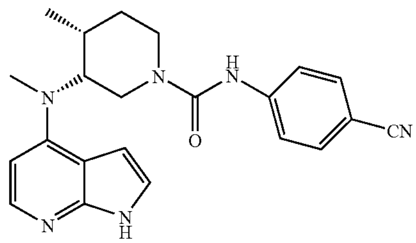 | (3R,4R)-N-(4-cyanophenyl)-4-methyl-3-[methyl(1H-pyrrolo[2,3-b]pyridin-4-yl)amino]piperidine-1-carbothioamide | 405.2 |
| 42 | 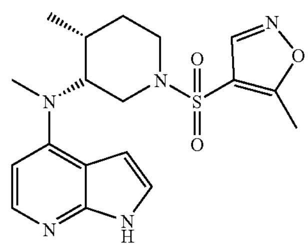 | N-methyl-N-{(3R,4R)-4-methyl-1-[(5-methylisoxazol-4-yl)sulfonyl]piperidin-3-yl}-N-(1H-pyrrolo[2,3-b]pyridin-4-yl)-amine | 390.2 |
| 43 | 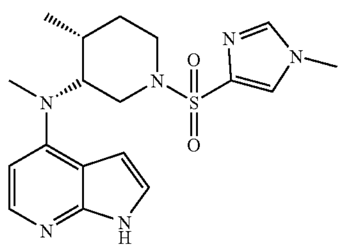 | N-methyl-N-{(3R,4R)-4-methyl-1-[(1-methyl-1H-imidazol-4-yl)sulfonyl]piperidin-3-yl}-N-(1H-pyrrolo[2,3-b]pyridin-4-yl)-amine | 389.2 |
| 44 | 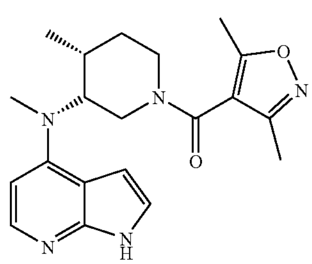 | N-{(3R,4R)-1-[(3,5-dimethylisoxazol-4-yl)carbonyl]-4-methylpiperidin-3-yl}-N-methyl-N-(1H-pyrrolo[2,3-b]pyridin-4-yl)-amine | 368.2 |
| 45 | 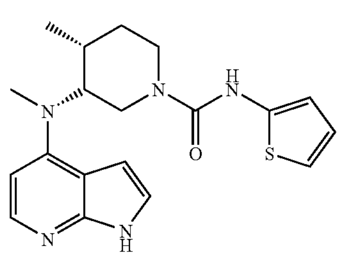 | (3R,4R)-4-methyl-3-[methyl(1H-pyrrolo[2,3-b]pyridin-4-yl)amino]-N-2-thienylpiperidine-1-carboxamide | 370.2 |

TABLE 1-continued

| Ex. No. | Structure | Name | (M + 1) |
|---|---|---|---|
| 46 | 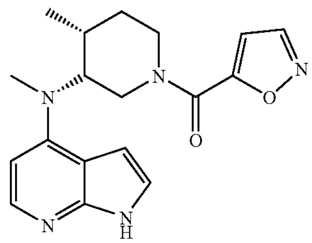 | N-[(3R,4R)-1-(isoxazol-5-ylcarbonyl)-4-methylpiperidin-3-yl]-N-methyl-N-(1H-pyrrolo[2,3-b]pyridin-4-yl)-amine | 340.2 |
| 47 | 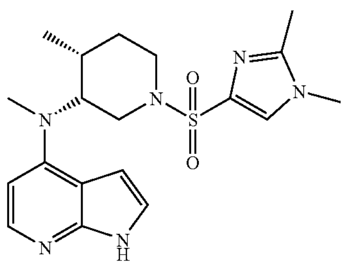 | N-{(3R,4R)-1-[(1,2-dimethyl-1H-imidazol-4-yl)sulfonyl]-4-methylpiperidin-3-yl}-N-methyl-N-(1H-pyrrolo[2,3-b]pyridin-4-yl)-amine | 403.2 |
| 48 | 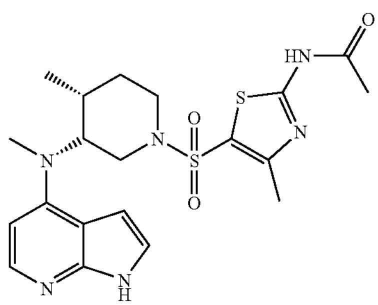 | N-[4-methyl-5-({(3R,4R)-4-methyl-3-[methyl(1H-pyrrolo[2,3-b]pyridin-4-yl)amino]piperidin-1-yl}sulfonyl)-1,3-thiazol-2-yl]acetamide | 463.2 |
| 49 | 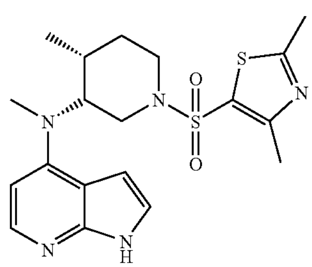 | N-{(3R,4R)-1-[(2,4-dimethyl-1,3-thiazol-5-yl)sulfonyl]-4-methylpiperidin-3-yl}-N-methyl-N-(1H-pyrrolo[2,3-b]pyridin-4-yl)-amine | 420.2 |
| 50 | 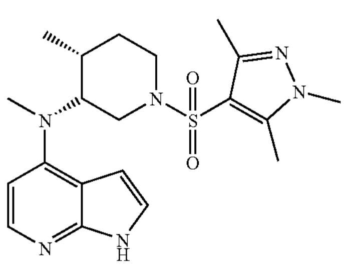 | N-methyl-N-{(3R,4R)-4-methyl-1-[(1,3,5-trimethyl-1H-pyrazol-4-yl)sulfonyl]piperidin-3-yl}-N-(1H-pyrrolo[2,3-b]pyridin-4-yl)-amine | 417.2 |

TABLE 1-continued

| Ex. No. | Structure | Name | (M + 1) |
|---|---|---|---|
| 51 | 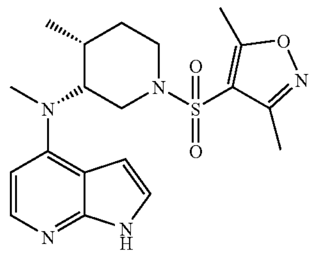 | N-{(3R,4R)-1-[(3,5-dimethylisoxazol-4-yl)sulfonyl]-4-methylpiperidin-3-yl}-N-methyl-N-(1H-pyrrolo[2,3-b]pyridin-4-yl)-amine | 404.2 |
| 52 | 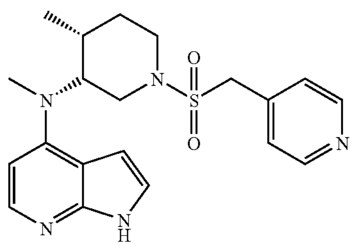 | N-methyl-N-{(3R,4R)-4-methyl-1-[(pyridin-4-ylmethyl)sulfonyl]piperidin-3-yl}-N-(1H-pyrrolo[2,3-b]pyridin-4-yl)-amine | 400.2 |
| 53 | 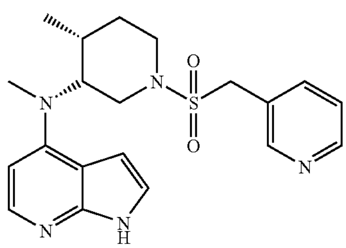 | N-methyl-N-{(3R,4R)-4-methyl-1-[(pyridin-3-ylmethyl)sulfonyl]piperidin-3-yl}-N-(1H-pyrrolo[2,3-b]pyridin-4-yl)-amine | 400.2 |
| 54 | 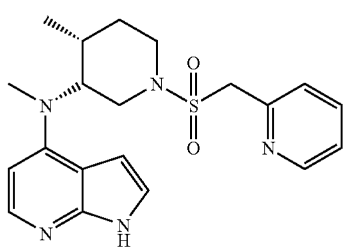 | N-methyl-N-{(3R,4R)-4-methyl-1-[(pyridin-2-ylmethyl)sulfonyl]piperidin-3-yl}-N-(1H-pyrrolo[2,3-b]pyridin-4-yl)-amine | 400.2 |
| 55 | 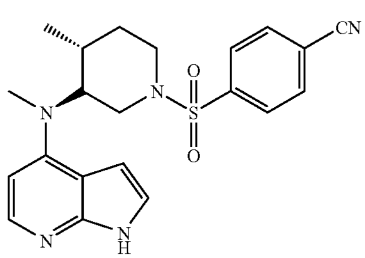 | 4-({(3R,4R)-4-methyl-3-[methyl(1H-pyrrolo[2,3-b]pyridin-4-yl)amino]piperidin-1-yl}sulfonyl)benzonitrile | 410.2 |
| 56 | 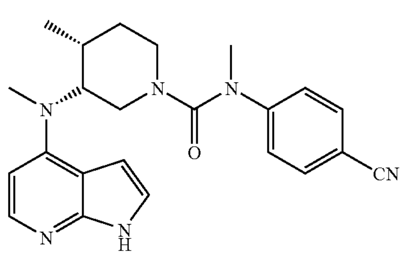 | (3R,4R)-N-(4-cyanophenyl)-N,4-dimethyl-3-[methyl(1H-pyrrolo[2,3-b]pyridin-4-yl)amino]piperidine-1-carboxamide | 403.2 |

TABLE 1-continued

| Ex. No. | Structure | Name | (M + 1) |
|---|---|---|---|
| 57 | 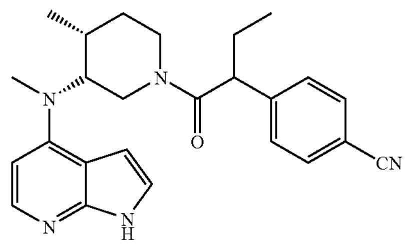 | (3R,4R)-N-(4-cyanophenyl)-N-ethyl-4-methyl-3-[methyl(1H-pyrrolo[2,3-b]pyridin-4-yl)amino]piperidine-1-carboxamide | 417.2 |
| 58 | 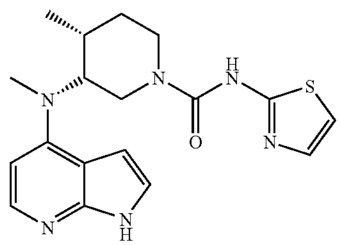 | (3R,4R)-4-methyl-3-[methyl(1H-pyrrolo[2,3-b]pyridin-4-yl)amino]-N-1,3-thiazol-2-ylpiperidine-1-carboxamide | 371.2 |
| 59 | 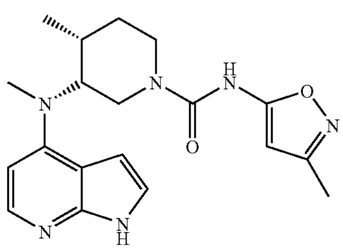 | (3R,4R)-4-methyl-N-(3-methylisoxazol-5-yl)-3-[methyl(1H-pyrrolo[2,3-b]pyridin-4-yl)amino]piperidine-1-carboxamide | 369.2 |
| 60 | 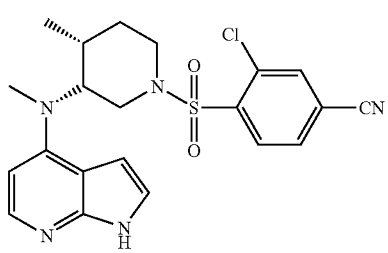 | 3-chloro-4-({(3R,4R)-4-methyl-3-[methyl(1H-pyrrolo[2,3-b]pyridin-4-yl)amino]piperidin-1-yl}sulfonyl)benzonitrile | 444.1 |
| 61 | 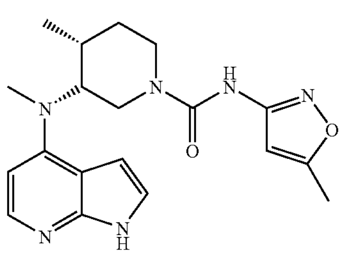 | (3R,4R)-4-methyl-N-(5-methylisoxazol-3-yl)-3-[methyl(1H-pyrrolo[2,3-b]pyridin-4-yl)amino]piperidine-1-carboxamide | 369.2 |

TABLE 1-continued

| Ex. No. | Structure | Name | (M + 1) |
|---|---|---|---|
| 62 | 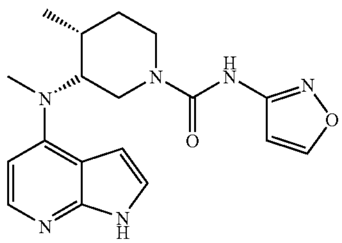 | (3R,4R)-N-isoxazol-3-yl-4-methyl-3-[methyl(1H-pyrrolo[2,3-b]pyridin-4-yl)amino]piperidine-1-carboxamide | 355.2 |
| 63 | 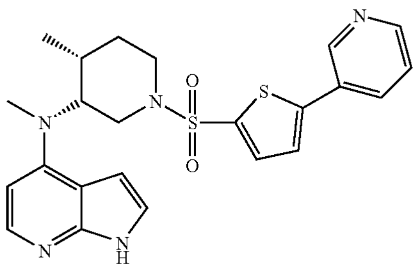 | N-methyl-N-{(3R,4R)-4-methyl-1-[(5-pyridin-3-yl-2-thienyl)sulfonyl]piperidin-3-yl}-N-(1H-pyrrolo[2,3-b]pyridin-4-yl)-amine | 468.2 |
| 64 | 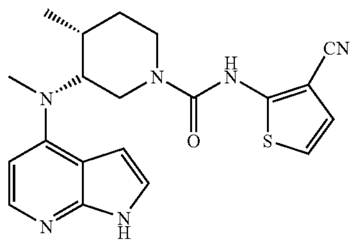 | (3R,4R)-N-(3-cyano-2-thienyl)-4-methyl-3-[methyl(1H-pyrrolo[2,3-b]pyridin-4-yl)amino]piperidine-1-carboxamide | 395.2 |
| 65 | 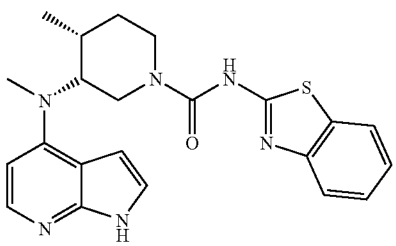 | (3R,4R)-N-1,3-benzothiazol-2-yl-4-methyl-3-[methyl(1H-pyrrolo[2,3-b]pyridin-4-yl)amino]piperidine-1-carboxamide | 421.2 |
| 66 | 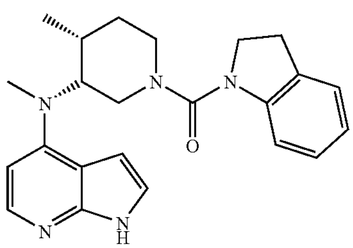 | N-[(3R,4R)-1-(2,3-dihydro-1H-indol-1-ylcarbonyl)-4-methylpiperidin-3-yl]-N-methyl-N-(1H-pyrrolo[2,3-b]pyridin-4-yl)-amine | 390.2 |
| 67 | 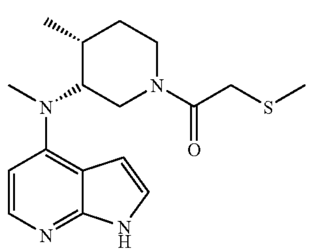 | N-methyl-N-{(3R,4R)-4-methyl-1-[(methylthio)acetyl]piperidin-3-yl}-N-(1H-pyrrolo[2,3-b]pyridin-4-yl)-amine | 333.2 |

TABLE 1-continued

| Ex. No. | Structure | Name | (M + 1) |
|---|---|---|---|
| 68 | 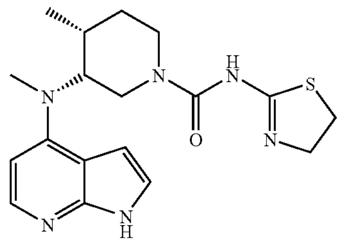 | (3R,4R)-N-(4,5-dihydro-1,3-thiazol-2-yl)-4-methyl-3-[methyl(1H-pyrrolo[2,3-b]pyridin-4-yl)amino]piperidine-1-carboxamide | 373.2 |
| 69 | 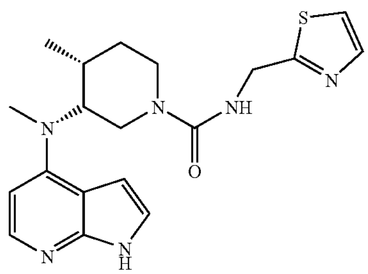 | (3R,4R)-4-methyl-3-[methyl(1H-pyrrolo[2,3-b]pyridin-4-yl)amino]-N-(1,3-thiazol-2-ylmethyl)piperidine-1-carboxamide | 385.2 |
| 70 | 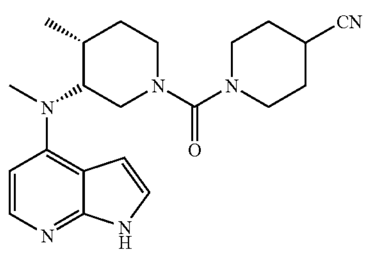 | 1-({(3R,4R)-4-methyl-3-[methyl(1H-pyrrolo[2,3-b]pyridin-4-yl)amino]piperidin-1-yl}carbonyl)piperidine-4-carbonitrile | 381.2 |
| 71 | 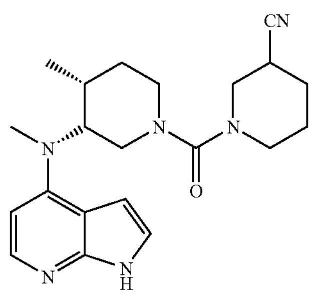 | 1-({(3R,4R)-4-methyl-3-[methyl(1H-pyrrolo[2,3-b]pyridin-4-yl)amino]piperidin-1-yl}carbonyl)piperidine-3-carbonitrile | 381.2 |
| 72 | 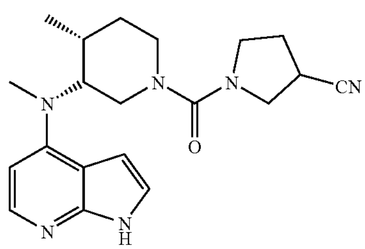 | 1-({(3R,4R)-4-methyl-3-[methyl(1H-pyrrolo[2,3-b]pyridin-4-yl)amino]piperidin-1-yl}carbonyl)pyrrolidine-3-carbonitrile | 384.2 |
| 73 | 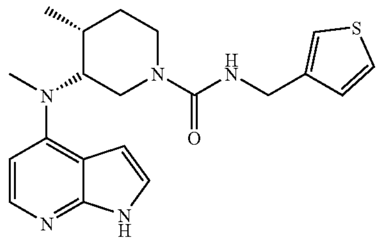 | (3R,4R)-4-methyl-3-[methyl(1H-pyrrolo[2,3-b]pyridin-4-yl)amino]-N-(3-thienylmethyl)piperidine-1-carboxamide | 384.2 |

TABLE 1-continued

| Ex. No. | Structure | Name | (M + 1) |
|---|---|---|---|
| 74 | 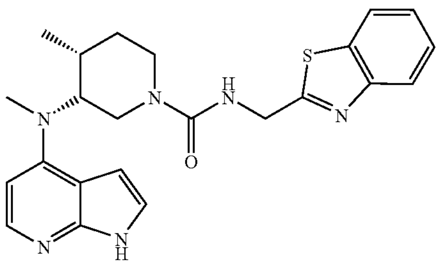 | (3R,4R)-N-(2-benzothien-1-ylmethyl)-4-methyl-3-[methyl(1H-pyrrolo[2,3-b]pyridin-4-yl)amino]piperidine-1-carboxamide | 434.2 |
| 75 | 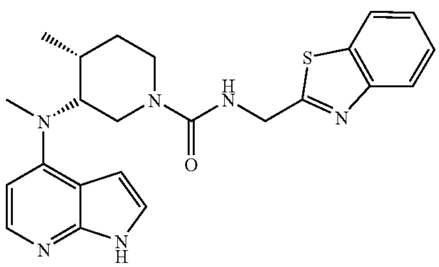 | (3R,4R)-N-(1,3-benzothiazol-2-ylmethyl)-4-methyl-3-[methyl(1H-pyrrolo[2,3-b]pyridin-4-yl)amino]piperidine-1-carboxamide | 435.2 |
| 76 | 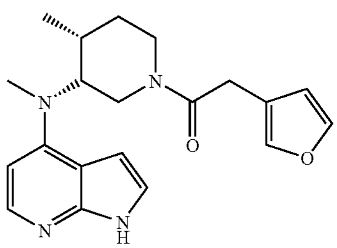 | N-[(3R,4R)-1-(3-furylacetyl)-4-methylpiperidin-3-yl]-N-methyl-N-(1H-pyrrolo[2,3-b]pyridin-4-yl)-amine | 353.2 |
| 77 | 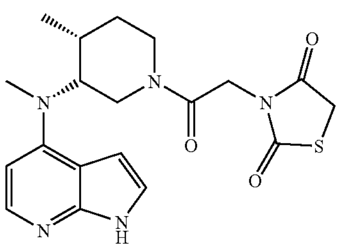 | 3-(2-{(3R,4R)-4-methyl-3-[methyl(1H-pyrrolo[2,3-b]pyridin-4-yl)amino]piperidin-1-yl}-2-oxoethyl)-1,3-thiazolidine-2,4-dione | 402.2 |
| 78 | 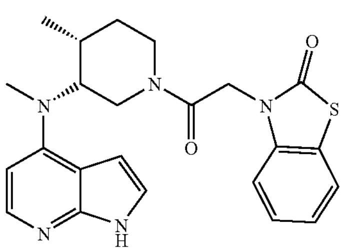 | 3-(2-{(3R,4R)-4-methyl-3-[methyl(1H-pyrrolo[2,3-b]pyridin-4-yl)amino]piperidin-1-yl}-2-oxoethyl)-1,3-benzothiazol-2(3H)-one | 436.2 |
| 79 | 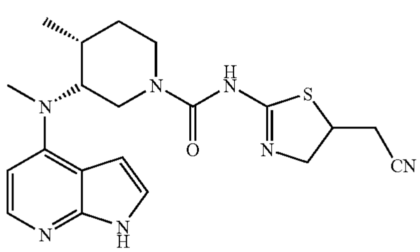 | (3R,4R)-N-[5-(cyanomethyl)-4,5-dihydro-1,3-thiazol-2-yl]-3-[methyl-(1H-pyrrolo[2,3-b]pyridin-4-yl)amino]-4-methyl-piperidine-1-carboxamide | 412.2 |

TABLE 1-continued

| Ex. No. | Structure | Name | (M + 1) |
|---|---|---|---|
| 80 | 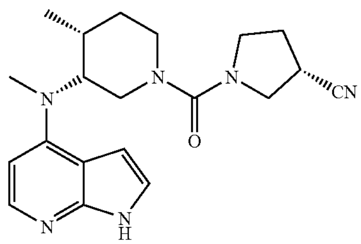 | (3S)-1-({(3R,4R)-4-methyl-3-[methyl(1H-pyrrolo[2,3-b]pyridin-4-yl)amino]piperidin-1-yl}carbonyl)pyrrolidine-3-carbonitrile | 367.2 |
| 81 | 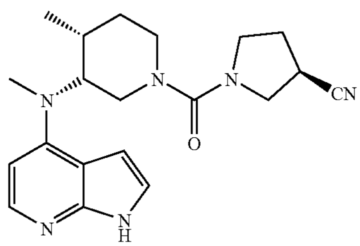 | (3R)-1-({(3R,4R)-4-methyl-3-[methyl(1H-pyrrolo[2,3-b]pyridin-4-yl)amino]piperidin-1-yl}carbonyl)pyrrolidine-3-carbonitrile | 367.2 |
| 82 | 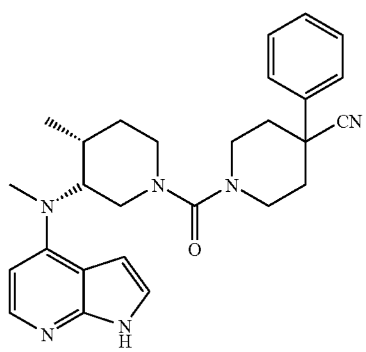 | 1-({(3R,4R)-4-methyl-3-[methyl(1H-pyrrolo[2,3-b]pyridin-4-yl)amino]piperidin-1-yl}carbonyl)-4-phenylpiperidine-4-carbonitrile | 457.2 |
| 83 | 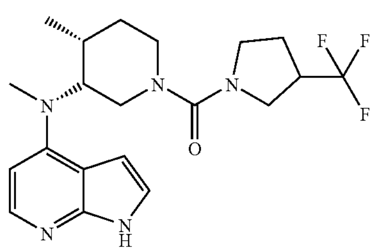 | N-methyl-N-((3R,4R)-4-methyl-1-{[3-(trifluoromethyl)pyrrolidin-1-yl]carbonyl}piperidin-3-yl)-N-(1H-pyrrolo[2,3-b]pyridin-4-yl)-amine | 410.2 |
| 84 | 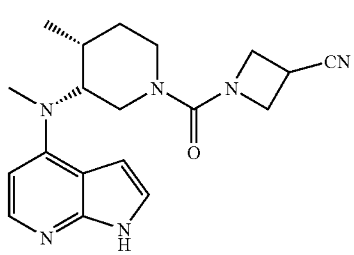 | 1-({(3R,4R)-4-methyl-3-[methyl(1H-pyrrolo[2,3-b]pyridin-4-yl)amino]piperidin-1-yl}carbonyl)azetidine-3-carbonitrile | 353.2 |

| Ex. No. | Structure | Name | (M + 1) |
|---|---|---|---|
| 85 | 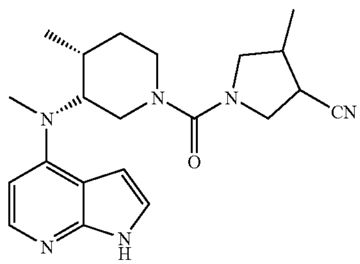 | 4-methyl-1-({(3R,4R)-4-methyl-3-[methyl(1H-pyrrolo[2,3-b]pyridin-4-yl)amino]piperidin-1-yl}carbonyl)pyrrolidine-3-carbonitrile | 381.2 |
| 86 | 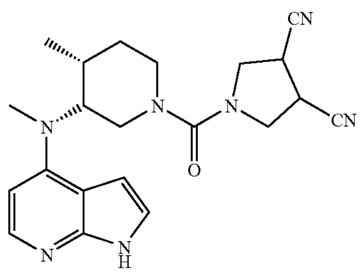 | 1-({(3R,4R)-4-methyl-3-[methyl(1H-pyrrolo[2,3-b]pyridin-4-yl)amino]piperidin-1-yl}carbonyl)pyrrolidine-3,4-dicarbonitrile | 392.2 |
| 87 | 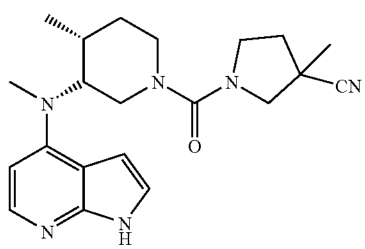 | 3-methyl-1-({(3R,4R)-4-methyl-3-[methyl(1H-pyrrolo[2,3-b]pyridin-4-yl)amino]piperidin-1-yl}carbonyl)pyrrolidine-3-carbonitrile | 381.2 |
| 88 | 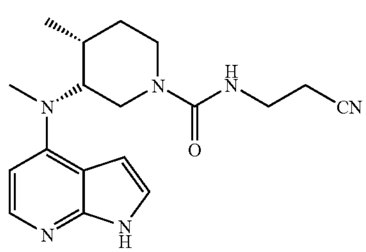 | (3R,4R)-N-(2-cyanoethyl)-4-methyl-3-[methyl(1H-pyrrolo[2,3-b]pyridin-4-yl)amino]piperidine-1-carboxamide | 341.2 |
| 89 | 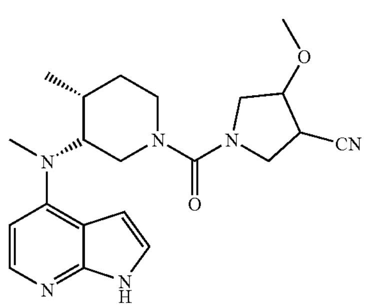 | 4-methoxy-1-({(3R,4R)-4-methyl-3-[methyl(1H-pyrrolo[2,3-b]pyridin-4-yl)amino]piperidin-1-yl}carbonyl)pyrrolidine-3-carbonitrile | 397.2 |

TABLE 1-continued

| Ex. No. | Name | (M + 1) |
|---|---|---|
| 90 | N-{(3R,4R)-1-[(2R)-2-aminopropanoyl]-4-methylpiperidin-3-yl}-N-methyl-N-(1H-pyrrolo[2,3-b]pyridin-4-yl)-amine | 316.1 |
| 91 | N-[(3R,4R)-1-(aminoacetyl)-4-methylpiperidin-3-yl]-N-methyl-N-(1H-pyrrolo[2,3-b]pyridin-4-yl)-amine | 302.1 |
| 92 | 1-(2-{(3R,4R)-4-methyl-3-[methyl(1H-pyrrolo[2,3-b]pyridin-4-yl)amino]piperidin-1-yl}-2-oxoethyl)piperidine-4-carbonitrile | 395.1 |
| 93 | N-methyl-N-[(3R,4R)-4-methyl-1-(1,3-thiazol-4-ylcarbonyl)piperidin-3-yl]-N-(1H-pyrrolo[2,3-b]pyridin-4-yl)-amine bis(trifluoroacetate) | 356.1 |
| 94 | 4-(2-2S-{[methyl-(1H-pyrrolo[2,3-b]pyridin-4-yl)-amino]-methyl}-pyrrolidin-1-yl-sulfonyl)-benzonitrile trifluoroacetate | 396.1 |

TABLE 1-continued

| Ex. No. | Structure | Name | (M + 1) |
|---|---|---|---|
| 95 | 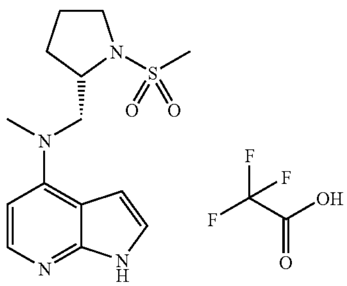 | N-[(1-methanesulfonyl-2S-pyrrolidin-2-yl)-methyl]-N-methyl-N-(1H-pyrrolo[2,3-b]pyridin-4-yl)-amine trifluoroacetate | 309.1 |
| 96 | 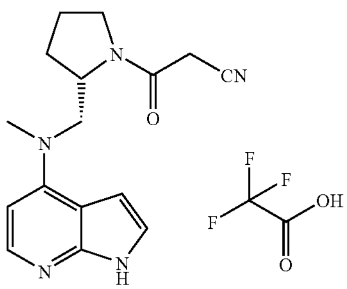 | 3-((2S)-2-{[methyl(1H-pyrrolo[2,3-b]pyridin-4-yl)amino]methyl}pyrrolidin-1-yl)-3-oxopropanenitrile trifluoroacetate | 298.1 |
| 97 | 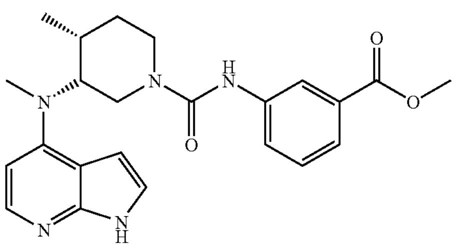 | Methyl 3-[({(3R,4R)-4-methyl-3-[methyl(1H-pyrrolo[2,3-b]pyridin-4-yl)amino]piperidine-1-yl}carbonyl)-amino]benzoate | 422.1 |
| 98 | 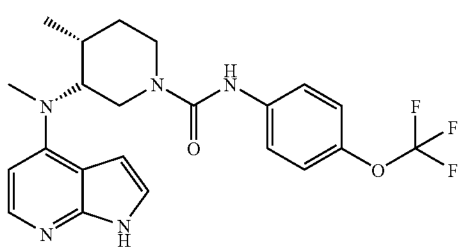 | (3R,4R)-N-(4-trifluoromethoxyphenyl)-4-methyl-3-[methyl-(1H-pyrrolo[2,3-b]pyridin-4-yl)amino]piperidine-1-carboxamide | 448.1 |
| 99 | 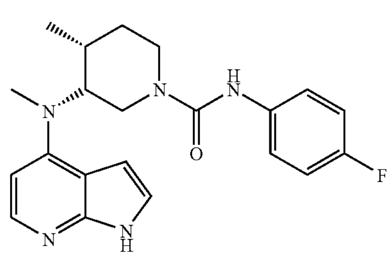 | (3R,4R)-N-(4-fluorophenyl)-4-methyl-3-[methyl-(1H-pyrrolo[2,3-b]pyridin-4-yl)amino]piperidine-1-carboxamide | 382.1 |

TABLE 1-continued

| Ex. No. | Structure | Name | (M + 1) |
|---|---|---|---|
| 100 | 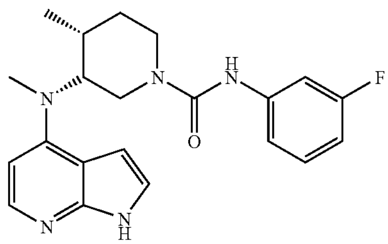 | (3R,4R)-N-(3-fluorophenyl)-4-methyl-3-[methyl-(1H-pyrrolo[2,3-b]pyridin-4-yl)amino]piperidine-1-carboxamide | 382.1 |
| 101 | 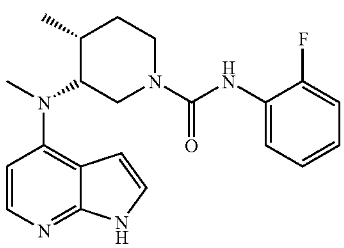 | (3R,4R)-N-(2-fluorophenyl)-4-methyl-3-[methyl-(1H-pyrrolo[2,3-b]pyridin-4-yl)amino]piperidine-1-carboxamide | 382.1 |
| 102 | 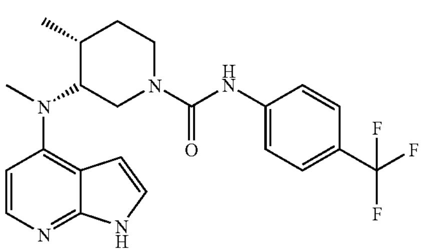 | (3R,4R)-N-(4-trifluoromethylphenyl)-4-methyl-3-[methyl-(1H-pyrrolo[2,3-b]pyridin-4-yl)amino]piperidine-1-carboxamide | 432.1 |
| 103 | 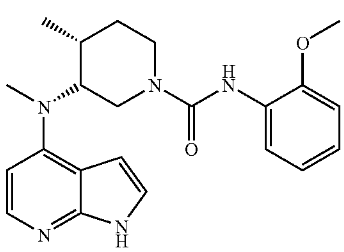 | (3R,4R)-N-(2-methoxyphenyl)-4-methyl-3-[methyl(1H-pyrrolo[2,3-b]pyridin-4-yl)amino]piperidine-1-carboxamide | 394.1 |
| 104 | 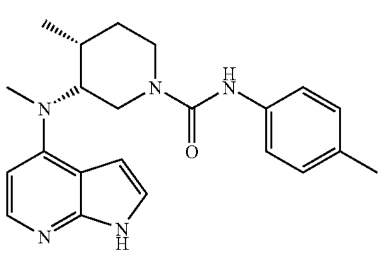 | (3R,4R)-4-methyl-N-(4-methylphenyl)-3-[methyl(1H-pyrrolo[2,3-b]pyridin-4-yl)-amino]piperidine-1-carboxamide | 378.1 |

TABLE 1-continued

| Ex. No. | Structure | Name | (M + 1) |
|---|---|---|---|
| 105 | 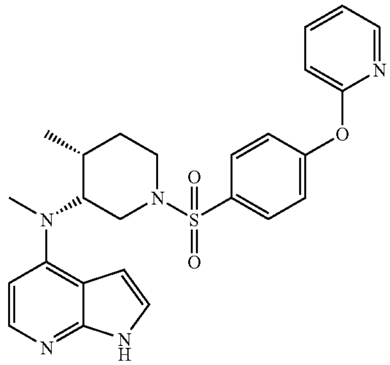 | N-methyl-N-{(3R,4R)-4-methyl-1-[4-(pyridin-2-yloxy)phenyl]sulfonyl-piperidin-3-yl}-N-(1H-pyrrolo[2,3-b]pyridin-4-yl)-amine | 478.1 |
| 106 | 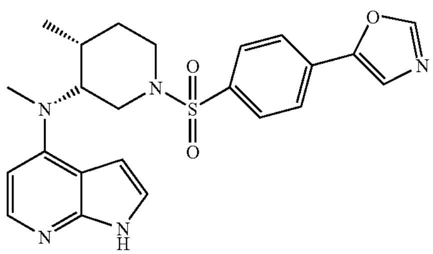 | N-methyl-N-{(3R,4R)-4-methyl-1-[4-(1,3-oxazol-5-yl)phenyl]sulfonyl-piperidin-3-yl}-N-(1H-pyrrolo[2,3-b]pyridin-4-yl)-amine | 452.1 |
| 107 | 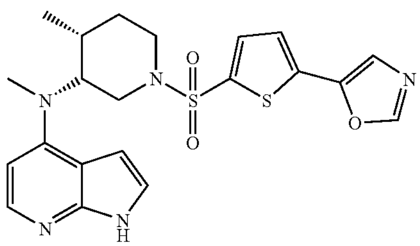 | N-methyl-N-{(3R,4R)-4-methyl-1-[5-(1,3-oxazol-5-yl)thienyl]sulfonyl-piperidin-3-yl}-N-(1H-pyrrolo[2,3-b]pyridin-4-yl)-amine | 458.1 |
| 108 | 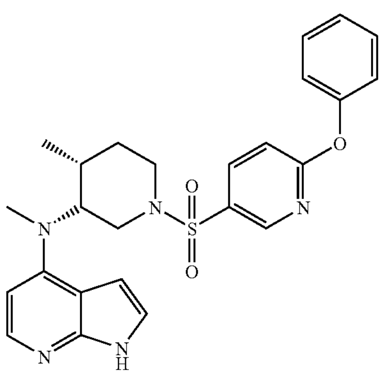 | N-methyl-N-{(3R,4R)-4-methyl-1-[(6-phenoxy-pyridin-3-yl)sulfonyl]piperidin-3-yl}-N-(1H-pyrrolo[2,3-b]pyridin-4-yl)-amine | 478.1 |
| 109 | 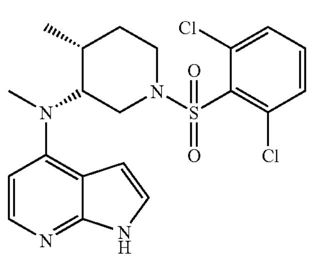 | N-{(3R,4R)-1-[(2,6-dichlorophenyl)sulfonyl]-4-methylpiperidin-3-yl}-N-methyl-N-(1H-pyrrolo[2,3-b]pyridin-4-yl)-amine | 453.1 |

TABLE 1-continued

| Ex. No. | Structure | Name | (M + 1) |
|---|---|---|---|
| 110 | 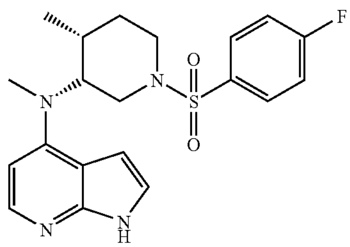 | N-{(3R,4R)-1-[(4-fluorophenyl)sulfonyl]-4-methylpiperidin-3-yl}-N-methyl-N-(1H-pyrrolo[2,3-b]pyridin-4-yl)-amine | 403.1 |
| 111 | 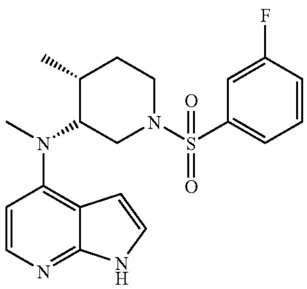 | N-{(3R,4R)-1-[(3-fluorophenyl)sulfonyl]-4-methylpiperidin-3-yl}-N-methyl-N-(1H-pyrrolo[2,3-b]pyridin-4-yl)-amine | 403.1 |
| 112 | 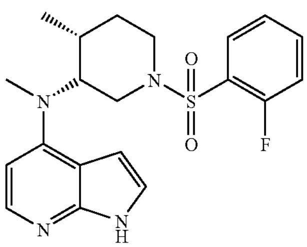 | N-{(3R,4R)-1-[(2-fluorophenyl)sulfonyl]-4-methylpiperidin-3-yl}-N-methyl-N-(1H-pyrrolo[2,3-b]pyridin-4-yl)-amine | 403.1 |
| 113 | 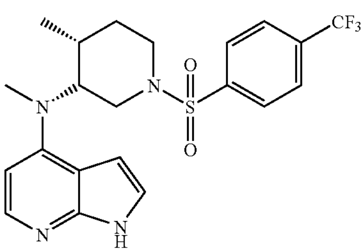 | N-{(3R,4R)-4-methyl-1-[4-(trifluoromethyl)phenyl]sulfonyl-piperidin-3-yl}-N-(1H-pyrrolo[2,3-b]pyridin-4-yl)-amine | 453.1 |
| 114 | 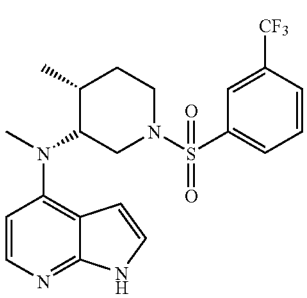 | N-{(3R,4R)-4-methyl-1-[3-(trifluoromethyl)phenyl]sulfonyl-piperidin-3-yl}-N-(1H-pyrrolo[2,3-b]pyridin-4-yl)-amine | 453.1 |

TABLE 1-continued

| Ex. No. | Structure | Name | (M + 1) |
|---|---|---|---|
| 115 | 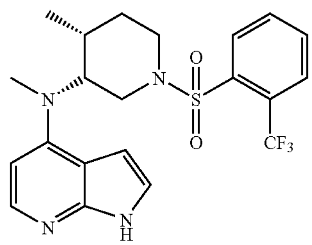 | N-{(3R,4R)-4-methyl-1-[2-(trifluoromethyl)phenyl]sulfonyl-piperidin-3-yl}-N-(1H-pyrrolo[2,3-b]pyridin-4-yl)-amine | 453.1 |
| 116 | 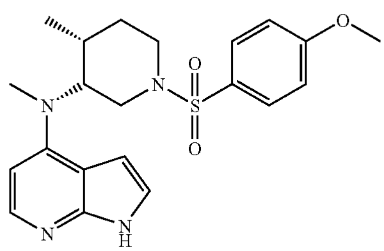 | N-{(3R,4R)-1-[(4-methoxyphenyl)sulfonyl]-4-methylpiperidin-3-yl}-N-methyl-N-(1H-pyrrolo[2,3-b]pyridin-4-yl)-amine | 415.1 |
| 117 | 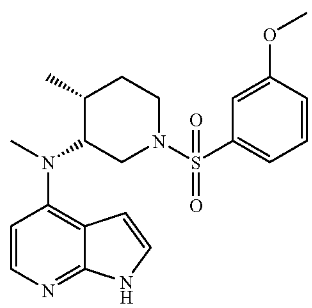 | N-{(3R,4R)-1-[(3-methoxyphenyl)sulfonyl]-4-methylpiperidin-3-yl}-N-methyl-N-(1H-pyrrolo[2,3-b]pyridin-4-yl)-amine | 415.1 |
| 118 | 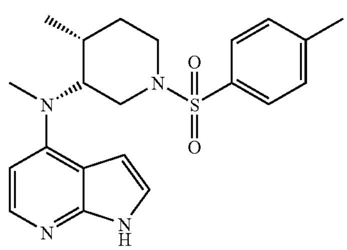 | N-methyl-N-{(3R,4R)-4-methyl-1-[(4-methylphenyl)sulfonyl]piperidin-3-yl}-N-(1H-pyrrolo[2,3-b]pyridin-4-yl)-amine | 399.1 |
| 119 | 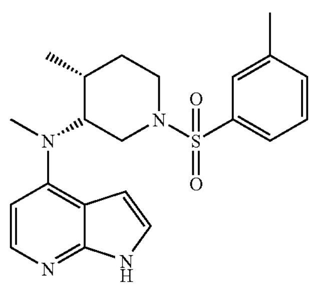 | N-methyl-N-{(3R,4R)-4-methyl-1-[(3-methylphenyl)sulfonyl]piperidin-3-yl}-N-(1H-pyrrolo[2,3-b]pyridin-4-yl)-amine | 399.1 |

TABLE 1-continued

| Ex. No. | Structure | Name | (M + 1) |
|---|---|---|---|
| 120 | 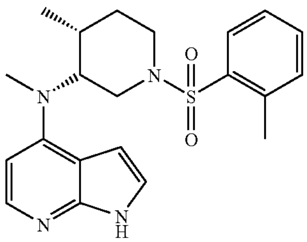 | N-methyl-N-{(3R,4R)-4-methyl-1-[(2-methylphenyl)sulfonyl]piperidin-3-yl}-N-(1H-pyrrolo[2,3-b]pyridin-4-yl)-amine | 399.1 |
| 121 | 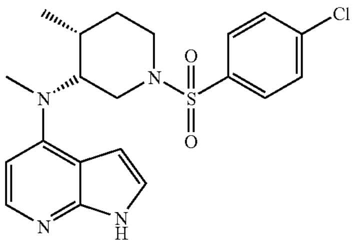 | N-{(3R,4R)-1-[(4-chlorophenyl)sulfonyl]-4-methylpiperidin-3-yl}-N-methyl-N-(1H-pyrrolo[2,3-b]pyridin-4-yl)-amine | 419.1 |
| 122 | 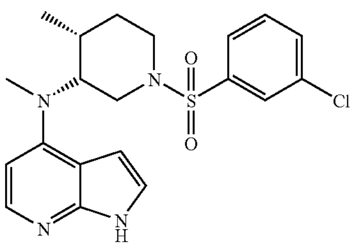 | N-{(3R,4R)-1-[(3-chlorophenyl)sulfonyl]-4-methylpiperidin-3-yl}-N-methyl-N-(1H-pyrrolo[2,3-b]pyridin-4-yl)-amine | 419.1 |
| 123 | 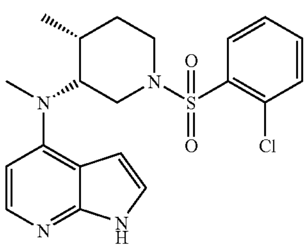 | N-{(3R,4R)-1-[(2-chlorophenyl)sulfonyl]-4-methylpiperidin-3-yl}-N-methyl-N-(1H-pyrrolo[2,3-b]pyridin-4-yl)-amine | 419.1 |

Example A

In Vitro JAK Assay

Compounds herein were tested for inhibitory activity of Jak targets according to the following in vitro assay described in Park et al., *Analytical Biochemistry* 1999, 269, 94-104. The catalytic domains of human Jak1 (a.a. 837-1142), Jak2 (a.a. 828-1132) and Jak3 (a.a. 781-1124) with an N-terminal His tag were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the reactions that contain the enzyme, ATP and 500 nM peptide in 50 mM Tris (pH 7.8) buffer with 100 mM NaCl, 5 mM DTT, and 0.1 mg/ml (0.01%) BSA. The ATP concentration in the reactions was 90 µM for Jak1, 30 µM for Jak2 and 3 µM for Jak3. Reactions were carried out at room temperature for 1 hr and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). Compounds having an $IC_{50}$ of 10 µM or less for any of the above-mentioned Jak targets were considered active.

Example B

Murine DTH Model for Dermatitis

Model

Certain compounds herein were also tested for their efficacies (of inhibiting Jak targets) in the T-cell driven murine delayed hypersysitivity test model. The murine skin contact delayed-type hypersensitivity (DTH) response is considered to be a valid model of clinical contact dermatitis, and other T-lymphocyte mediated immune disorders of the skin, such as psoriasis (Immunol Today. 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

Systemic Administration

Test compound 3-{(3R,4R)-4-methyl-3-[methyl-(7H-pyrrolo[2,3-d]pyrimidin-4-yl)amino]-piperidin-1-yl}-3-oxo-propionitrile (see, e.g., WO 01/42246, WO 02/00661, or WO 03/48162) was administered continuously using mini-osmotic pumps to deliver the compound at 150 mg/kg/d. The inflammatory response was monitored by measuring the ear thickness prior to and after immune challenge. Differences in ear thickness were calculated for each mouse and then averaged for the group. Comparisons were made between vehicle and the treated groups in the context of the negative controls (challenged without sensitization) and therapeutic positive control mice (treated with dexamethasone or other efficacious agent). The test compound inhibited ear swelling by 95% and histological analysis of hematoxolyin and eosin stained tissue sections confirmed a near complete inhibition of ear swelling.

Topical Administration

A further murine DTH experiment was conducted by treating mice with 3-{(3R,4R)-4-methyl-3-[methyl-(7H-pyrrolo[2,3-d]pyrimidin-4-yl)amino]-piperidin-1-yl}-3-oxo-propionitrile either systemically or topically (3%, BID) after the sensitization phase was complete. As was observed with systemic administration during both the sensitization and challenge phases, treatment with the test compound significantly (>50%) inhibited ear swelling when administered by either route during the challenge phase (FIG. 1).

To determine if topical administration of the test compound was sufficient to inhibit activation of the Jak-STAT pathway, immunohistochemistry was carried out on fixed tissues. Formalin fixed and paraffin embedded ear sections were subjected to immunohistochemical analysis using an antibody that specifically interacts with STAT3 (clone 58E12, Cell Signaling Technologies) Both systemic and topical administration of the test compound visibly reduced the number of infiltrating cells and inhibited phosphorylation of STAT3 in all cell types even when administered after the sensitization phase.

In order to determine the impact of topically applied test compound 3-{(3R,4R)-4-methyl-3-[methyl-(7H-pyrrolo[2,3-d]pyrimidin-4-yl)amino]-piperidin-1-yl}-3-oxo-propionitrile (3%) or dexamtheasone (0.1%) on the DTH transcriptional response, rodent ear tissue tissues were profiled 48 hr post-challenge using Agilent 60-mer oligonucleotide high-density DNA microarray analysis. Downstream image segmentation was performed using Agilent Feature Extractor software and data analysis was performed using Rosetta Resolver v 4.0. Two dimensional clustering was performed using an error-weighted agglomerative clustering algorithm (Rosetta Biosoftware) using average link heuristics and Pearson correlation similarity measures. Statistical significance of all expression data (P<0.01 for inclusion in agglomerative clusters) were error weighted using the duplicate fluorescent-dye reversal data sets as well as an empirical error model based on historical Agilent 60-mer microarray data. Vehicle and drug treated groups were individually compared to the negative control (challenged unsensitized animals) which was used as a baseline. Differences between the respective treated groups and the baseline were then compared to each other. It was demonstrated that a clinically efficacious treatment for psoriasis (dexamtheasone) produced similar transcriptional changes as did the test compound, both qualitatively and quantitatively, in the DTH model (FIG. 2).

Example C

In Vitro Mutant Jak (mtJAK) Assay

Compounds herein can be tested for inhibitory activity of mutant Jak (mtjak) targets according to the following in vitro assay described in Park et al., *Analytical Biochemistry* 1999, 269, 94-104 with variations described herein. Activating mutations, residing anywhere within the coding region of the Jak DNA, cDNA, or mRNA, can be introduced to nucleic acid sequences encoding for Jaks using standard molecular biology techniques (e.g. nucleotide mutagenesis) familiar to those schooled in the art. This includes, but is not limited to mutations in the codon for a.a. 617 that results in a substitution of the wild-type valine with a phenylalanine. The kinase domain (a.a. 828-1132), the pseudo-kinase and kinase domains (a.a. 543-827 and 828-1132, respectively), or the entire Jak protein, with an N-terminal His tag, can be expressed using baculovirus in insect cells and purified. Similar strategies can be employed to generate mutant Jak1, Jak3, or Tyk2. The catalytic activity of Jak can then be assayed by measuring the phosphorylation of a biotinylated peptide. The phosphorylated peptide can be detected by homogenous time resolved fluorescence (HTRF) using suitable and optimized buffers and concentrations of ATP, peptide, kinase, etc. Compounds having an $IC_{50}$ of about 10 µM or less for any of the above-mentioned Jak targets will typically be considered active.

Example D

Cell-Based mtJAK Assay

As a complement to the in vitro kinase assay, cells expressing the mutated form(s) of Jak may be identified (e.g. HEL cells, ATCC) or constructed (by transfection, infection, or similar technique to introduce the nucleic acid encoding for the Jak) using techniques familiar to those schooled in the art. Cells may then be treated with compounds for various times (usually between 0 and 4 hours) and collected for protein extraction using methods familiar to those schooled in the art. Cellular protein extracts can then be analyzed for both total and phospho-Jak using, for example, the following antibodies: total Jak1 (Cell Signaling, #9138), phospho-Jak1 (Abcam, #ab5493), total Jak2 (Upstate #06-255), phospho-Jak (Cell Signaling, #3771), total Jak3 (Santa Cruz, #sc-513), phospho-Jak3 (Santa Cruz, #sc-16567), total Tyk2 (Santa Cruz #sc-169), phospho-Tyk2 (Cell Signal #9321), and phospho-tyrosine (Upstate, #05-231). Methodologies to perform these analyses include but are not limited to immunoblotting, immunoprecipitation, ELISA, RIA, immunocytochemistry, and FACS.

Various modifications of the invention, in addition to those described herein, will be apparent to those skilled in the art from the foregoing description. Such modifications are also intended to fall within the scope of the appended claims. Each reference cited in the present application, including all patents, patent applications, and non-patent literature, is incorporated herein by reference in its entirety.

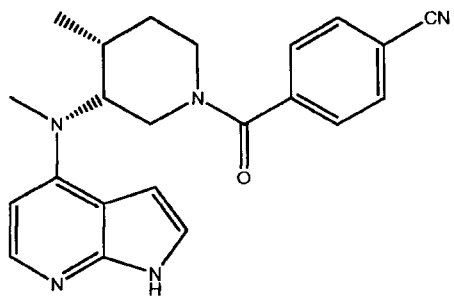

What is claimed is:
1. A compound of Formula I:

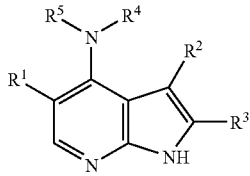

or pharmaceutically acceptable salt form thereof, wherein:
$R^1$, $R^2$, and $R^3$ are each, independently, H, halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$;

$R^4$ is H, $C_{1-4}$ alkyl, $C_{2-4}$ alkenyl, $C_{2-4}$ alkynyl, $S(O)_2R^9$, $SOR^9$, cycloalkyl, or heterocycloalkyl, wherein said $C_{1-4}$ alkyl, $C_{2-4}$ alkenyl, $C_{2-4}$ alkynyl, cycloalkyl, heterocycloalkyl are each optionally substituted with 1, 2 or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$;

$R^5$ is 3-8 membered cycloalkyl, 3-8 membered heterocycloalkyl, —L—(3-8 membered heterocycloalkyl), each substituted by one $R^6$ and 0, 1 or 2 $R^7$;

L is $C_{1-4}$ alkylenyl, $C_{2-4}$ alkenylenyl, $C_{2-4}$ alkynylenyl, O, S, $NR^{14}$, CO, COO, OCO, $NR^{14}C(O)O$, $CONR^{14}$, SO, $SO_2$, $SONR^{14}$, $SO_2NR^{14}$, or $NR^{14}CONR^{14}$;

$R^6$ is —$W^1$—$W^2$—$W^3$—$W^4$—$W^5$—$W^6$—$R^{13}$;

$W^1$ is absent, $C_{1-4}$ alkylenyl, $C_{2-4}$ alkenylenyl, $C_{2-4}$ alkynylenyl, aryl, heteroaryl, cycloalkyl or heterocycloalkyl, each optionally substituted by 1, 2 or 3 halo, CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^2$ is absent, $C_{1-4}$ alkylenyl, $C_{2-4}$ alkenylenyl, $C_{2-4}$ alkynylenyl, O, S, $NR^{12}$, CO, COO, OCO, C(S), $C(S)NR^{12}$, —C(=N—CN)—, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

$W^3$ is absent, $C_{1-4}$ alkylenyl, $C_{2-4}$ alkenylenyl, $C_{2-4}$ alkynylenyl, aryl, cycloalkyl, heteroaryl or heterocycloalkyl, wherein said $C_{1-4}$ alkylenyl, $C_{2-4}$ alkenylenyl, $C_{2-4}$ alkynylenyl, aryl, cycloalkyl, heteroaryl or heterocycloalkyl is optionally substituted by 1, 2 or 3 halo, CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^4$ is absent, $C_{1-4}$ alkylenyl, $C_{2-4}$ alkenylenyl, $C_{2-4}$ alkynylenyl, O, S, $NR^{12}$, CO, COO, OCO, —C(=N—CN)—, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 halo, CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^5$ is absent, $C_{1-4}$ alkylenyl, $C_{2-4}$ alkenylenyl, $C_{2-4}$ alkynylenyl, aryl, cycloalkyl, heteroaryl or heterocycloalkyl, wherein said $C_{1-4}$ alkylenyl, $C_{2-4}$ alkenylenyl, $C_{2-4}$ alkynylenyl, aryl, cycloalkyl, heteroaryl or heterocycloalkyl is optionally substituted by 1, 2 or 3 halo, CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^6$ is absent, $C_{1-4}$ alkyl, $C_{2-4}$ alkenyl, $C_{2-4}$ alkynyl, O, S, $NR^{12}$, CO, COO, OCO, —C(=N—CN)—, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkyl, $C_{2-4}$ alkenyl, $C_{2-4}$ alkynyl are each optionally substituted by 1, 2 or 3 CN, $NO_2$, OH, =NH, =NOH, =NO—($C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$R^7$ is halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, —($C_{1-6}$ alkyl)-CN, —($C_{1-6}$ alkyl)-$NO_2$, —($C_{1-6}$ alkyl)-$OR^{a''}$, —($C_{1-6}$ alkyl)-$SR^{a''}$, —($C_{1-6}$ alkyl)-$C(O)R^{b''}$, —($C_{1-6}$ alkyl)-$C(O)NR^{c''}R^{d''}$, —($C_{1-6}$ alkyl)-$C(O)OR^{a''}$, —($C_{1-6}$ alkyl)-$OC(O)R^{b''}$, —($C_{1-6}$ alkyl)-$OC(O)NR^{c''}R^{d''}$, —($C_{1-6}$ alkyl)-$NR^{c''}R^{d''}$, —($C_{1-6}$ alkyl)-$NR^{c''}C(O)R^{d''}$, —($C_{1-6}$ alkyl)-$NR^{c''}C(O)OR^{a''}$, —($C_{1-6}$ alkyl)-$S(O)R^{b''}$, —($C_{1-6}$ alkyl)-$S(O)NR^{c''}R^{d''}$, —($C_{1-6}$ alkyl)-$S(O)_2R^{b''}$, or —($C_{1-6}$ alkyl)-$S(O)_2NR^{c''}R^{d''}$;

$R^9$ is $C_{1-4}$ alkyl, aryl, heteroaryl, cycloalkyl, or heterocycloalkyl, each optionally substituted with 1, 2, or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, and $S(O)_2NR^{c'}R^{d'}$;

$R^{12}$ and $R^{14}$ are each, independently, H or $C_{1-6}$ alkyl optionally substituted by 1, 2 or 3 substituents selected from OH, CN, $NO_2$, amino, ($C_{1-4}$ alkyl)amino, ($C_{2-8}$ dialkyl)amino, $C_{1-6}$ haloalkyl, $C_{1-6}$ acyl, $C_{1-6}$ acyloxy, $C_{1-6}$ acylamino, —($C_{1-6}$ alkyl)-CN, and —($C_{1-6}$ alkyl)-$NO_2$;

$R^{13}$ is halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, —($C_{1-6}$ alkyl)-CN, —($C_{1-6}$ alkyl)-$NO_2$, —($C_{1-6}$ alkyl)-$OR^{a''}$, —($C_{1-6}$ alkyl)-$SR^{a''}$, —($C_{1-6}$ alkyl)-$C(O)R^{b''}$, —($C_{1-6}$ alkyl)-$C(O)NR^{c''}R^{d''}$, —($C_{1-6}$ alkyl)-$C(O)OR^{a''}$, —($C_{1-6}$ alkyl)-$OC(O)R^{b''}$, —($C_{1-6}$ alkyl)-$OC(O)NR^{c''}R^{d''}$, —($C_{1-6}$ alkyl)-$NR^{c''}R^{d''}$, —($C_{1-6}$ alkyl)-$NR^{c''}C(O)R^{d''}$, —($C_{1-6}$ alkyl)-$NR^{c''}C(O)OR^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, or —(C$_{1-6}$ alkyl)-S(O)$_2$NR$^{c''}$R$^{d''}$, wherein each of said C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl or heterocycloalkylalkyl is optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ (alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ alkyl)-S(O)$_2$NR$^{c''}$R$^{d''}$;

R$^a$, R$^{a'}$ and R$^{a''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^b$, R$^{b'}$ and R$^{b''}$ are each, independently, H, C$_{1-6}$ alkyl, C$_{1-6}$ haloalkyl, C$_{2-6}$ alkenyl, C$_{2-6}$ alkynyl, aryl, cycloalkyl, heteroaryl or heterocycloalkyl;

R$^c$ and R$^d$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^c$ and R$^d$ together with the N atom to which they are attached form a 4-, 5-, 6- or 7-membered heterocycloalkyl group;

R$^{c'}$ and R$^{d'}$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^{c'}$ and R$^{d'}$ together with the N atom to which they are attached form a 4-, 5-, 6- or 7-membered heterocycloalkyl group; and R$^{c''}$ and R$^{d''}$ are each, independently, H, C$_{1-6}$ alkyl, C$_{1-6}$ haloalkyl, C$_{2-6}$ alkenyl, C$_{2-6}$ alkynyl, aryl, cycloalkyl, arylalkyl, or cycloalkylalkyl;

or R$^{c''}$ and R$^{d''}$ together with the N atom to which they are attached form a 4-, 5-, 6- or 7-membered heterocycloalkyl group.

2. The compound of claim 1, or pharmaceutically acceptable salt thereof, wherein R$^1$ is H.

3. The compound of claim 1, or pharmaceutically acceptable salt thereof, wherein R$^2$ is H.

4. The compound of claim 1, or pharmaceutically acceptable salt thereof, wherein R$^3$ is H.

5. The compound of claim 1, or pharmaceutically acceptable salt thereof, wherein R$^4$ is H or C$_{1-4}$ alkyl.

6. The compound of claim 1, or pharmaceutically acceptable salt thereof, wherein R$^4$ is methyl.

7. The compound of claim 1, or pharmaceutically acceptable salt thereof, wherein R$^5$ is 3-8 membered heterocycloalkyl substituted by one R$^6$ and 0, 1 or 2 R$^7$.

8. The compound of claim 1, or pharmaceutically acceptable salt thereof, wherein R$^5$ is 6-membered heterocycloalkyl substituted by one R$^6$ and 0, 1 or 2 R$^7$.

9. The compound of claim 1, or pharmaceutically acceptable salt thereof, wherein R$^5$ is piperidinyl substituted by one R$^6$ and 0, 1 or 2R$^7$.

10. The compound of claim 1, or pharmaceutically acceptable salt thereof, wherein R$^5$ is piperidin-3-yl substituted by one R$^6$ and 0, 1 or 2 R$^7$.

11. The compound of claim 10, or pharmaceutically acceptable salt thereof, wherein R$^6$ is substituted on the piperidinyl N-atom.

12. The compound of claim 1, or pharmaceutically acceptable salt thereof, wherein R$^5$ is —L—pyrrolidinyl; L is C$_{1-4}$ alkylenyl; and said pyrrolidinyl is substituted by one R$^6$ and 0, 1 or 2 R$^7$.

13. The compound of claim 1, or pharmaceutically acceptable salt thereof, wherein R$^5$ is —L—pyrrolidin-2-yl; L is C$_{1-4}$ alkylenyl and said pyrrolidin-2-yl is substituted by one R$^6$ and 0, 1 or 2 R$^7$.

14. The compound of claim 1, or pharmaceutically acceptable salt thereof, wherein W$^2$ is SO$_2$, CO, COO, C(S)NR$^{12}$, or CONR$^{12}$.

15. The compound of claim 1, or pharmaceutically acceptable salt thereof, wherein W$^2$ is SO$_2$, CO, COO, C(S)NH, CONH or —CON(C$_{1-4}$ alkyl)-.

16. The compound of claim 1, or pharmaceutically acceptable salt thereof, wherein W$^2$ is SO$_2$ or CO.

17. The compound of claim 1, or pharmaceutically acceptable salt thereof, wherein W$^3$ is C$_{1-4}$ alkylenyl or cycloalkyl.

18. The compound of claim 1, or pharmaceutically acceptable salt thereof, wherein R$^{13}$ is C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)OR$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ alkyl)-S(O)$_2$NR$^{c''}$R$^{d''}$.

19. The compound of claim 1, or pharmaceutically acceptable salt thereof, wherein R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ alkyl)-S(O)$_2$NR$^{c''}$R$^{d''}$.

20. The compound of claim 1, or pharmaceutically acceptable salt thereof, wherein R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from C$_{1-6}$ alkyl, C$_{1-6}$ haloalkyl, aryl, heteroaryl, halo, CN, OR$^{a''}$, SR$^{a''}$, C(O)R$^{b''}$, C(O)OR$^{a''}$, NR$^{c''}$C(O)R$^{d''}$, S(O)$_2$R$^{b''}$, and —(C$_{1-6}$ alkyl)-CN.

21. The compound of claim 1, or pharmaceutically acceptable salt thereof, wherein R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from C$_{1-6}$ alkyl, C$_{1-6}$ haloalkyl, aryl, heteroaryl, halo, CN, OH, C$_{1-4}$ alkoxy, C$_{1-4}$ haloalkoxy, heteroaryloxy, aryloxy, —SC$_{1-6}$ alkyl, —C(O)—C$_{1-6}$ alkyl, —C(O)OC$_{1-6}$ alkyl, —S(O)$_2$C$_{1-6}$ alkyl, —NHC(O)—C$_{1-6}$ alkyl, and —(C$_{1-6}$ alkyl)-CN.

22. The compound of claim 1, or pharmaceutically acceptable salt thereof, where R$^{13}$ is OH or CN.

23. The compound of claim 1, or pharmaceutically acceptable salt thereof, wherein W$^1$ is absent, W$^2$ is CO or SO$_2$, W$^3$ is C$_{1-4}$ alkyleneyl or cycloalkyl, W$^4$ is absent, W$^5$ is absent, W$^6$ is absent, and R$^{13}$ is CN or OH.

24. The compound of claim 1, or pharmaceutically acceptable salt thereof, wherein R$^6$ is —W$^2$—W$^3$—R$^{13}$.

25. The compound of claim 1, or pharmaceutically acceptable salt thereof, wherein R$^6$ is —CO—CH$_2$—CN.

26. The compound of claim 1, or pharmaceutically acceptable salt thereof, wherein R$^6$ is —W$^2$—R$^{13}$.

27. The compound of claim 1, or pharmaceutically acceptable salt thereof, wherein:

R$^6$ is —W$^2$—R$^{13}$;

W$^2$ is SO$_2$, CO, COO, C(S)NR$^{12}$, or CONR$^{12}$; and

R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$—(C$_{1-6}$alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ alkyl)-S(O)$_2$NR$^{c''}$R$^{d''}$.

28. The compound of claim 1 having the structure of Formula I-A:

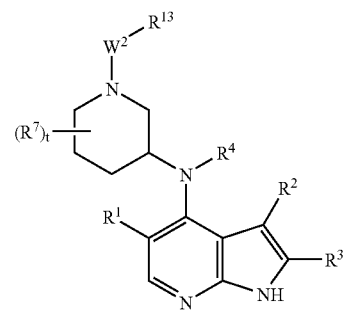

I-A or pharmaceutically acceptable salt thereof, wherein t is 0, 1 or 2.

29. The compound of claim 28, or pharmaceutically acceptable salt thereof, wherein:

W$^2$ is SO$_2$, CO, COO, C(S)NR$^{12}$, or CONR$^{12}$; and

R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from:

C$_{1-6}$ alkyl, C$_{2-6}$ alkenyl, C$_{2-6}$ alkynyl, C$_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, NO$_2$, OR$^{a''}$, SR$^{a''}$, C(O)R$^{b''}$, C(O)NR$^{c''}$R$^{d''}$, C(O)OR$^{a''}$, OC(O)R$^{b''}$, OC(O)NR$^{c''}$R$^{d''}$, NR$^{c''}$R$^{d''}$, NR$^{c''}$C(O)R$^{d''}$, NR$^{c''}$C(O)OR$^{a''}$, S(O)R$^{b''}$, S(O)NR$^{c''}$R$^{d''}$, S(O)$_2$R$^{b''}$, S(O)$_2$NR$^{c''}$R$^{d''}$, —(C$_{1-6}$ alkyl)-CN, —(C$_{1-6}$ alkyl)-NO$_2$, —(C$_{1-6}$ alkyl)-OR$^{a''}$, —(C$_{1-6}$ alkyl)-SR$^{a''}$, —(C$_{1-6}$ alkyl)-C(O)R$^{b''}$, —(C$_{1-6}$ alkyl)-C(O)NR$^{c''}$R$^{d''}$, —(C$_{1-6}$ alkyl)-C(O)OR$^{a''}$, —(C$_{1-6}$ alkyl)-OC(O)R$^{b''}$, —(C$_{1-6}$ alkyl)-OC(O)NR$^{c''}$R$^{d''}$, —(C$_{1-6}$ alkyl)-NR$^{c''}$R$^{d''}$, —(C$_{1-6}$ alkyl)-NR$^{c''}$C(O)R$^{d''}$, —(C$_{1-6}$ alkyl)-NR$^{c''}$C(O)OR$^{a''}$, —(C$_{1-6}$ alkyl)-S(O)R$^{b''}$, —(C$_{1-6}$ alkyl)-S(O)NR$^{c''}$R$^{d''}$, —(C$_{1-6}$ alkyl)-S(O)$_2$R$^{b''}$, and —(C$_{1-6}$ (alkyl)-S(O)$_2$NR$^{c''}$R$^{d''}$.

30. The compound of claim 1 having the structure of Formula I-B:

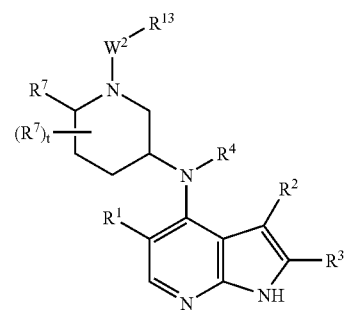

I-B or pharmaceutically acceptable salt thereof, wherein t1 is 0 or 1.

31. The compound of claim 30, or pharmaceutically acceptable salt thereof, wherein R$^{13}$ is C$_{1-6}$ alkyl, C$_{1-6}$ haloalkyl, aryl, cycloalkyl, heteroaryl, heterocycloalkyl, arylalkyl, cycloalkylalkyl, heteroarylalkyl or heterocycloalkylalkyl, each optionally substituted by 1, 2, 3, 4 or 5 substituents independently selected from $C_{1-6}$ alkyl, $C_{1-6}$ haloalkyl, aryl, heteroaryl, halo, CN, $OR^{a''}$, $SR^{a''}$, $C(O)R^{b''}$, $C(O)OR^{a''}$, $NR^{c''}C(O)R^{d''}$, $S(O)_2R^{b''}$, and —($C_{1-6}$ alkyl)-CN;

$W^2$ is $SO_2$, CO, COO, C(S)NH, CONH or —CON($C_{1-4}$ alkyl)-; and $R^4$ is $C_{1-4}$ alkyl, $C_{2-4}$ alkenyl, $C_{2-4}$ alkynyl, $S(O)_2R^9$, $SOR^9$, cycloalkyl, or heterocycloalkyl, wherein said $C_{1-4}$ alkyl, $C_{2-4}$ alkenyl, $C_{2-4}$ alkynyl, cycloalkyl, heterocycloalkyl are each optionally substituted with 1, 2 or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

32. A compound of claim 1 selected from:

3-{3-[methyl(1H-pyrrolo[2,3-b]pyridin-4-yl)amino]piperidin-1-yl}-3-oxopropanenitrile;

3-{(3R,4R)-4-methyl-3-[methyl(1H-pyrrolo[2,3-b]pyridin-4-yl)amino]piperidin-1-yl}-3-oxopropanenitrile;

N-methyl-N-[(3R,4R)-4-methyl-1-(phenylsulfonyl)piperidin-3-yl]-N-(1H-pyrrolo[2,3-b]pyridin-4-yl)-amine;

N-[(3R,4R)-1-(methoxyacetyl)-4-methylpiperidin-3-yl]-N-methyl-N-(1H-pyrrolo[2,3-b]pyridin-4-yl)-amine;

(3R,4R)-4-methyl-3-[methyl(1H-pyrrolo[2,3-b]pyridin-4-yl)amino]-N-phenylpiperidine-1-carboxamide;

(3R,4R)-N-benzyl-4-methyl-3-[methyl(1H-pyrrolo[2,3-b]pyridin-4-yl)amino]piperidine-1-carboxamide;

(3R,4R)-N-ethyl-4-methyl-3-[methyl(1H-pyrrolo[2,3-b]pyridin-4-yl)amino]piperidine-1-carboxamide;

(3R,4R)-N-isopropyl-4-methyl-3-[methyl(1H-pyrrolo[2,3-b]pyridin-4-yl)amino]piperidine-1-carboxamide;

N-[(3R,4R)-1-isobutyryl-4-methylpiperidin-3-yl]-N-methyl-N-(1H-pyrrolo[2,3-b]pyridin-4-yl)-amine;

N-methyl-N-[(3R,4R)-4-methyl-1-(morpholin-4-ylcarbonyl)piperidin-3-yl]-N-(1H-pyrrolo[2,3-b]pyridin-4-yl)-amine;

N-[(3R,4R)-1-acetyl-4-methylpiperidin-3-yl]-N-methyl-N-(1H-pyrrolo[2,3-b]pyridin-4-yl)-amine;

N-methyl-N-[(3R,4R)-4-methyl-1-(3-methylbutanoyl)piperidin-3-yl]-N-(1H-pyrrolo[2,3-b]pyridin-4-yl)-amine;

N-[(3R,4R)-1-benzoyl-4-methylpiperidin-3-yl]-N-methyl-N-(1H-pyrrolo[2,3-b]pyridin-4-yl)-amine;

(3R,4R)-N,N,4-trimethyl-3-[methyl(1H-pyrrolo[2,3-b]pyridin-4-yl)amino]piperidine-1-carboxamide;

4-({(3R,4R)-4-methyl-3-[methyl(1H-pyrrolo[2,3-b]pyridin-4-yl)amino]piperidin-1-yl})carbonyl)benzonitrile;

N-[(3R,4R)-1-(cyclopropylcarbonyl)-4-methylpiperidin-3-yl]-N-methyl-N-(1H-pyrrolo[2,3-b]pyridin-4-yl)-amine;

N-[(3R,4R)-1-isonicotinoyl-4-methylpiperidin-3-yl]-N-methyl-N-(1H-pyrrolo[2,3-b]pyridin-4-yl)-amine;

N-{(3R,4R)-1-[(1-acetylpiperidin-4-yl)carbonyl]-4-methylpiperidin-3-yl}-N-methyl-N-(1H-pyrrolo[2,3-b]pyridin-4-yl)-amine;

Phenyl (3R,4R)-4-methyl-3-[methyl(1H-pyrrolo[2,3-b]pyridin-4-yl)amino]piperidine-1-carboxylate;

Methyl (3R,4R)-4-methyl-3-[methyl(1H-pyrrolo[2,3-b]pyridin-4-yl)amino]piperidine-1-carboxylate;

N-methyl-N-[(3R,4R)-4-methyl-1-(trifluoroacetyl)piperidin-3-yl]-N-(1H-pyrrolo[2,3-b]pyridin-4-yl)-amine;

N-[(3R,4R)-1-(2-furoyl)-4-methylpiperidin-3-yl]-N-methyl-N-(1H-pyrrolo[2,3-b]pyridin-4-yl)-amine;

(3R,4R)-N-(4-cyanophenyl)-4-methyl-3-[methyl(1H-pyrrolo[2,3-b]pyridin-4-yl)amino]piperidine-1-carboxamide;

(3R,4R)-N-(3-cyanophenyl)-4-methyl-3-[methyl(1H-pyrrolo[2,3-b]pyridin-4-yl)amino]piperidine-1-carboxamide;

(3R,4R)-4-methyl-3-[methyl(1H-pyrrolo[2,3-b]pyridin-4-yl)amino]-N-(2-phenylethyl)piperidine-1-carboxamide;

(3R,4R)-N-(2-furylmethyl)-4-methyl-3-[methyl(1H-pyrrolo[2,3-b]pyridin-4-yl)amino]piperidine-1-carboxamide;

N-methyl-N-[(3R,4R)-4-methyl-1-(propylsulfonyl)piperidin-3-yl]-N-(1H-pyrrolo[2,3-b]pyridin-4-yl)-amine;

N-[(3R,4R)-1-(isopropylsulfonyl)-4-methylpiperidin-3-yl]-N-methyl-N-(1H-pyrrolo[2,3-b]pyridin-4-yl)-amine;

4-({(3R,4R)-4-methyl-3-[methyl(1H-pyrrolo[2,3-b]pyridin-4-yl)amino]piperidin-1-yl}sulfonyl)benzonitrile;

2-({(3R,4R)-4-methyl-3-[methyl(1H-pyrrolo[2,3-b]pyridin-4-yl)amino]piperidin-1-yl}sulfonyl)benzonitrile;

N-methyl-N-[(3R,4R)-4-methyl-1-(methylsulfonyl)piperidin-3-yl]-N-(1H-pyrrolo[2,3-b]pyridin-4-yl)-amine;

N-methyl-N-{(3R,4R)-4-methyl-1-[(trifluoromethyl)sulfonyl]piperidin-3-yl}-N-(1H-pyrrolo[2,3-b]pyridin-4-yl)-amine;

N-methyl-N-[(3R,4R)-4-methyl-1-(pyridin-3-ylsulfonyl)piperidin-3-yl]-N-(1H-pyrrolo[2,3-b]pyridin-4-yl)-amine;

2-fluoro-5-({(3R,4R)-4-methyl-3-[methyl(1H-pyrrolo[2,3-b]pyridin-4-yl)amino]piperidin-1-yl}sulfonyl)benzonitrile;

N-methyl-N-[(3R,4R)-4-methyl-1-(3-pyridin-3-ylpropanoyl)piperidin-3-yl]-N-(1H-pyrrolo[2,3-b]pyridin-4-yl)-amine;

N-methyl-N-[(3R,4R)-4-methyl-1-(3,3,3-trifluoropropanoyl)piperidin-3-yl]-N-(1H-pyrrolo[2,3-b]pyridin-4-yl)-amine;

N-methyl-N-[(3R,4R)-4-methyl-1-(tetrahydrofuran-2-ylcarbonyl)piperidin-3-yl]-N-(1H-pyrrolo[2,3-b]pyridin-4-yl)-amine;

(2R)-1-{(3R,4R)-4-methyl-3-[methyl(1H-pyrrolo[2,3-b]pyridin-4-yl)amino]piperidin-1-yl}-1-oxopropan-2-ol;

(2S)-1-{(3R,4R)-4-methyl-3-[methyl(1H-pyrrolo[2,3-b]pyridin-4-yl)amino]piperidin-1-yl}-1-oxopropan-2-ol;

N-methyl-N-[(3R,4R)-4-methyl-1-(3-phenylpropanoyl)piperidin-3-yl]-N-(1H-pyrrolo[2,3-b]pyridin-4-yl)-amine;

(3R,4R)-N-(4-cyanophenyl)-4-methyl-3-[methyl(1H-pyrrolo[2,3-b]pyridin-4-yl)amino]piperidine-1-carbothioamide;

N-methyl-N-{(3R,4R)-4-methyl-1-[(5-methylisoxazol-4-yl)sulfonyl]piperidin-3-yl}-N-(1H-pyrrolo[2,3-b]pyridin-4-yl)-amine;

N-methyl-N-{(3R,4R)-4-methyl-1-[(1-methyl-1H-imidazol-4-yl)sulfonyl]piperidin-3-yl}-N-(1H-pyrrolo[2,3-b]pyridin-4-yl)-amine;

N-{(3R,4R)-1-[(3,5-dimethylisoxazol-4-yl)carbonyl]-4-methylpiperidin-3-yl}-N-methyl-N-(1H-pyrrolo[2,3-b]pyridin-4-yl)-amine;

(3R,4R)-4-methyl-3-[methyl(1H-pyrrolo[2,3-b]pyridin-4-yl)amino]-N-2-thienylpiperidine-1-carboxamide;

N-[(3R,4R)-1-(isoxazol-5-ylcarbonyl)-4-methylpiperidin-3-yl]-N-methyl-N-(1H-pyrrolo[2,3-b]pyridin-4-yl)-amine;

N-{(3R,4R)-1-[(1,2-dimethyl-1H-imidazol-4-yl)sulfonyl]-4-methylpiperidin-3-yl}-N-methyl-N-(1H-pyrrolo[2,3-b]pyridin-4-yl)-amine;

N-[4-methyl-5-({(3R,4R)-4-methyl-3-[methyl(1H-pyrrolo[2,3-b]pyridin-4-yl)amino]piperidin-1-yl}sulfonyl)-1,3-thiazol-2-yl]acetamide;

N-{(3R,4R)-1-[(2,4-dimethyl-1,3-thiazol-5-yl)sulfonyl]-4-methylpiperidin-3-yl}-N-methyl-N-(1H-pyrrolo[2,3-b]pyridin-4-yl)-amine;

N-methyl-N-{(3R,4R)-4-methyl-1-[(1,3,5-trimethyl-1H-pyrazol-4-yl)sulfonyl]piperidin-3-yl}-N-(1H-pyrrolo[2,3-b]pyridin-4-yl)-amine;

N-{(3R,4R)-1-[(3,5-dimethylisoxazol-4-yl)sulfonyl]-4-methylpiperidin-3-yl}-N-methyl-N-(1H-pyrrolo[2,3-b]pyridin-4-yl)-amine;

N-methyl-N-{(3R,4R)-4-methyl-1-[(pyridin-4-ylmethyl)sulfonyl]piperidin-3-yl}-N-(1H-pyrrolo[2,3-b]pyridin-4-yl)-amine;

N-methyl-N-{(3R,4R)-4-methyl-1-[(pyridin-3-ylmethyl)sulfonyl]piperidin-3-yl}-N-(1H-pyrrolo[2,3-b]pyridin-4-yl)-amine;

N-methyl-N-{(3R,4R)-4-methyl-1-[(pyridin-2-ylmethyl)sulfonyl]piperidin-3-yl}-N-(1H-pyrrolo[2,3-b]pyridin-4-yl)-amine;

4-({(3R,4R)-4-methyl-3-[methyl(1H-pyrrolo[2,3-b]pyridin-4-yl)amino]piperidin-1-yl}sulfonyl)benzonitrile;

(3R,4R)-N-(4-cyanophenyl)-N,4-dimethyl-3-[methyl(1H-pyrrolo[2,3-b]pyridin-4-yl)amino]piperidine-1-carboxamide;

(3R,4R)-N-(4-cyanophenyl)-N-ethyl-4-methyl-3-[methyl(1H-pyrrolo[2,3-b]pyridin-4-yl)amino]piperidine-1-carboxamide;

(3R,4R)-4-methyl-3-[methyl(1H-pyrrolo[2,3-b]pyridin-4-yl)amino]-N-1,3-thiazol-2-ylpiperidine-1-carboxamide;

(3R,4R)-4-methyl-N-(3-methylisoxazol-5-yl)-3-[methyl(1H-pyrrolo[2,3-b]pyridin-4-yl)amino]piperidine-1-carboxamide;

3-chloro-4-({(3R,4R)-4-methyl-3-[methyl(1H-pyrrolo[2,3-b]pyridin-4-yl)amino]piperidin-1-yl}sulfonyl)benzonitrile;

(3R,4R)-4-methyl-N-(5-methylisoxazol-3-yl)-3-[methyl(1H-pyrrolo[2,3-b]pyridin-4-yl)amino]piperidine-1-carboxamide;

(3R,4R)-N-isoxazol-3-yl-4-methyl-3-[methyl(1H-pyrrolo[2,3-b]pyridin-4-yl)amino]piperidine-1-carboxamide;

N-methyl-N-{(3R,4R)-4-methyl-1-[(5-pyridin-3-yl-2-thienyl)sulfonyl]piperidin-3-yl}-N-(1H-pyrrolo[2,3-b]pyridin-4-yl)-amine;

(3R,4R)-N-(3-cyano-2-thienyl)-4-methyl-3-[methyl(1H-pyrrolo[2,3-b]pyridin-4-yl)amino]piperidine-1-carboxamide;

(3R,4R)-N-1,3-benzothiazol-2-yl-4-methyl-3-[methyl(1H-pyrrolo[2,3-b]pyridin-4-yl)amino]piperidine-1-carboxamide;

N-[(3R,4R)-1-(2,3-dihydro-1H-indol-1-ylcarbonyl)-4-methylpiperidin-3-yl]-N-methyl-N-(1H-pyrrolo[2,3-b]pyridin-4-yl)-amine;

N-methyl-N-{(3R,4R)-4-methyl-1-[(methylthio)acetyl]piperidin-3-yl}-N-(1H-pyrrolo[2,3-b]pyridin-4-yl)-amine;

(3R,4R)-N-(4,5-dihydro-1,3-thiazol-2-yl)-4-methyl-3-[methyl(1H-pyrrolo[2,3-b]pyridin-4-yl)amino]piperidine-1-carboxamide;

(3R,4R)-4-methyl-3-[methyl(1H-pyrrolo[2,3-b]pyridin-4-yl)amino]-N-(1,3-thiazol-2-ylmethyl)piperidine-1-carboxamide;

1-({(3R,4R)-4-methyl-3-[methyl(1H-pyrrolo[2,3-b]pyridin-4-yl)amino]piperidin-1-yl}carbonyl)piperidine-4-carbonitrile;

1-({(3R,4R)-4-methyl-3-[methyl(1H-pyrrolo[2,3-b]pyridin-4-yl)amino]piperidin-1-yl}carbonyl)piperidine-3-carbonitrile;

1-({(3R,4R)-4-methyl-3-[methyl(1H-pyrrolo[2,3-b]pyridin-4-yl)amino]piperidin-1-yl}carbonyl)pyrrolidine-3-carbonitrile;

(3R,4R)-4-methyl-3-[methyl(1H-pyrrolo[2,3-b]pyridin-4-yl)amino]-N-(3-thienylmethyl)piperidine-1-carboxamide;

(3R,4R)-N-(2-benzothien-1-ylmethyl)-4-methyl-3-[methyl(1H-pyrrolo[2,3-b]pyridin-4-yl)amino]piperidine-1-carboxamide;

(3R,4R)-N-(1,3-benzothiazol-2-ylmethyl)-4-methyl-3-[methyl(1H-pyrrolo[2,3-b]pyridin-4-yl)amino]piperidine-1-carboxamide;

N-[(3R,4R)-1-(3-furylacetyl)-4-methylpiperidin-3-yl]-N-methyl-N-(1H-pyrrolo[2,3-b]pyridin-4-yl)-amine;

3-(2-{(3R,4R)-4-methyl-3-[methyl(1H-pyrrolo[2,3-b]pyridin-4-yl)amino]piperidin-1-yl}-2-oxoethyl)-1,3-thiazolidine-2,4-dione;

3-(2-{(3R,4R)-4-methyl-3-[methyl(1H-pyrrolo[2,3-b]pyridin-4-yl)amino]piperidin-1-yl}-2-oxoethyl)-1,3-benzothiazol-2(3H)-one;

(3R,4R)-N-[5-(cyanomethyl)-4,5-dihydro,-1,3-thiazol-2-yl]-3-[methyl-(1H-pyrrolo[2,3-b]pyridin-4-yl)amino]-4-methyl-piperidine-1-carboxamide;

(3S)-1-({(3R,4R)-4-methyl-3-[methyl(1H-pyrrolo[2,3-b]pyridin-4-yl)amino]piperidin-1-yl}carbonyl)pyrrolidine-3-carbonitrile;

(3R)-1-({(3R,4R)-4-methyl-3-[methyl(1H-pyrrolo[2,3-b]pyridin-4-yl)amino]piperidin-1-yl}carbonyl)pyrrolidine-3-carbonitrile;

1-({(3R,4R)-4-methyl-3-[methyl(1H-pyrrolo[2,3-b]pyridin-4-yl)amino]piperidin-1-yl}carbonyl)-4-phenylpiperidine-4-carbonitrile;

N-methyl-N-((3R,4R)-4-methyl-1-{[3-(trifluoromethyl)pyrrolidin-1-yl]carbonyl}piperidin-3-yl)-N-(1H-pyrrolo[2,3-b]pyridin-4-yl)-amine;

1-({(3R,4R)-4-methyl-3-[methyl(1H-pyrrolo[2,3-b]pyridin-4-yl)amino]piperidin-1-yl}carbonyl)azetidine-3-carbonitrile;

4-methyl-1-({(3R,4R)-4-methyl-3-[methyl(1H-pyrrolo[2,3-b]pyridin-4-yl)amino]piperidin-1-yl}carbonyl)pyrrolidine-3-carbonitrile;

1-({(3R,4R)-4-methyl-3-[methyl(1H-pyrrolo[2,3-b]pyridin-4-yl)amino]piperidin-1-yl}carbonyl)pyrrolidine-3,4-dicarbonitrile;

3-methyl-1-({(3R,4R)-4-methyl-3-[methyl(1H-pyrrolo[2,3-b]pyridin-4-yl)amino]piperidin-1-yl}carbonyl)pyrrolidine-3-carbonitrile;

(3R,4R)-N-(2-cyanoethyl)-4-methyl-3-[methyl(1H-pyrrolo[2,3-b]pyridin-4-yl)amino]piperidine-1-carboxamide;

4-methoxy-1-({(3R,4R)-4-methyl-3-[methyl(1H-pyrrolo[2,3-b]pyridin-4-yl)amino]piperidin-1-yl}carbonyl)pyrrolidine-3-carbonitrile;

N-{(3R,4R)-1-[(2R)-2-aminopropanoyl]-4-methylpiperidin-3-yl}-N-methyl-N-(1H-pyrrolo[2,3-b]pyridin-4-yl)-amine;

N-[(3R,4R)-1-(aminoacetyl)-4-methylpiperidin-3-yl]-N-methyl-N-(1H-pyrrolo[2,3-b]pyridin-4-yl)-amine;

1-(2-{(3R,4R)-4-methyl-3-[methyl(1H-pyrrolo[2,3-b]pyridin-4-yl)amino]piperidin-1-yl}-2-oxoethyl)piperidine-4-carbonitrile;

N-methyl-N-[(3R,4R)-4-methyl-1-(1,3-thiazol-4-ylcarbonyl)piperidin-3-yl]-N-(1H-pyrrolo[2,3-b]pyridin-4-yl)-amine bis (trifluoroacetate);

4-(2-2S-{[methyl-(1H-pyrrolo[2,3-b]pyridin-4-yl)-amino]-methyl}-pyrrolidin-1-yl-sulfonyl)-benzonitrile trifluoroacetate;

N-[(1-methanesulfonyl-2S-pyrrolidin-2-yl)-methyl]-N-methyl-N-(1H-pyrrolo[2,3-b]pyridin-4-yl)-amine trifluoroacetate;

3-((2S)-2-{[methyl(1H-pyrrolo[2,3-b]pyridin-4-yl)amino]methyl}pyrrolidin-1-yl)-3-oxopropanenitrile trifluoroacetate;

Methyl 3-[({(3R,4R)-4-methyl-3-[methyl(1H-pyrrolo[2,3-b]pyridin-4-yl)amino]piperidine-1-yl}carbonyl)-amino]benzoate;

(3R,4R)-N-(4-trifluoromethoxyphenyl)-4-methyl-3-[methyl-(1H-pyrrolo[2,3-b]pyridin-4-yl)amino]piperidine-1-carboxamide;

(3R,4R)-N-(4-fluorophenyl)-4-methyl-3-[methyl-(1H-pyrrolo[2,3-b]pyridin-4-yl)amino]piperidine-1-carboxamide;

(3R,4R)-N-(3-fluorophenyl)-4-methyl-3-[methyl-(1H-pyrrolo[2,3-b]pyridin-4-yl)amino]piperidine-1-carboxamide;

(3R,4R)-N-(2-fluorophenyl)-4-methyl-3-[methyl-(1H-pyrrolo[2,3-b]pyridin-4-yl)amino]piperidine-1-carboxamide;

(3R,4R)-N-(4-trifluoromethylphenyl)-4-methyl-3-[methyl-(1H-pyrrolo[2,3-b]pyridin-4-yl)amino]piperidine-1-carboxamide;

(3R,4R)-N-(2-methoxyphenyl)-4-methyl-3-[methyl(1H-pyrrolo[2,3-b]pyridin-4-yl)amino]piperidine-1-carboxamide;

(3R,4R)-4-methyl-N-(4-methylphenyl)-3-[methyl(1H-pyrrolo[2,3-b]pyridin-4-yl)-amino]piperidine-1-carboxamide;

N-methyl-N-{(3R,4R)-4-methyl-1-[4-(pyridin-2-yloxy)phenyl]sulfonyl-piperidin-3-yl}-N-(1H-pyrrolo[2,3-b]pyridin-4-yl)-amine;

N-methyl-N-{(3R,4R)-4-methyl-1-[4-(1,3-oxazol-5-yl)phenyl]sulfonyl-piperidin-3-yl}-N-(1H-pyrrolo[2,3-b]pyridin-4-yl)-amine;

N-methyl-N-{(3R,4R)-4-methyl-1-[5-(1,3-oxazol-5-yl)thienyl]sulfonyl-piperidin-3-yl}-N-(1H-pyrrolo[2,3-b]pyridin-4-yl)-amine;

N-methyl-N-{(3R,4R)-4-methyl-1-[(6-phenoxy-pyridin-3-yl)sulfonyl]piperidin-3-yl}-(1H-pyrrolo[2,3-b]pyridin-4-yl)amine;

N-{(3R,4R)-1-[(2,6-dichlorophenyl)sulfonyl]-4-methylpiperidin-3-yl}-N-methyl-(1H-pyrrolo[2,3-b]pyridin-4-yl)-amine;

N-{(3R,4R)-1-[(4-fluorophenyl)sulfonyl]-4-methylpiperidin-3-yl}-N-methyl-(1H-pyrrolo[2,3-b]pyridin-4-yl)-amine;

N-{(3R,4R)-1-[(3-fluorophenyl)sulfonyl]-4-methylpiperidin-3-yl}-N-methyl-(1H-pyrrolo[2,3-b]pyridin-4-yl)-amine;

N-{(3R,4R)-1-[(2-fluorophenyl)sulfonyl]-4-methylpiperidin-3-yl}-N-methyl-(1H-pyrrolo[2,3-b]pyridin-4-yl)-amine;

N-{(3R,4R)-4-methyl-1-[4-(trifluoromethyl)phenyl]sulfonyl-piperidin-3-yl}-N-(1H-pyrrolo[2,3-b]pyridin-4-yl)-amine;

N-{(3R,4R)-4-methyl-1-[3-(trifluoromethyl)phenyl]sulfonyl-piperidin-3-yl}-N-(1H-pyrrolo[2,3-b]pyridin-4-yl)-amine;

N-{(3R,4R)-4-methyl-1-[2-(trifluoromethyl)phenyl]sulfonyl-piperidin-3-yl}-N-(1H-pyrrolo[2,3-b]pyridin-4-yl)-amine;

N-{(3R,4R)-1-[(4-methoxyphenyl)sulfonyl]-4-methylpiperidin-3-yl}-N-methyl-N-(1H-pyrrolo[2,3-b]pyridin-4-yl)-amine;

N-{(3R,4R)-1-[(3-methoxyphenyl)sulfonyl]-4-methylpiperidin-3-yl}-N-methyl-N-(1H-pyrrolo[2,3-b]pyridin-4-yl)-amine;

N-methyl-N-{(3R,4R)-4-methyl-1-[(4-methylphenyl)sulfonyl]piperidin-3-yl}-N-(1H-pyrrolo[2,3-b]pyridin-4-yl)-amine;

N-methyl-N-{(3R,4R)-4-methyl-1-[(3-methylphenyl)sulfonyl]piperidin-3-yl}-N-(1H-pyrrolo[2,3-b]pyridin-4-yl)-amine;

N-methyl-N-{(3R,4R)-4-methyl-1-[(2-methylphenyl)sulfonyl]piperidin-3-yl}-N-(1H-pyrrolo[2,3-b]pyridin-4-yl)-amine;

N-{(3R,4R)-1-[(4-chlorophenyl)sulfonyl]-4-methylpiperidin-3-yl}-N-methyl-N-(1H-pyrrolo[2,3-b]pyridin-4-yl)-amine;

N-{(3R,4R)-1-[(3-chlorophenyl)sulfonyl]-4-methylpiperidin-3-yl}-N-methyl-N-(1H-pyrrolo[2,3-b]pyridin-4-yl)-amine; and N-{(3R,4R)-1-[(2-chlorophenyl)sulfonyl]-4-methylpiperidin-3-yl}-N-methyl-N-(1H-pyrrolo[2,3-b]pyridin-4-yl)-amine, or a pharmaceutically acceptable salt thereof.

33. A composition comprising a compound of claim 1, or pharmaceutically acceptable salt thereof, and a pharmaceutically acceptable carrier.

34. A pharmaceutical composition for topical administration comprising a compound of Formula II:

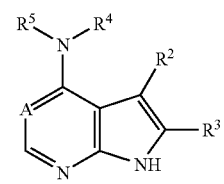

or pharmaceutically acceptable salt form thereof, wherein:

A is N or CR$^1$;

R$^1$, R$^2$, and R$^3$ are each, independently, H, halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$;

R$^4$ is H, C$_{1-4}$ alkyl, C$_{2-4}$ alkenyl, C$_{2-4}$ alkynyl, S(O)$_2$R$^9$, SOR$^9$, cycloalkyl, or heterocycloalkyl, wherein said C$_{1-4}$ alkyl, C$_{2-4}$ alkenyl, C$_{2-4}$ alkynyl, cycloalkyl, heterocycloalkyl are each optionally substituted with 1, 2 or 3 substituents selected from halo, C$_{1-4}$ alkyl, C$_{2-4}$ alkenyl, C$_{2-4}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

R$^5$ is 3-8 membered cycloalkyl, 3-8 membered heterocycloalkyl, —L—(3-8 membered cycloalkyl), —L—(3-8 membered heterocycloalkyl), each substituted by one R$^6$ and 0, 1 or 2 R$^7$;

L is $C_{1-4}$ alkylenyl, $C_{2-4}$ alkenylenyl, $C_{2-4}$ alkynylenyl, O, S, $NR^{14}$, CO, COO, OCO, $NR^{14}C(O)O$, $CONR^{14}$, SO, $SO_2$, $SONR^{14}$, $SO_2NR^{14}$, or $NR^{14}CONR_{14}$;

$R^6$ is $-W^1-W^2-W^3-W^4-W^5-W^6-R^{13}$;

$W^1$ is absent, $C_{1-4}$ alkylenyl, $C_{2-4}$ alkenylenyl, $C_{2-4}$ alkynylenyl, aryl, heteroaryl, cycloalkyl or heterocycloalkyl, each optionally substituted by 1, 2 or 3 halo, CN, $NO_2$, OH, $=NH$, $=NOH$, $=NO-(C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^2$ is absent, $C_{1-4}$ alkylenyl, $C_{2-4}$ alkenylenyl, $C_{2-4}$ alkynylenyl, O, S, $NR^{12}$, CO, COO, OCO, C(S), $C(S)NR^{12}$, $-C(=N-CN)-$, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

$W^3$ is absent, $C_{1-4}$ alkylenyl, $C_{2-4}$ alkenylenyl, $C_{2-4}$ alkynylenyl, aryl, cycloalkyl, heteroaryl or heterocycloalkyl, wherein said $C_{1-4}$ alkylenyl, $C_{2-4}$ alkenylenyl, $C_{2-4}$ alkynylenyl, aryl, cycloalkyl, heteroaryl or heterocycloalkyl is optionally substituted by 1, 2 or 3 halo, CN, $NO_2$, OH, $=NH$, $=NOH$, $=NO-(C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^4$ is absent, $C_{1-4}$ alkylenyl, $C_{2-4}$ alkenylenyl, $C_{2-4}$ alkynylenyl, O, S, $NR^{12}$, CO, COO, OCO, $-C(=N-CN)-$, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkylenyl, $C_{2-4}$ alkenylenyl, $C_{2-4}$ alkynylenyl, are each optionally substituted by 1, 2 or 3 halo, CN, $NO_2$, OH, $=NH$, $=NOH$, $=NO-(C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^5$ is absent, $C_{1-4}$ alkylenyl, $C_{2-4}$ alkenylenyl, $C_{2-4}$ alkynylenyl, aryl, cycloalkyl, heteroaryl or heterocycloalkyl, wherein said $C_{1-4}$ alkylenyl, $C_{2-4}$ alkenylenyl, $C_{2-4}$ alkynylenyl, aryl, cycloalkyl, heteroaryl or heterocycloalkyl is optionally substituted by 1, 2 or 3 halo, CN, $NO_2$, OH, $=NH$, $=NOH$, $=NO-(C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$W^6$ is absent, $C_{1-4}$ alkyl, $C_{2-4}$ alkenyl, $C_{2-4}$ alkynyl, O, S, $NR^{12}$, CO, COO, OCO, $-C(=N-CN)-$, $NR^{12}C(O)O$, $CONR^{12}$, SO, $SO_2$, $SONR^{12}$, $SO_2NR^{12}$, or $NR^{12}CONR^{12}$, wherein said $C_{1-4}$ alkyl, $C_{2-4}$ alkenyl, $C_{2-4}$ alkynyl are each optionally substituted by 1, 2 or 3 CN, $NO_2$, OH, $=NH$, $=NOH$, $=NO-(C_{1-4}$ alkyl), $C_{1-4}$ haloalkyl, $C_{1-4}$ alkoxy, $C_{1-4}$ haloalkoxy, amino, $C_{1-4}$ alkylamino or $C_{2-8}$ dialkylamino;

$R^7$ is halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, $-(C_{1-6}$ alkyl)-CN, $-(C_{1-6}$ alkyl)-$NO_2$, $-(C_{1-6}$ alkyl)-$OR^{a''}$, $-(C_{1-6}$ alkyl)-$SR^{a''}$, $-(C_{1-6}$ alkyl)-$C(O)R^{b''}$, $-(C_{1-6}$ alkyl)-$C(O)NR^{c''}R^{d''}$, $-(C_{1-6}$ alkyl)-$C(O)OR^{a''}$, $-(C_{1-6}$ alkyl)-$OC(O)R^{b''}$, $-(C_{1-6}$ alkyl)-$OC(O)NR^{c''}R^{d''}$, $-(C_{1-6}$ alkyl)-$NR^{c''}R^{d''}$, $-(C_{1-6}$ alkyl)-$NR^{c''}C(O)R^{d''}$, $-(C_{1-6}$ alkyl)-$NR^{c''}C(O)OR^{a''}$, $-(C_{1-6}$ alkyl)-$S(O)R^{b''}$, $-(C_{1-6}$ alkyl)-$S(O)NR^{c''}R^{d''}$, $-(C_{1-6}$ alkyl)-$S(O)_2R^{b''}$, or $-(C_{1-6}$ alkyl)-$S(O)_2NR^{c''}R^{d''}$;

$R^9$ is $C_{1-4}$ alkyl, aryl, heteroaryl, cycloalkyl, or heterocycloalkyl, each optionally substituted with 1, 2, or 3 substituents selected from halo, $C_{1-4}$ alkyl, $C_{2-4}$ alkenyl, $C_{2-4}$ alkynyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, and $S(O)_2NR^{c'}R^{d'}$;

$R^{12}$ and $R^{14}$ are each, independently, H or $C_{1-6}$ alkyl optionally substituted by 1, 2 or 3 substituents selected from OH, CN, $NO_2$, amino, $(C_{1-4}$ alkyl)amino, $(C_{2-8}$ dialkyl)amino, $C_{1-6}$ haloalkyl, $C_{1-6}$ acyl, $C_{1-6}$ acyloxy, $C_{1-6}$ acylamino, $-(C_{1-6}$ alkyl)-CN, and $-(C_{1-6}$ alkyl)-$NO_2$;

$R^{13}$ is halo, $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, $-(C_{1-6}$ alkyl)-CN, $-(C_{1-6}$ alkyl)-$NO_2$, $-(C_{1-6}$ alkyl)-$OR^{a''}$, $-(C_{1-6}$ alkyl)-$SR^{a''}$, $-(C_{1-6}$ alkyl)-$C(O)R^{b''}$, $-(C_{1-6}$ alkyl)-$C(O)NR^{c''}R^{d''}$, $-(C_{1-6}$ alkyl)-$C(O)OR^{a''}$, $-(C_{1-6}$ alkyl)-$OC(O)R^{b''}$, $-(C_{1-6}$ alkyl)-$OC(O)NR^{c''}R^{d''}$, $-(C_{1-6}$ alkyl)-$NR^{c''}R^{d''}$, $-(C_{1-6}$ alkyl)-$NR^{c''}C(O)R^{d''}$, $-(C_{1-6}$ alkyl)-$NR^{c''}C(O)OR^{a''}$, $-(C_{1-6}$ alkyl)-$S(O)R^{b''}$, $-(C_{1-6}$ alkyl)-$S(O)NR^{c''}R^{d''}$, $-(C_{1-6}$ alkyl)-$S(O)_2R^{b''}$, or $-(C_{1-6}$ alkyl)-$S(O)_2NR^{c''}R^{d''}$, wherein each of said $C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl or heterocycloalkylalkyl is optionally substituted by 1, 2, 3, 4 or 5 substituents independently selected from:

$C_{1-6}$ alkyl, $C_{2-6}$ alkenyl, $C_{2-6}$ alkynyl, $C_{1-6}$ haloalkyl, aryl, cycloalkyl, heteroaryl, heterocycloalkyl, arylalkyl, cycloalkylalkyl, heteroarylalkyl, heterocycloalkylalkyl, halo, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, $S(O)_2NR^{c''}R^{d''}$, $-(C_{1-6}$ alkyl)-CN, $-(C_{1-6}$ alkyl)-$NO_2$, $-(C_{1-6}$ alkyl)-$OR^{a''}$, $-(C_{1-6}$ alkyl)-$SR^{a''}$, $-(C_{1-6}$ alkyl)-$C(O)R^{b''}$, $-(C_{1-6}$ alkyl)-$C(O)NR^{c''}R^{d''}$, $-(C_{1-6}$ alkyl)-$C(O)OR^{a''}$, $-(C_{1-6}$ alkyl)-$OC(O)R^{b''}$, $-(C_{1-6}$ alkyl)-$OC(O)NR^{c''}R^{d''}$, $-(C_{1-6}$ alkyl)-$NR^{c''}R^{d''}$, $-(C_{1-6}$ alkyl)-$NR^{c''}C(O)R^{d''}$, $-(C_{1-6}$ alkyl)-$NR^{c''}C(O)OR^{a''}$, $-(C_{1-6}$ alkyl)-$S(O)R^{b''}$, $-(C_{1-6}$ alkyl)-$S(O)NR^{c''}R^{d''}$, $-(C_{1-6}$ alkyl)-$S(O)_2R^{b''}$, and $-(C_{1-6}$ alkyl)-$S(O)_2NR^{c''}R^{d''}$;

$R^a$, $R^{a'}$ and $R^{a''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^b$, $R^{b'}$ and $R^{b''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl;

$R^c$ and $R^d$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^c$ and $R^d$ together with the N atom to which they are attached form a 4-, 5-, 6- or 7-membered heterocycloalkyl group;

$R^{c'}$ and $R^{d'}$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^{c'}$ and $R^{d'}$ together with the N atom to which they are attached form a 4-, 5-, 6- or 7-membered heterocycloalkyl group; and $R^{c''}$ and $R^{d''}$ are each, independently, H, $C_{1-6}$ alkyl, $C_{1-6}$ haloalkyl, $C_{2-6}$ alkenyl, $C_{2-6}$ alkynyl, aryl, cycloalkyl, arylalkyl, or cycloalkylalkyl;

or $R^{c''}$ and $R^{d''}$ together with the N atom to which they are attached form a 4-, 5-, 6- or 7-membered heterocycloalkyl group.

35. The composition of claim 34 wherein said topical administration comprises transdermal administration.

36. The composition of claim 34 which is in the form of a transdermal patch, ointment, lotion, cream, or gel.

37. The composition of claim 34 wherein A is $CR^1$.

38. The composition of claim 34 wherein A is N.

* * * * *

UNITED STATES PATENT AND TRADEMARK OFFICE
CERTIFICATE OF CORRECTION

Page 1 of 2

PATENT NO. : 7,335,667 B2
APPLICATION NO. : 11/313394
DATED : February 26, 2008
INVENTOR(S) : James D. Rodgers et al.

It is certified that error appears in the above-identified patent and that said Letters Patent is hereby corrected as shown below:

In Claim 1, Col. 79, Line 31, delete "$NR^cC(O)OR^a,S(O)R^b$," and insert -- $NR^cC(O)OR^a, S(O)R^b$ --, therefor.

In Claim 1, Col. 80, Line 34, delete "—$(C_{1-6}$alkyl)-" and insert -- —$(C_{1-6}$ alkyl)- --, therefor.

In Claim 1, Col. 80, Lines 60-61, delete "$NR^{c"}C(O)R^{d"}NR^{c"}C(O)OR^{a"},S(O)R^{b"}$," and insert -- $NR^{c"}C(O)R^{d"}, NR^{c"}C(O)OR^{a"}, S(O)R^{b"}$, --, therefor.

In Claim 1, Col. 81, Line 2, delete "$NR^{c"}R^{d"}$,—$(C_{1-6}$ alkyl)" and insert -- $NR^{c"}R^{d"}$, —$(C_{1-6}$ alkyl)--, therefor.

In Claim 1, Col. 81, Line 17, delete "alkyl)-$OR^{a"}$,—$(C_{1-6}$ alkyl)" and insert -- alkyl)-$OR^{a"}$, —$(C_{1-6}$ alkyl) --, therefor.

In Claim 1, Col. 81, Line 18, delete "$C(O)NR^{c"}R^{d"}$,—$(C_{1-6}$ alkyl)" and insert -- $C(O)NR^{c"}R^{d"}$, —$(C_{1-6}$ alkyl) --, therefor.

In Claim 9, Col. 81, Line 67, delete "$2R^7$." and insert -- 2 $R^7$. --, therefor.

In Claim 19, Col. 82, Line 63, delete "—$(C_{1-6}$ alkyl)-$SR^{a"}$" and insert -- —$(C_{1-6}$ alkyl)-$SR^{a"}$, --, therefor.

In Claim 22, Col. 83, Line 26, delete "where" and insert -- wherein --, therefor.

In Claim 23, Col. 83, Line 30, delete "alkyleneyl" and insert -- alkylenyl --, therefor.

In Claim 27, Col. 83, Line 61, delete "—$(C_{1-6}$ alkyl)-$SR^{a"}$" and insert -- —$(C_{1-6}$ alkyl)-$SR^{a"}$, --, therefor.

Signed and Sealed this
Seventeenth Day of April, 2012

David J. Kappos
*Director of the United States Patent and Trademark Office*

CERTIFICATE OF CORRECTION (continued)
U.S. Pat. No. 7,335,667 B2

In Claim 30, Col. 84, Lines 46-57, Formula I-B should read,

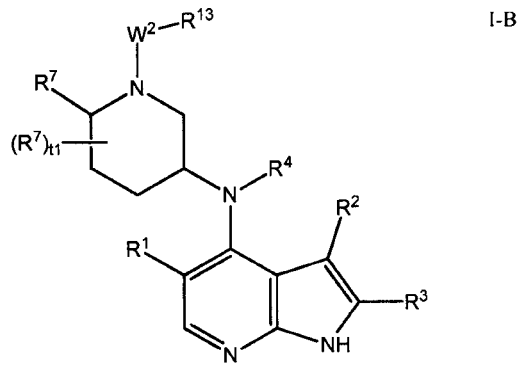

In Claim 32, Col. 89, Line 24, delete "5-dihydro,-1," and insert -- 5-dihydro-1, --, therefor.

In Claim 50, Col. 91, Line 3, delete "$NR^{14}CONR_{14}$;" and insert -- $NR^{14}CONR^{14}$; --, therefor.

In Cols. 31-32, Table 1, structure for Ex. No. 3 should read,

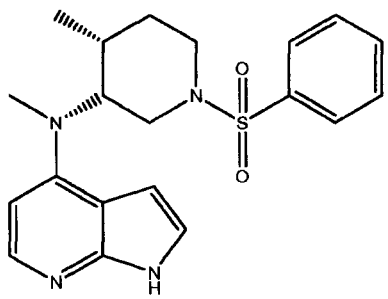

In Cols. 35-36, Table 1, structure for Ex. No. 15 should read,